United States Patent
Philip et al.

(10) Patent No.: US 6,652,850 B1
(45) Date of Patent: *Nov. 25, 2003

(54) ADENO-ASSOCIATED VIRAL LIPOSOMES AND THEIR USE IN TRANSFECTING DENDRITIC CELLS TO STIMULATE SPECIFIC IMMUNITY

(75) Inventors: Ramila Philip, Redwood City, CA (US); Jane S. Lebkowski, Portola Valley, CA (US)

(73) Assignee: Aventis Pharmaceuticals Inc., Bridgewater, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/000,003
(22) PCT Filed: Jul. 19, 1996
(86) PCT No.: PCT/US96/12012
§ 371 (c)(1), (2), (4) Date: Jun. 15, 1998
(87) PCT Pub. No.: WO97/03703
PCT Pub. Date: Feb. 6, 1997

Related U.S. Application Data

(63) Continuation-in-part of application No. 08/566,286, filed on Dec. 1, 1995, now abandoned, and a continuation-in-part of application No. 08/305,221, filed on Sep. 12, 1994, now Pat. No. 5,834,441, which is a continuation-in-part of application No. 08/120,605, filed on Sep. 13, 1993, now abandoned.

(60) Provisional application No. 60/001,312, filed on Jul. 21, 1995, and provisional application No. 60/007,184, filed on Nov. 1, 1995.

(51) Int. Cl.$^7$ .......................... A61K 48/00; C12N 5/02; C12N 15/00; C12N 15/63
(52) U.S. Cl. ................ 424/93.21; 424/93.2; 435/320.1; 435/325; 435/455; 514/44
(58) Field of Search .................. 514/44; 424/93.21; 435/325, 455, 320.1; 421/93.2

(56) References Cited

U.S. PATENT DOCUMENTS

| | | | |
|---|---|---|---|
| 4,394,448 A | 7/1983 | Szoka, Jr. et al. | 435/172 |
| 4,935,372 A | 6/1990 | Goh | 435/371.1 |
| 5,126,132 A | 6/1992 | Rosenberg | 424/93 |
| 5,139,941 A | 8/1992 | Muzyczka et al. | 435/69.1 |
| 5,173,414 A | 12/1992 | Lebkowski et al. | 435/172.3 |
| 5,198,344 A | 3/1993 | Croop et al. | 435/69.1 |
| 5,204,259 A | 4/1993 | Helting et al. | 435/252.3 |
| 5,229,500 A | 7/1993 | Barde et al. | 530/399 |
| 5,250,431 A | 10/1993 | Rudd et al. | 435/240.2 |
| 5,252,479 A | 10/1993 | Srivastava et al. | 435/235.1 |
| 5,342,774 A | 8/1994 | Boon et al. | 435/235 |
| 5,399,346 A | 3/1995 | Anderson et al. | 424/93.21 |
| 5,436,146 A | 7/1995 | Shenk et al. | 435/172.3 |
| 5,587,308 A | * 12/1996 | Carter et al. | 435/240.2 |
| 5,593,972 A | 1/1997 | Weiner et al. | 514/44 |
| 5,650,306 A | * 7/1997 | Nabel et al. | 435/172.3 |
| 5,686,281 A | 11/1997 | Roberts | 435/172.3 |

FOREIGN PATENT DOCUMENTS

| | | |
|---|---|---|
| AU | A 59676/86 | 12/1986 |
| EP | 0 206 939 | 12/1986 |
| EP | 0 405 867 A1 | 1/1991 |
| JP | A 61 052 286 | 3/1986 |
| WO | WO 87/00054 | 1/1987 |
| WO | WO 90/10059 | 9/1990 |
| WO | WO 90/13629 | 11/1990 |
| WO | WO 91/05037 | 4/1991 |
| WO | WO 93/09239 | 5/1993 |
| WO | WO 93/15201 | 8/1993 |
| WO | WO 93/24641 | 12/1993 |
| WO | WO 95/07995 | 3/1995 |

OTHER PUBLICATIONS

Ledley et al. (Sep. 1995) Hum. Gene Therap., vol. 6, 1129–1144.*
Herrmann et al. (1995) J. Mol. Med., vol. 73, 157–163.*
Orkin et al. (1995) "Report and Recommendations of the Panel to Assess the NIH Investment in Research on Gene Therapy".*
Restifo et al. (1993) J. Immunother., vol. 14, 182–190.*
Alters et al,. "Characterization and Gene Modification of Dendritic Cells to be Used for Antigen Presentation," Keystone Symposia on Dendritic Cells, Abstract (1995).
Rosenberg, S.A., "Immunotherapy of cancer using interleukin 2: current status and future prospects," *Immunol. today*, 9(2), 58–62 (Feb., 1988).
Schmidt–Wolf and Schmidt–Wolf, "Cytokines and gene therapy," *Immunol. Today*, 16(4), 173–175 (1995).
Vieweg and Gilboa, "Considerations for the use of cytokine–secreting tumor cell preparations for cancer," *Cancer Invest.*, 13(2), 193–201 (1995).
Schmirrmacher, V., "Tumor vaccine design: concepts, mechanisms and efficacy testing," *Int. Arch. Allergy Immunol.*, 108(4), 340–344 (1995).

(List continued on next page.)

Primary Examiner—Anne M. Wehbé
(74) Attorney, Agent, or Firm—Synnestvedt & Lechner LLP

(57) ABSTRACT

A composition for genetic manipulation of cells comprises a liposome comprised of lipid material, and adeno-associated viral (AAV) material. Typically, the AAV material is plasmid, and comprises one or more terminal repeats of the AAV genome. Methods are disclosed for introducing DNA into cells using AAV/liposome complexes. The DNA is introduced and expressed in'stem cells, T cells, primary tumor cells, tumor cell lines and dendritic cells or other antigen-presenting cells. Such transfected cells are used in therapeutic methods to treat subjects with cancer or microbial infections. Dendritic cells with DNA encoding tumor or viral antigens and are used to treat subjects with tumors or viral infections by administration in vivo or by activation of antigen-specific lymphocytes ex vivo followed by administration of those lymphocytes to the subject.

27 Claims, 48 Drawing Sheets

OTHER PUBLICATIONS

Lotze et al., "Interleukin–2: developing additional cytokine gene therapies using fibroblasts or dendritic cells to enhance tumor immunity," *Cancer J. Sci. Am.*, 6 Suppl 1S61–6 (Feb., 2000).

Stingl et al., "Dendritic cells: a major story unfolds," *Immunol. today*, 16, 330–333 (1995).

Grabbe et al., "Dendritic cells as initiators of tumor immune responses: a possible strategy for tumor immunotherapy?" *Immunol. Today*, 16(3), 117–21 (1995).

King et al., "Mechanisms of dendritic cell function," *Immunol. today*, 11(6), 206–211d (1990).

Steinmann et al., "Lymphoid dendritic cells are potent stimulators of the primary mixed leukocyte reaction in mice," *Proc. Natl. Acad. Sci. USA*, 75, 5132–5136 (1975).

Macatonia et al., "Primary stimulation by dendritic cells induces antiviral proliferative and cytotoxic T cell responses in vitro," *J. Exp. Med.*, 169, 1255–1264 (1989).

Freudenthal et al., "The distinct surface of human blood dendritic cells, as observed after an improved isolation method," *Proc. Natl. Acad. Sci. USA*, 87, 7698–7702 (1990).

Thomas et al., "Isolation and characterization of human peripheral blood dendritic cells," *J. Immunol.*, 150(3), 821–834 (1993).

Mehta–Damani et al., "Generation of antigen–specific CD8+ CTLs from naive precursors," *J. Immunol.*, 153(3), 996–1003 (1994).

Inaba et al., "Identification of proliferating dendritic cell precursors in mouse blood," *J. Exp. Med.*, 175, 1157–1167 (1992).

Inaba et al., "Generation of large numbers of dendritic cells from mouse blood marrow cultures supplemented with granulocyte/macrophage colony–stimulating factor," *J. Exp. Med.*, 176, 1693–1702 (1992).

Sallusto and Lanzavecchia, "Efficient presentation of soluble antigen by cultured human dendritic cells is maintained by granulocyte/macrophage colony–stimulating factor plus interleukin 4 and downregulated by tumor necrosis factor α," *J. Exp. Med.*, 179, 1109–1118 (1994).

Takahashi et al., "Induction of CD8+ cytotoxic T lymphocytes by immunization with syngeneic irradiated HIV–1 envelope derived peptide–pulsed dendritic cells," *Inter. Immunol*, 5(8), 849–857 (1992).

Porgador and Gilboa, "Bone–marrow–generated dendritic cells pulsed with a class 1–restricted peptide are potent induces of cytotoxic T lymphocytes," *J. Exp. Med.*, 182, 255–260 (1995).

Ossevoort et al., "Dendritic cells as carriers for a cytotoxic T–lumphocyte epitope–based peptide vaccine in protection against a human papillomavirus type 16–induced tumor," *J. Immunother.*, 18(2), 86–94 (1995).

Majordomo et al., "Bone marrow–derived dendritic cells pulsed with synthetic tumor peptides elicit protective and therapeutic antitumor immunity," *Nat. Med.*, 1(12), 1297–1302 (1995).

Bakker et al., "Generation of antimelanoma cytotoxic T lymphocytes from healthy donors after presentation of melanoma–associated antigen–derived epitopes by dendritic cells in vitro," *Can. Res.*, 55, 5330–5334 (1995).

Bernhard et al., "Generation of immunostimulatory dendritic cells from human CD34+ hematopoietic progenitor cells of the bone marrow and peripheral blood," *Can. Res.*, 55, 1099–1104 (1995).

Hsu et al., "Vaccination of patients with B–cell lymphoma using autologous antigenpulsed dendritic cells," *Nature Med.*, 2(1), 52–57 (1996).

Alijagie et al., "Dendritic cells generated from peripheral blood transfected with human tyrosinase induce specific T cell activation," *Eur. J. Immunol.*, 25, 3100–3107 (1995).

Arthur et al., "A comparision of gene transfer methods in human dendritic cells," *Can. Gene Therapy*, 2(4), Abstract #P–13 (1995).

McArthur and Mulligan, "Induction of protective anti–tumor immunity in vivo by gene modified dendritic cells," *1995 SBT*, Abstract #7, 8 (1995).

Tahara et al., "IL–12 gene therapy using direct injection of tumors with genetically engineered autologous fibroblasts," *Hum. Gene Ther.*, 6(12), 1607–1624 (1995).

Verbik and Joshi, "Immune cells and cytokines: Their role in cancer immunotherapy," *Int. J. Oncol.*, 7(2), 205–223 (1995).

Uckert and Walther, "Retrovirus–mediated gene transfer in cancer therapy," *Pharmacol. Ther.*, 63(3), 323–347 (1994).

Weinstat–Saslow and Steeg, "Angiogenesis and colonization in the tumor metastatic process: Basic and applied advances," *Faseb J.*, 8(6), 401–407 (1994).

Pardoll, D.M., "Paracrine cytokine adjuvants in cancer immunotherapy," *Annu. Rev. Immunol.*, 13, 399–415 (1995).

Shen et al., "Bio–immunotherapy for cancer in experimental studies and clinical application: Current status and future challenges," *In Vivo*, 8(5), 643–652 (1994).

Porgador et al., "Immunotherapy of tumor metastasis via gene therapy," *Nat. Immun.*, 13(2–3), 113–130 (1994).

Gilboa et al., "Immunotherapy of cancer using cytokine gene–modified tumor vaccines," *Semin. Cancer Biol.*, 5(6), 409–417 (1994).

Faller, D.V. and Baltimore, D., *J. Virol.*, 49:269–272 (1984) p. 3, 1. 16–17.

Felgner, P.L. et al., *Proc. Natl. Acad. Sci. USA*, 84:7413–7417 (1987) p. 3, 1. 20–21.

Rose, J.K. et al., *Biotechniques*, 10:520–525 (1991) p. 3, 1. 25–26.

Malone, R. et al., *Proc. Natl. Acad. Sci. USA*, 86:6077–6081 p. 3, 1. 28–29.

Innes, C.L. et al., *J. Virol.*, 64:957–961 (1990) p. 3, 1. 33–34.

Philip, R. et al., *J. Biol. Chem.*, 268:16087–16090 (1993) p. 4, 1. 3–4; p. 54, 1. 20.

Shaefer–Ridder, M. et al., *Science*, 215:166–168 (1982) p. 53, 1. 20–21.

Stribling, R. et al., *Proc. Natl. Acad. Sci. USA*, 89:11277–11281 (1992) p. 54, 1. 20–21.

Zhu, N. et al., *Science*, 261: 209–211 (1993) p. 54, 1. 21–22.

Stewart, M.J. et al., *Human Gene Therapy*, 3:267–275 (1992) p. 54, 1. 22–23.

Felgner et al., *Nature*, 337:387–388 (1989).

Wang et al., *Proc. Natl. Acad. Sci.*, 84, 7851–7855 (1987).

Kotin, R.M. et al., *Proc. Natl. Acad. Sci.*, 87:2211–2215 (1990) p. 2, 1. 28–29.

Hermonat, P.L. et al., *J. Virol.*, 51:329–339 (1984) P. 3, 1. 1–2.

Graham, F.L. et al., *J. Gen. Virol.*, 36:59–72 (1977) P. 22, 1. 4.

Hermonat, P.L. and Muzyczka, N., *Proc. Natl. Acad. Sci. USA*, 81:6466–6470 (1984) p. 25, 1. 20–21; p. 25, 1. 30.

Tratschin, J.D. et al., *Mol. Cell. Biol.*, 5:3251–3260 (1985) p. 25, 1. 30–31.

Philip, R. et al., *Mol. Cell. Biol.*, 14(4):2411–2418 (1994) p. 38, 1. 35–36.
Lebkowski, J.S. et al., *Mol. Cell. Biol.*, 8:3988–3996 (1988) p. 2, 1. 21–22.
West, W.H. et al., *N. Engl. J. Med.*, 316:898 (1987) p. 4, 1. 25–26.
Topolian, S.L. et al., *J. Immunol. Methods*, 102:127–141 (1987) p. 22, 1. 13–14.
Hug et al., *Biochem. Biophys. Acta.*, 1097:1–17 (1991).
Marshall, *Science*, 269:1050–1055 (1995).
Hodgson, *Exp. Opin. Ther. Pat.*, 5(5):459–468 (1995).
Miller et al., *F.A.S.E.B.*, 9:190–199 (1995).
Culver et al., *T.I.G.*, 10(5:174–178 (1994).
Rosenberg et al., *Annals Surg.*, 218(4):455–464 (1993).
Gutierrez et al., *Lancet*, 339:715–721 (1992).
Oken, *Am. J. Clin. Oncol. (CCT)*, 5:649–655 (1982) p. 4, 1. 19–20.
Rosenberg, S., *Cancer Res.*, (Suppl.) 51, 5074s–5079s (1991).
Crystal, R., *Science*, 270, 404–410 (1995).
Mulligan, R., *Science*, 260, 926–930 (1993).
Coghlan et al., *New Scientist*, 14–15 (1995).
Brown, D., *The Washington Post*, A22 (Dec. 8, 1995).
Barinaga, M., *Science*, 266, 1326 (1994).
Tannock, et al., *Basic Science in Oncology*, MacGraw Hill (1992).
Collins, H., *Philadelphia Inquirer*, p. A01 (Mar. 6, 1993).
DeNoon, D.J., *IAC Newsletter*, DB Accession No. 02944476 (1995).
Kern, E.R., *Antiviral Agents and Viral Diseases of Man*, 3rd edition, G.J. Galasso et al. editors, p. 94–95 (1990).
*Sacramento Bee*, p. A22 (Feb. 26, 1994).
*Sacramento Bee*, p. B5 (Nov. 29, 1991).
Dropulic, B. et al., *Human Gene Therapy*, 5:927–939 (1994).
Pizzo, P.A. et al., *Clinical Infectious Diseases*, 19:177–196 (1994).
Tartour, E. et al., *Biomedicine and Pharmacotherapy*, 46:473–484 (1992).
Friedmann, T., *TIG*, 10(6), 210–214 (1994).
Riddell et al., *Nature Medicine*, (2), 2:216–223 (1996).
Gunzberg et al., *Mol. Med. Today*, 175:410–415 (1995).
Mastrayelo et al., *Seminars in Oncology*, (23), 1:4–21 (1996).
Gilboa, *Seminars in Oncology*, (23), 1:101–107 (1996).
Arca, *Seminars in Oncology*, (23), 1:108–117 (1996).
Cohen, J.S., *Trends in Biotechnology*, 10:87–91 (1992).
O'Doherty et al., *J. Exp. Med.*, 178, 1067–1078 (1993).
Yoshino et al., *J. Immun.*, 152:2394 (1994).
Steinman, R., *Annu. Rev. Immunol.*, 9:271–296 (1991) p. 5, 1. 13–14.
Barnd et al., *Proc. Natl. Acad. Sci. USA*, 86:7159 (1989) p. 40, 1. 13–14.
Jerome et al., *Canc. Res.*, 51:2908 (1991) p. 40, 1. 15.
Ioannides et al., *J. Immunol.*, 151:3693–3703 p. 40, 1. 15–16.
Jerome et al., *J. Immunol.*, 151:1654–1662 (1993) p. 40, 1. 17–18.
Takahashi et al., *J. Immunol.*, 153:2102–2109 (1994) p. 40, 1. 18–19.
Storkus and Lotze, *Biologic Therapy of Cancer: Principles and Practice*, Second Edition, Section 3.2, "Tumor Antigens Recognized by Immune Celle," pp. 64–77, J.B. Lippincott Co. (1995) p. 56, 1. 33–p. 57, 1. 3.
Romani et al., *J. Exp. Med.*, 180:83–93 (1994) p. 59, 1. 5–6.
Caux et al., *Nature*, 360:258–261 (1992) p. 60, 1. 29–30.
Reid et al., *J. Immunol.*, 149:2681–2688 (1992) p. 60, 1. 30–31.
Santiago–Schwarz et al., *J. Leukocyte Biol.*, 52:274 (1992) p. 60, 1. 31–32.
Caux et al., *J. Immunol.*, 155:5427–5435 (1995) p. 61, 1. 1–2.
Restifo et al., *Cancer Res.*, 55:3149–3157 (1995) p. 62, 1. 16.
Tsang et al., *J. Natl. Canc. Inst.*, 87:982–989 (1995) p. 65, 1. 17–18.
Kawakami et al., *J. Exp. Med.*, 180:347 (1994) p. 70, 1. 1–2, 7–8; p. 73, 1. 29–30.
Finn, O.J., *Biotherapy*, 4:239 (1992) p. 40, 1. 16–17.

* cited by examiner

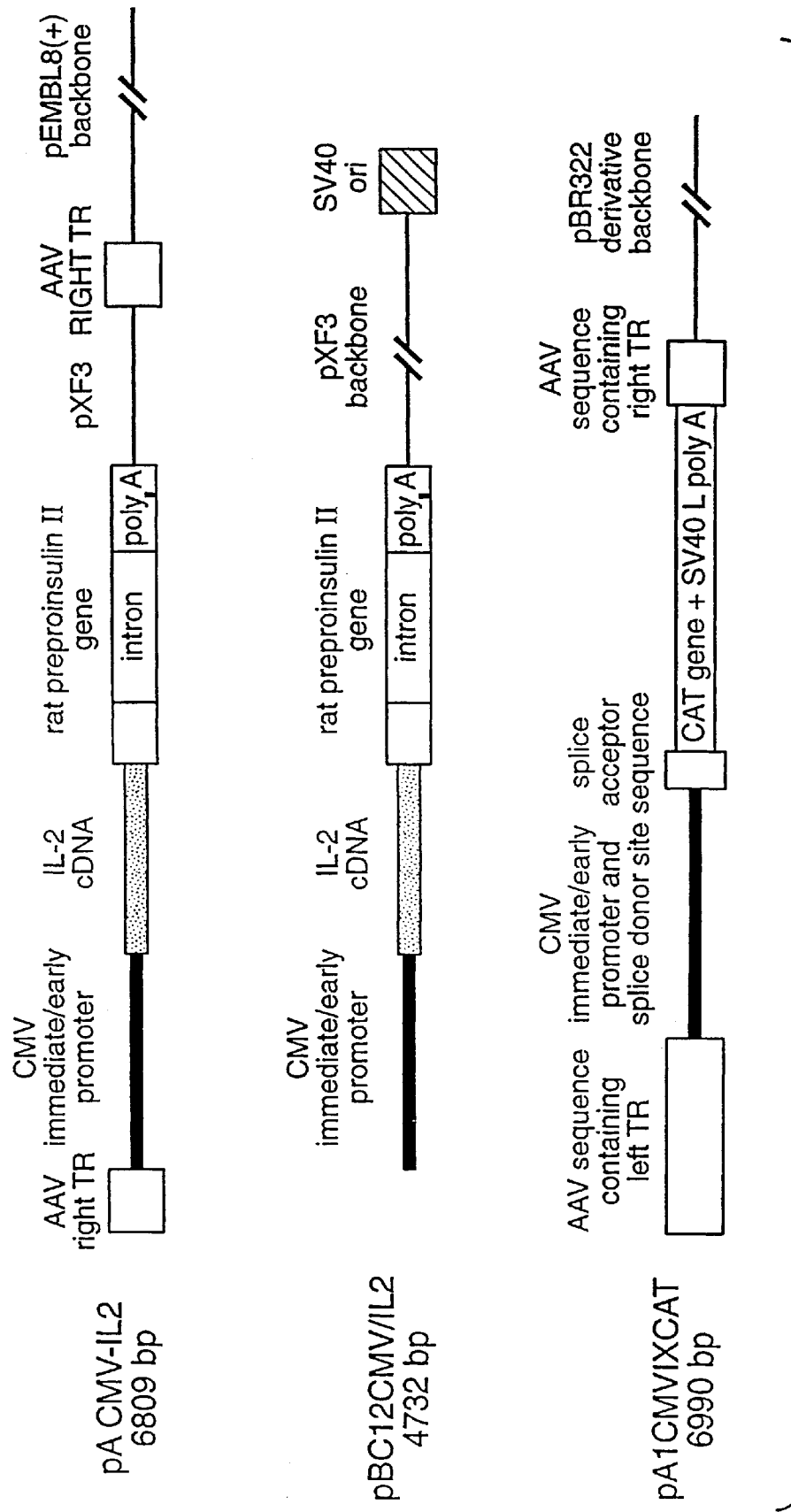
FIG._1

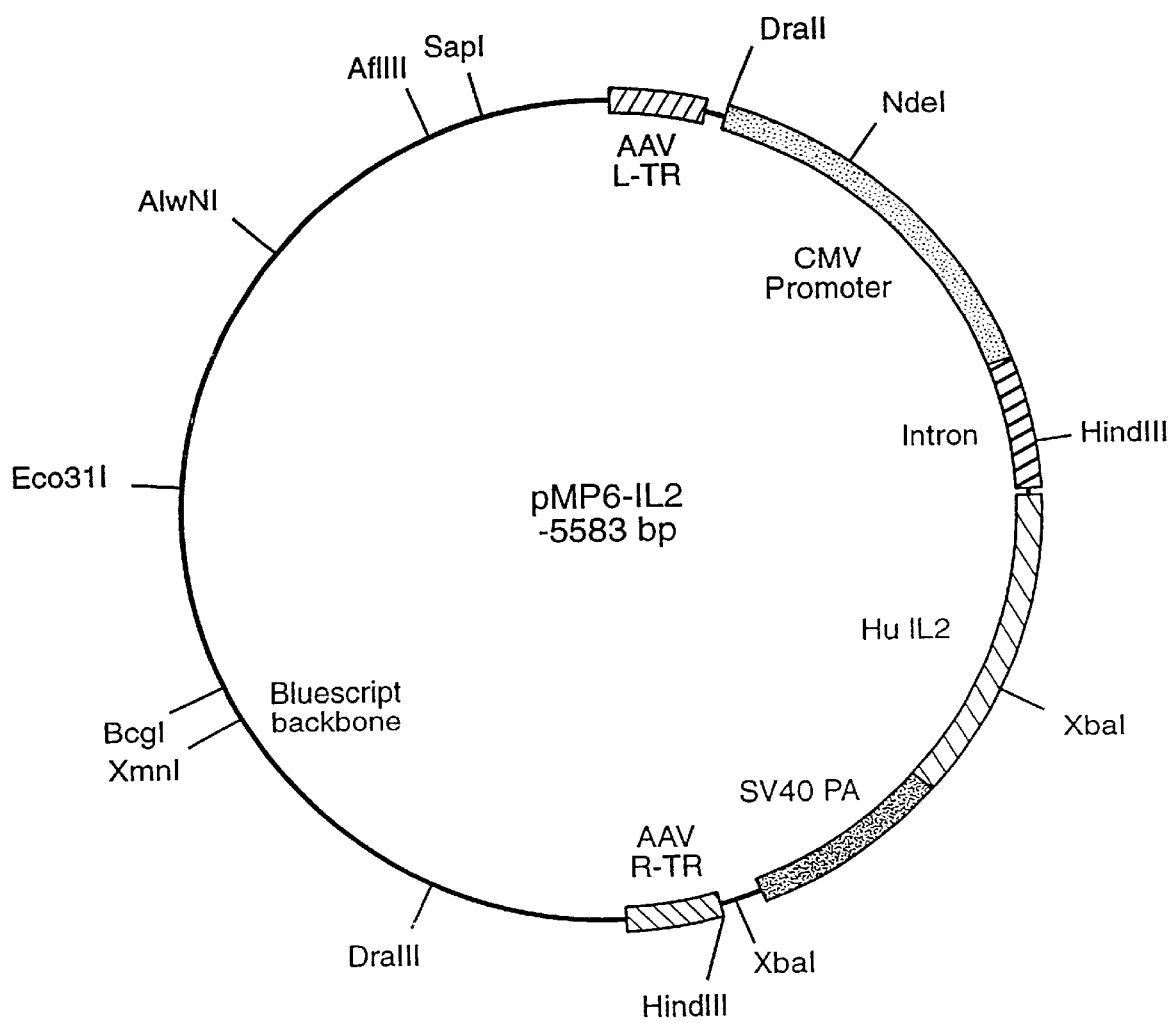
FIG._2

| | | |
|---|---|---|
| 1 | CGCGCAATTA ACCCTCACTA AAGGGAACAA AAGCTGGGTA CGATCTGGGC | 50 |
| | ◄---------- Bluescript KS II + ----------►|◄--- | |
| 51 | CACTCCCTCT CTGCGCGCTC GCTCGCTCAC TGAGGACGGG CGACCAAAGG | 100 |
| | ---------- Left terminal region of AAV ---------- | |
| 101 | TCGCCCGACG CCCGGGCTTT GCCCGGGCGG CCTCAGTGAG CGAGCGAGCG | 150 |
| 151 | CGCAGAGAGG GAGTGGCCAA CTCCATCACT AGGGGTTCCT GAGGGGTGG | 200 |
| 201 | AGTCGTGACG TGAATTACGT CATAGGGTTA GGGAGGTCCG CGCAATTAAC | 250 |
| | ---------------------------------►| | |
| 251 | CCTCACTAAA GGGAACAAAA GCTGGGTACC GGGCCCTTCG ATTCGCCCGA | 300 |
| | |◄------ | |
| 301 | CATTGATTAT TGACTAGTTA TTAATAGTAA TCAATTACGG GGTCATTAGT | 350 |
| | ---------------- CMV Promoter ---------------- | |
| 351 | TCATAGCCCA TATATGGAGT TCCGCGTTAC ATAACTTACG GTAAATGGCC | 400 |
| 401 | CGCCTGGCTG ACCGCCCAAC GACCCCCGCC CATTGACGTC AATAATGACG | 450 |
| 451 | TATGTTCCCA TAGTAACGCC AATAGGGACT TTCCATTGAC GTCAATGGGT | 500 |
| 501 | GGAGTATTTA CGGTAAACTG CCCACTTGGC AGTACATCAA GTGTATCATA | 550 |
| 551 | TGCCAAGTAC GCCCCCTATT GACGTCAATG ACGGTAAATG GCCCGCCTGG | 600 |
| 601 | CATTATGCCC AGTACATGAC CTTATGGGAC TTTCCTACTT GGCAGTACAT | 650 |
| 651 | CTACGTATTA GTCATCGCTA TTACCATGGT GATGCGGTTT TGGCAGTACA | 700 |
| 701 | TCAATGGGCG TGGATAGCGG TTTGACTCAC GGGGATTTCC AAGTCTCCAC | 750 |
| 751 | CCCATTGACG TCAATGGGAG TTTGTTTTGG CACCAAAATC AACGGGACTT | 800 |
| 801 | TCCAAAATGT CGTAACAACT CCGCCCCATT GACGCAAATG GGCGGTAGGC | 850 |
| 851 | GTGTACGGTG GGAGGTCTAT ATAAGCAGAG CTCGTTTAGT GAACCGTCAG | 900 |

FIG._3A

```
 901  ATCGCCTGGA GACGCCATCC ACGCTGTTTT GACCTCCATA GAAGACACCG   950

951  GGACCGATCC AGCCTCCGCG GCCGGGAACG GTGCATTGGA ACGCGGATTC  1000

1001  CCCGTGCCAA GAGTGACGTA AGTACCGCCT ATAGAGTCTA TAGGCCCACC  1050

1051  CCCTTGGCTT CTTATGCGAC GGATCAATTC GCTGTCTGCG AGGGCCAGCT  1100
                                    →|  |←

1101  GTTGGGGTGA GTACTCCCTC TCAAAAGCGG GCATGACTTC TGCGCTAAGA  1150
      ------- Adeno virus major late intervening sequence -------

1151  TTGTCAGTTT CCAAAAACGA GGAGGATTTG ATATTCACCT GGCCCGCGGT  1200

1201  GATGCCTTTG AGGGTGGCCG CGTCCATCTG GTCAGAAAAG ACAATCTTTT  1250

1251  TGTTGTCAAG CTTGAGGTGT GGCAGGCTTG AGATCTGGCC ATACACTTGA  1300
                  →|  |←

1301  GTGACAATGA CATCCACTTT GCCTTCTCT CCACAGGTGT CCACTCCCAG  1350
      ------- Mouse immunoglobulin intervening sequence --------

1351  GTCCAACGAT CCACTAGTTC TAGTACCAGC TGCTAGAGCT TGGTAAGTGA  1400
      -----→|                                        |← -----

1401  CCAGCTACAG TCGGAAACCA TCAGCAAGCA GGTATGTACT CTCCAGGGTG  1450
      --------- Rat preproinsulin 5' untranslated region ---------

1451  GGCCTGGCTT CCCCAGTCAA GACTCCAGGG ATTTGAGGGA CGCTGTGGGC  1500

1501  TCTTCTCTTA CATGTACCTT TTGCTAGCCT CAACCCTGAC TATCTTCCAG  1550

1      M   A   L   W   I   D   R   M   Q   L   L   S       12
1551  GTCATTGTTC CAACATGGCC CTGTGGATCG ACAGGATGCA ACTCCTGTCT  1600
      -----------→|← -- Rat Insulin -- →|   |← ----------
                  signal peptide
         13    C   I   A   L   S   L   A   L   V   T   N   S   A   P   T   S   S    29
1601  TGCATTGCAC TAAGTCTTGC ACTTGTCACA AACAGTGCAC CTACTTCAAG  1650
      ----------------- Human IL-2 -----------------
         30    S   T   K   K   T   Q   L   Q   L   E   H   L   L   L   D   L       45
1651  TTCTACAAAG AAAACACAGC TACAACTGGA GCATTTACTG CTGGATTTAC  1700

46    Q   M   I   L   N   G   I   N   N   Y   K   N   P   K   L   T   R    62
1701  AGATGATTTT GAATGGAATT AATAATTACA AGAATCCCAA ACTCACCAGG  1750

63    M   L   T   F   K   F   Y   M   P   K   K   A   T   E   L   K   H    79
1751  ATGCTCACAT TTAAGTTTTA CATGCCCAAG AAGGCCACAG AACTGAAACA  1800
```

FIG._3B

```
      80   L  Q  C   L  E  E   E  L  K  P   L  E  E   V  L  N
    1801   TCTTCAGTGT CTAGAAGAAG AACTCAAACC TCTGGAGGAA GTGCTAAATT   1850
           ---------- ---------- ---------- -------▶◀- ----
      96   L  A  Q  S   K  N  F   H  L  R   P  R  D  L   I  S  N   112
    1851   TAGCTCAAAG CAAAAACTTT CACTTAAGAC CCAGGGACTT AATCAGCAAT   1900
           ---------- ---------- Human IL-2 ---------- ----------
     113   I  N  V   I  V  L  E   L  K  G   S  E  T   T  F  M  C   129
    1901   ATCAACGTAA TAGTTCTGGA ACTAAAGGGA TCTGAAACAA CATTCATGTG   1950
           ---------- ---------- ---------- ---------- ----------
     130   E  Y  A   D  E  T   A  T  I  V   E  F  L   N  R  W      145
    1951   TGAATATGCT GATGAGACAG CAACCATTGT AGAATTTCTG AACAGATGGA   2000
           ---------- ---------- ---------- ---------- ----------
     146   I  T  F  C   Q  S  I   I  S  T   L  T  *                 158
    2001   TTACCTTTTG TCAAAGCATC ATCTCAACAC TGACTTGATA ATTAAGTGCT   2050
           ---------- ---------- ---------- ---------- ----------
```

```
    2051   TCCCACTTAA AACATATCAG GGATCGATCC AGACATGATA AGATACATTG   2100
           ---------- ---------- ------▶    ◀--------- ----------
    2101   ATGAGTTTGG ACAAACCACA ACTAGAATGC AGTGAAAAAA ATGCTTTATT   2150
           ---------- --------- SV40 Polyadenylation signal --------
    2151   TGTGAAATTT GTGATGCTAT TGCTTTATTT GTAACCATTA TAAGCTGCAA   2200
           ---------- ---------- ---------- ---------- ----------
    2201   TAAACAAGTT AACAACAACA ATTGCATTCA TTTTATGTTT CAGGTTCAGG   2250
           ---------- ---------- ---------- ---------- ----------
    2251   GGGAGGTGTG GGAGGTTTTT TAAAGCAAGT AAAACCTCTA CAAATGTGGT   2300
           ---------- ---------- ---------- ---------- ----------
    2301   ATGGCTGATT ATGATCCGGC TGCCTCGCGC GTTTCGGTGA TGACGGTGAA   2350
           ---------- ---------- ---------- ---------- ----------
    2351   AACCTCTGAC ACATGCAGCT CCCGGAGACG GTCACAGCTT GTCTGTAAGC   2400
           ---------- ---------- ---------- ---------- ----------
    2401   GGATGCCGGG AGCAGACAAG CCCGTCAGGG CGCGTCAGCG GGTGTTGGCG   2450
           ---------- ---------- ---------- ---------- ----------
    2451   GGTGTCGGGG CGCAGCCATG AGGTCGACTC TAGTAGAGCG GCCGCCACCG   2500
           ---------- ---------- ▶
    2501   CGGTGGAGCT CCAATTCGCC CTATAGTGAG TCGTATTACG CGCGTCGAGT   2550
           ---------- ---------- ---------- ---------- ----------
    2551   CTAGAGAGCT CGGGCCCAAG CTTGGTACCC ATGGCTACGT AGATAAGTAG   2600
           ---------- ---------- ---------- ◀--------- ----------
    2601   CATGGCGGGT TAATCATTAA CTACAAGGAA CCCCTAGTGA TGGAGTTGGC   2650
           ---------- ---------- Right terminal region of AAV ------
    2651   CACTCCCTCT CTGCGCGCTC GCTCGCTCAC TGAGAGACCG CGACCAAAGG   2700
           ---------- ---------- ---------- ---------- ----------
```

FIG._3C

2701 TCGCCCGACG CCCGGGCTTT GCCCGGGCGG CCTCAGTGAG CGAGCGAGCG 2750

2751 CGCAGAGAGG GACAGATCCA ATTCGCCCTA TAGTGAGTCG TATTACGCGC 2800
           ------►◄---- Bluescript KS II + ----------------

2801 GCTCACTGGC CGTCGTTTTA CAACGTCGTG ACTGGGAAAA CCCTGGCGTT 2850

2851 ACCCAACTTA ATCGCCTTGC AGCACATCCC CCTTTCGCCA GCTGGCGTAA 2900

2901 TAGCGAAGAG GCCCGCACCG ATCGCCCTTC CCAACAGTTG CGCAGCCTGA 2950

2951 ATGGCGAATG GGACGCGCCC TGTAGCGGCG CATTAAGCGC GGCGGGTGTG 3000

3001 GTGGTTACGC GCAGCGTGAC CGCTACACTT GCCAGCGCCC TAGCGCCCGC 3050

3051 TCCTTTCGCT TTCTTCCCTT CCTTTCTCGC CACGTTCGCC GGCTTTCCCC 3100

3101 GTCAAGCTCT AAATCGGGGG CTCCCTTTAG GGTTCCGATT TAGTGCTTTA 3150

3151 CGGCACCTCG ACCCCAAAAA ACTTGATTAG GGTGATGGTT CACGTAGTGG 3200

3201 GCCATCGCCC TGATAGACGG TTTTTCGCCC TTTGACGTTG GAGTCCACGT 3250

3251 TCTTTAATAG TGGACTCTTG TTCCAAACTG GAACAACACT CAACCCTATC 3300

3301 TCGGTCTATT CTTTTGATTT ATAAGGGATT TTGCCGATTT CGGCCTATTG 3350

3351 GTTAAAAAAT GAGCTGATTT AACAAAAATT TAACGCGAAT TTTAACAAAA 3400

3401 TATTAACGCT TACAATTTAG GTGGCACTTT TCGGGGAAAT GTGCGCGGAA 3450

3451 CCCCTATTTG TTTATTTTTC TAAATACATT CAAATATGTA TCCGCTCATG 3500

3501 AGACAATAAC CCTGATAAAT GCTTCAATAA TATTGAAAAA GGAAGAGTAT 3550

3551 GAGTATTCAA CATTTCCGTG TCGCCCTTAT TCCCTTTTTT GCGGCATTTT 3600

FIG._3D

```
3601  GCCTTCCTGT TTTTGCTCAC CCAGAAACGC TGGTGAAAGT AAAAGATGCT  3650

3651  GAAGATCAGT TGGGTGCACG AGTGGGTTAC ATCGAACTGG ATCTCAACAG  3700

3701  CGGTAAGATC CTTGAGAGTT TTCGCCCCGA AGAACGTTTT CCAATGATGA  3750

3751  GCACTTTTAA AGTTCTGCTA TGTGGCGCGG TATTATCCCG TATTGACGCC  3800

3801  GGGCAAGAGC AACTCGGTCG CCGCATACAC TATTCTCAGA ATGACTTGGT  3850

3851  TGAGTACTCA CCAGTCACAG AAAAGCATCT TACGGATGGC ATGACAGTAA  3900

3901  GAGAATTATG CAGTGCTGCC ATAACCATGA GTGATAACAC TGCGGCCAAC  3950

3951  TTACTTCTGA CAACGATCGG AGGACCGAAG GAGCTAACCG CTTTTTTGCA  4000

4001  CAACATGGGG GATCATGTAA CTCGCCTTGA TCGTTGGGAA CCGGAGCTGA  4050

4051  ATGAAGCCAT ACCAAACGAC GAGCGTGACA CCACGATGCC TGTAGCAATG  4100

4101  GCAACAACGT TGCGCAAACT ATTAACTGGC GAACTACTTA CTCTAGCTTC  4150

4151  CCGGCAACAA TTAATAGACT GGATGGAGGC GGATAAAGTT GCAGGACCAC  4200

4201  TTCTGCGCTC GGCCCTTCCG GCTGGCTGGT TTATTGCTGA TAAATCTGGA  4250

4251  GCCGGTGAGC GTGGGTCTCG CGGTATCATT GCAGCACTGG GGCCAGATGG  4300

4301  TAAGCCCTCC CGTATCGTAG TTATCTACAC GACGGGGAGT CAGGCAACTA  4350

4351  TGGATGAACG AAATAGACAG ATCGCTGAGA TAGGTGCCTC ACTGATTAAG  4400

4401  CATTGGTAAC TGTCAGACCA AGTTTACTCA TATATACTTT AGATTGATTT  4450

4451  AAAACTTCAT TTTTAATTTA AAAGGATCTA GGTGAAGATC CTTTTTGATA  4500
```

FIG._3E

```
4501  ATCTCATGAC CAAAATCCCT TAACGTGAGT TTTCGTTCCA CTGAGCGTCA  4550

4551  GACCCCGTAG AAAAGATCAA AGGATCTTCT TGAGATCCTT TTTTTCTGCG  4600

4601  CGTAATCTGC TGCTTGCAAA CAAAAAAACC ACCGCTACCA GCGGTGGTTT  4650

4651  GTTTGCCGGA TCAAGAGCTA CCAACTCTTT TTCCGAAGGT AACTGGCTTC  4700

4701  AGCAGAGCGC AGATACCAAA TACTGTCCTT CTAGTGTAGC CGTAGTTAGG  4750

4751  CCACCACTTC AAGAACTCTG TAGCACCGCC TACATACCTC GCTCTGCTAA  4800

4801  TCCTGTTACC AGTGGCTGCT GCCAGTGGCG ATAAGTCGTG TCTTACCGGG  4850

4851  TTGGACTCAA GACGATAGTT ACCGGATAAG GCGCAGCGGT CGGGCTGAAC  4900

4901  GGGGGGTTCG TGCACACAGC CCAGCTTGGA GCGAACGACC TACACCGAAC  4950

4951  TGAGATACCT ACAGCGTGAG CTATGAGAAA GCGCCACGCT TCCCGAAGGG  5000

5001  AGAAAGGCGG ACAGGTATCC GGTAAGCGGC AGGGTCGGAA CAGGAGAGCG  5050

5051  CACGAGGGAG CTTCCAGGGG GAAACGCCTG GTATCTTTAT AGTCCTGTCG  5100

5101  GGTTTCGCCA CCTCTGACTT GAGCGTCGAT TTTTGTGATG CTCGTCAGGG  5150

5151  GGGCGGAGCC TATGGAAAAA CGCCAGCAAC GCGGCCTTTT TACGGTTCCT  5200

5201  GGCCTTTTGC TGGCCTTTTG CTCACATGTT CTTTCCTGCG TTATCCCCTG  5250

5251  ATTCTGTGGA TAACCGTATT ACCGCCTTTG AGTGAGCTGA TACCGCTCGC  5300

5301  CGCAGCCGAA CGACCGAGCG CAGCGAGTCA GTGAGCGAGG AAGCGGAAGA  5350

5351  GCGCCCAATA CGCAAACCGC CTCTCCCCGC GCGTTGGCCG ATTCATTAAT  5400
```

FIG._3F

5401 GCAGCTGGCA CGACAGGTTT CCCGACTGGA AAGCGGGCAG TGAGCGCAAC 5450

5451 GCAATTAATG TGAGTTAGCT CACTCATTAG GCACCCCAGG CTTTACACTT 5500

5501 TATGCTTCCG GCTCGTATGT TGTGTGGAAT TGTGAGCGGA TAACAATTTC 5550
              Bluescript KS II +

5551 ACACAGGAAA CAGCTATGAC CATGATTACG CCAAG 5585

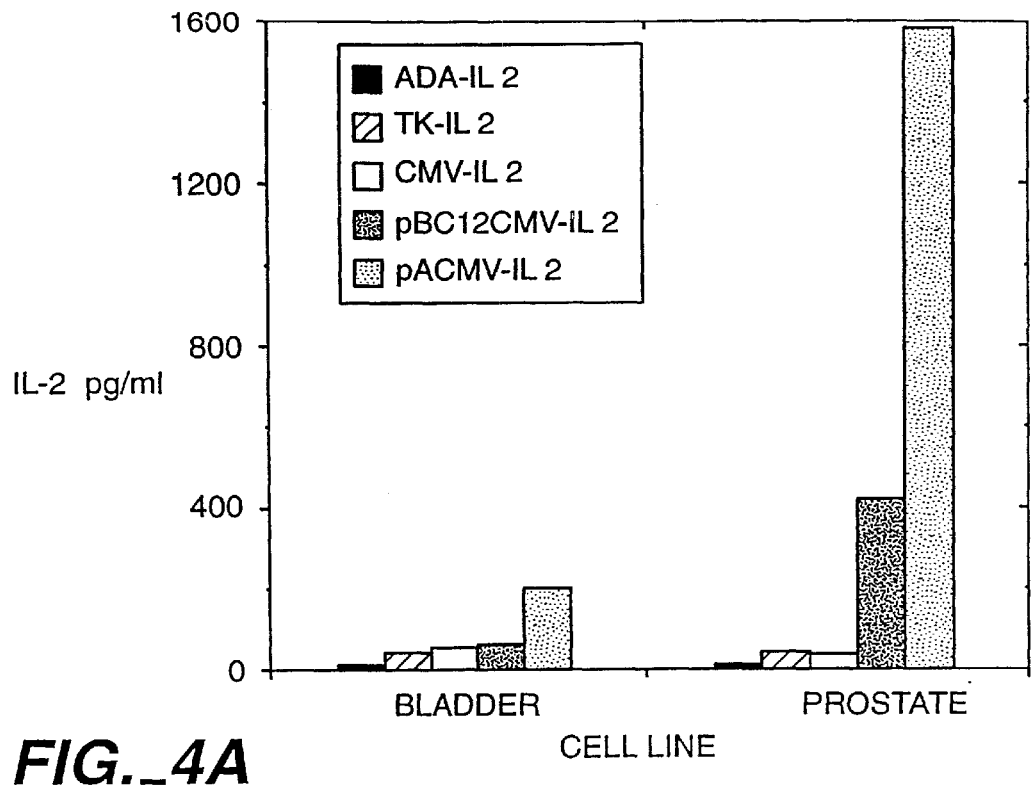
*FIG._4A*
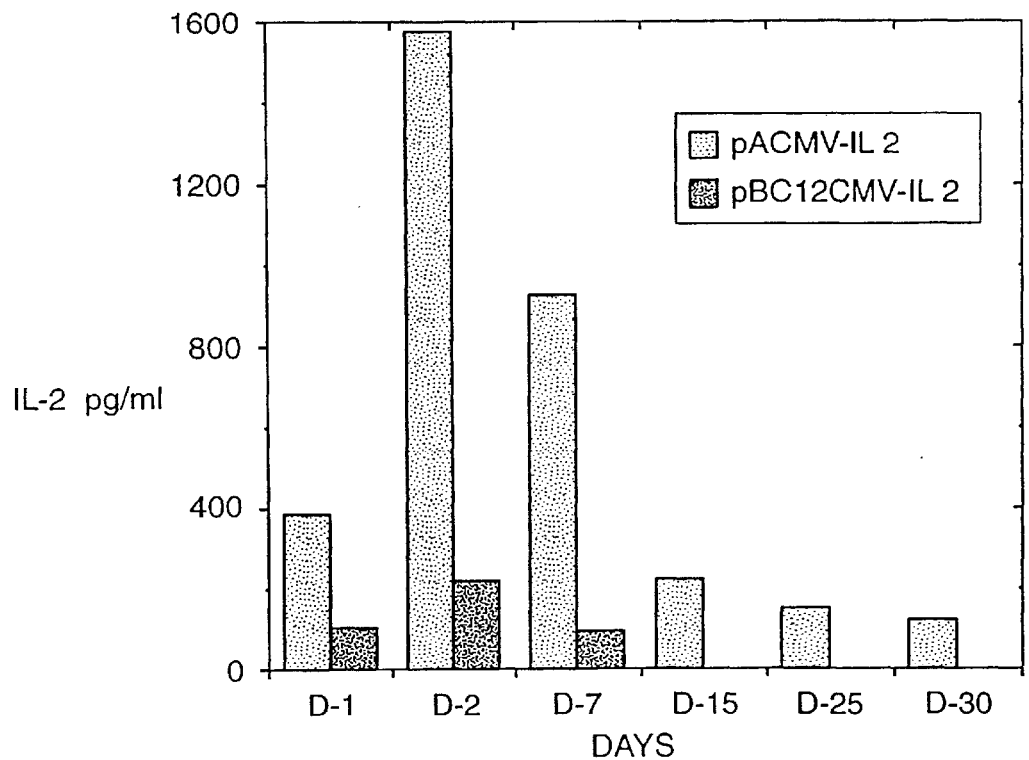
*FIG._4B*

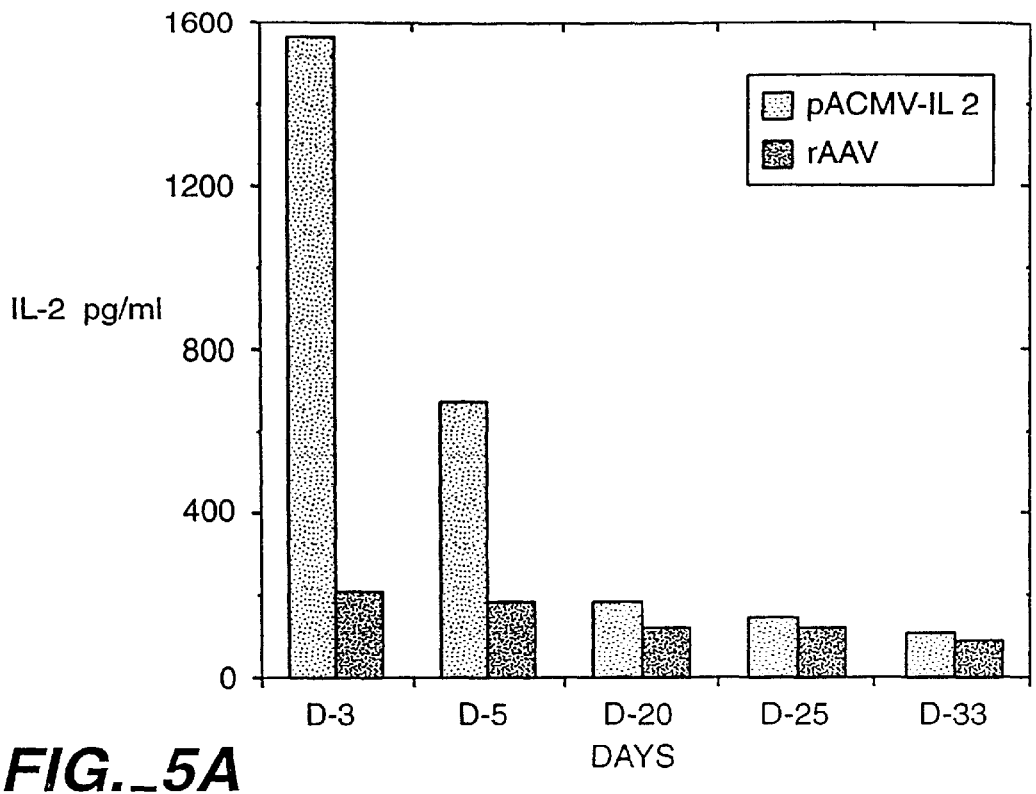
FIG._5A
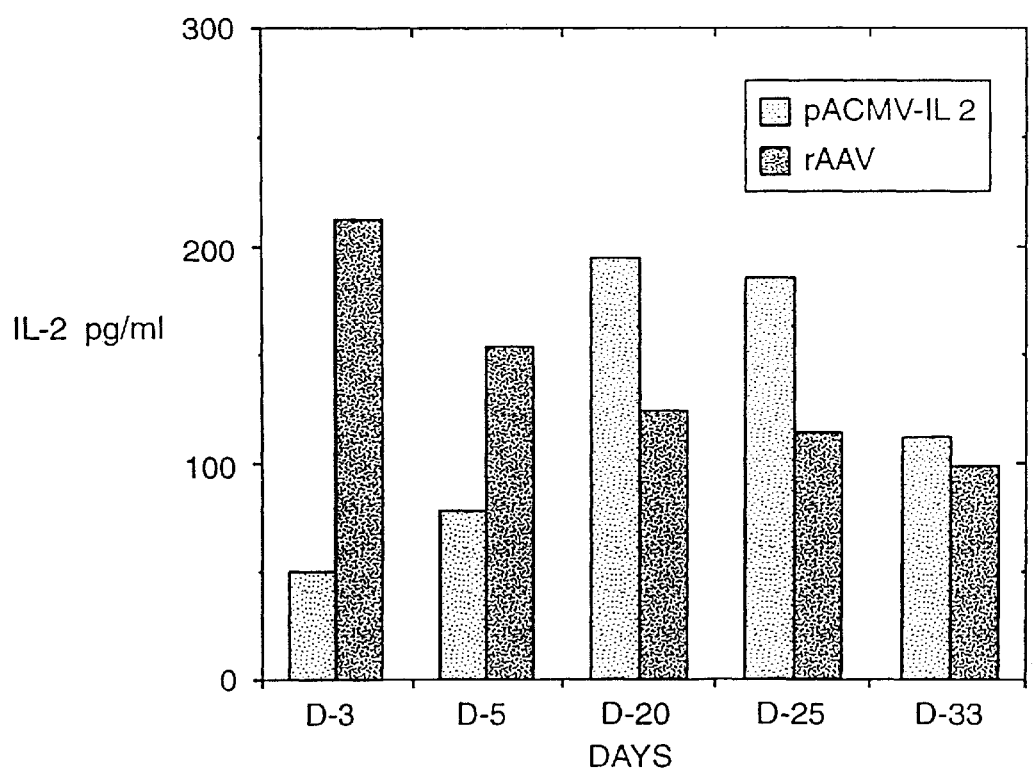
FIG._5B

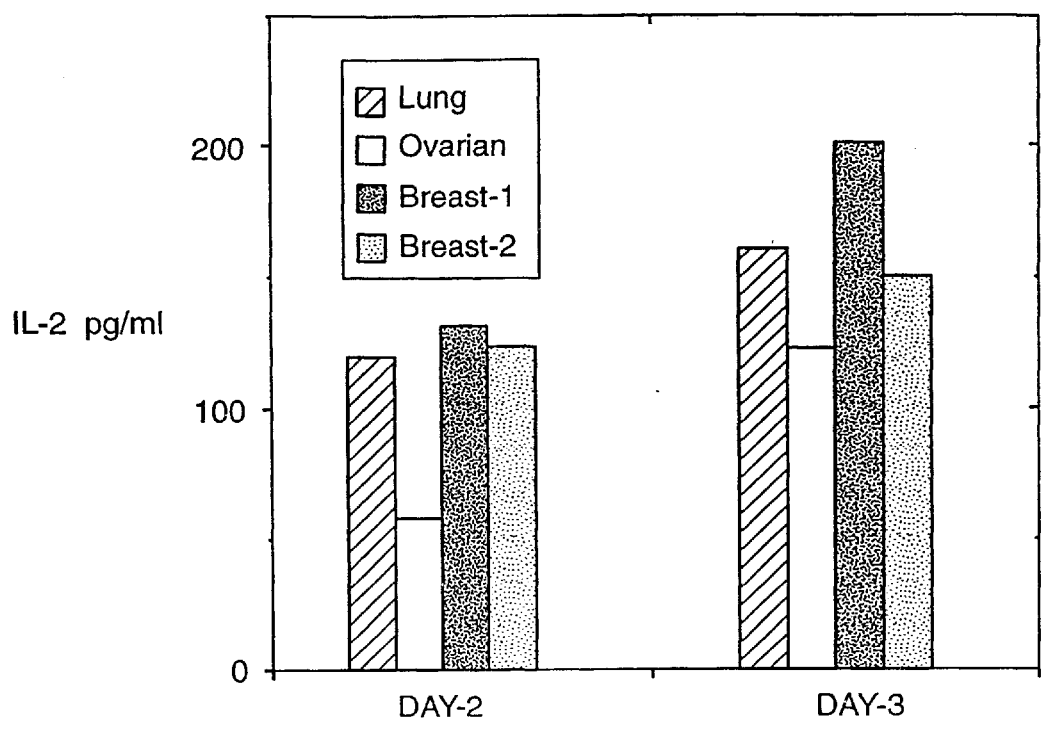
FIG._6
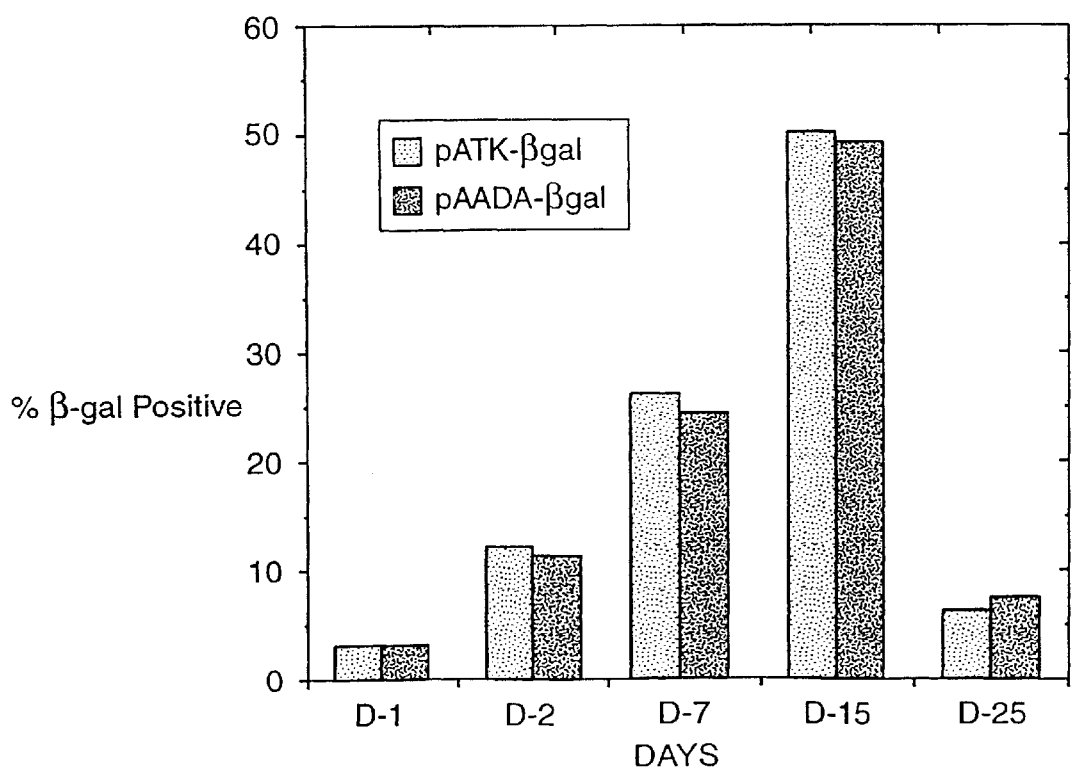
FIG._8

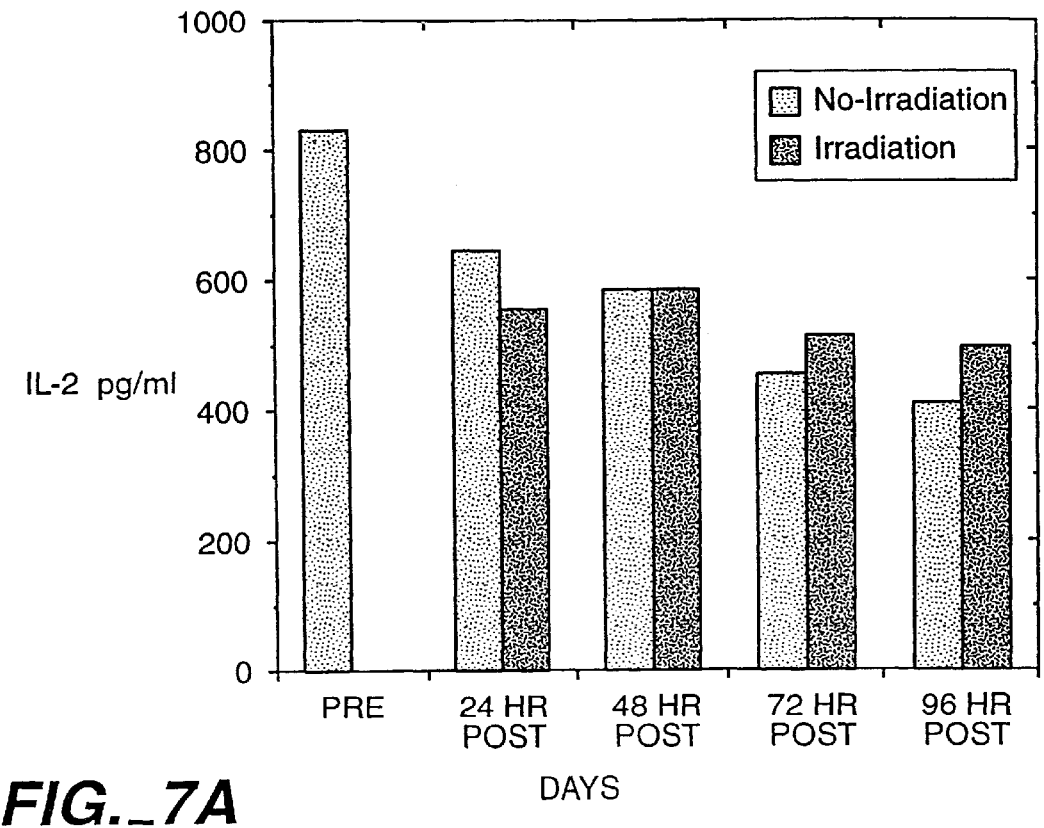
FIG._7A
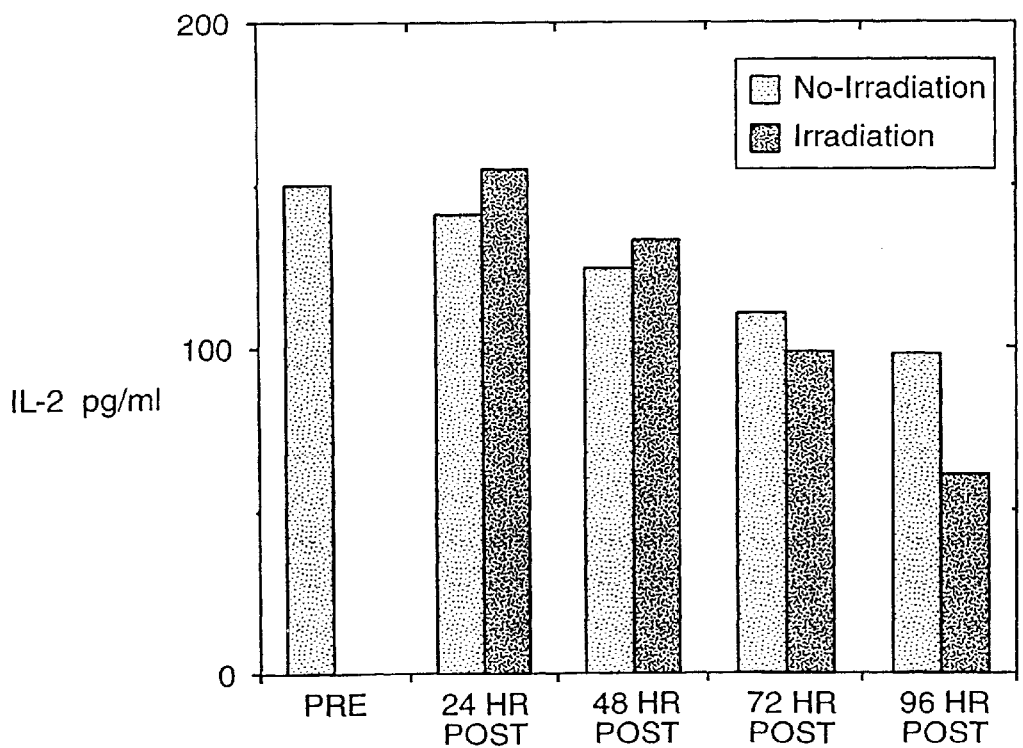
FIG._7B

A1 A2 A3 A4 ⊖ d2

① 10 µg PACMVIXCAT + 10 nmole D as D:D 1:1
② 10 µg PACMVIXCAT + 20 nmole D as D:D 1:1
③ 10 µg PACMVIXCAT + 10 nmole D as D:C 1:1
④ 10 µg PACMVIXCAT + 20 nmole D as D:C 1:1

A1  A2  A3  A4  B1  B2  B3  B4  —

CD 5/8

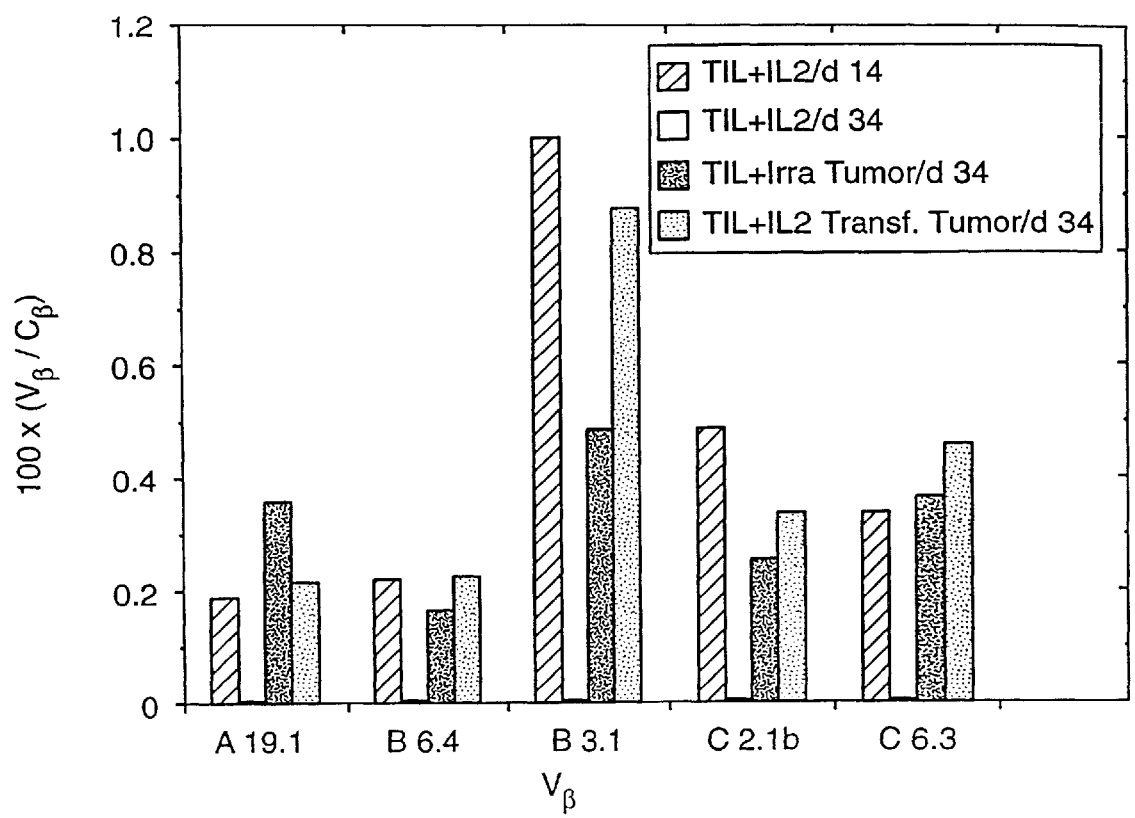
FIG._13

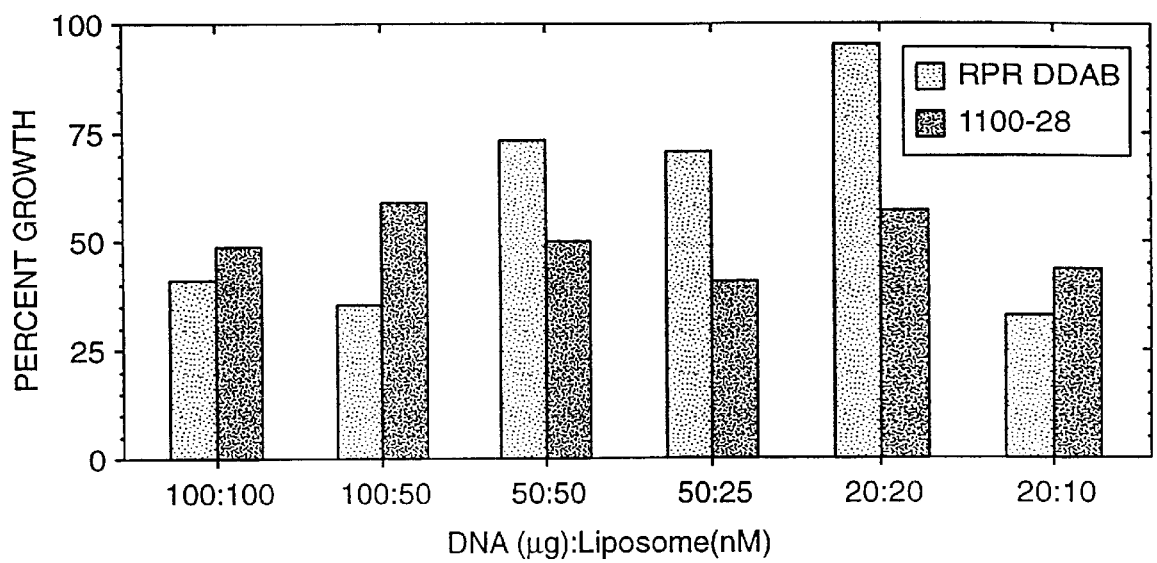
FIG._14
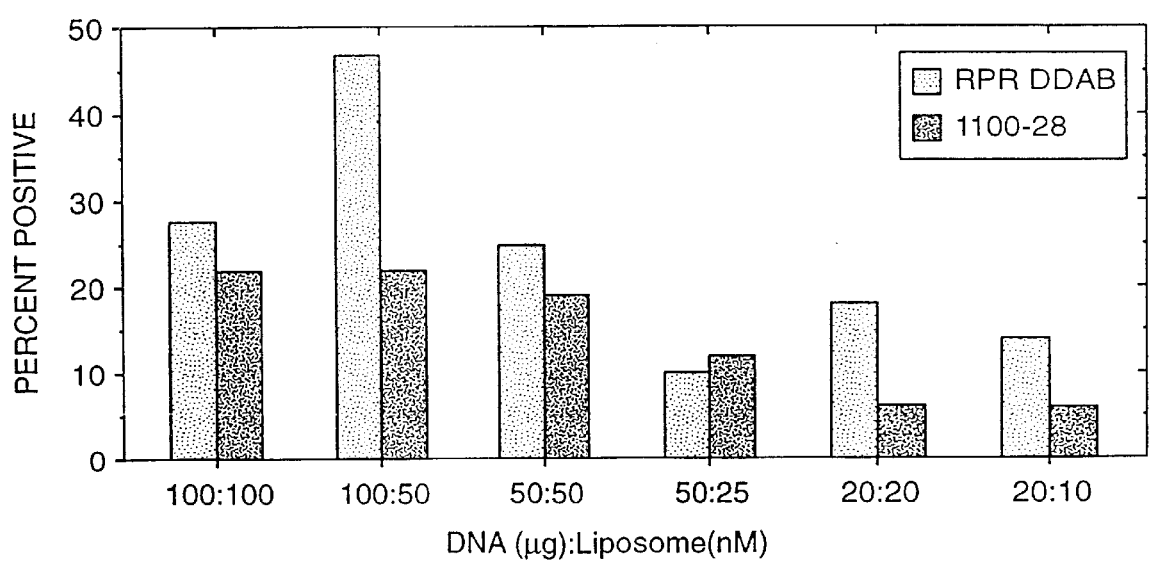
FIG._15

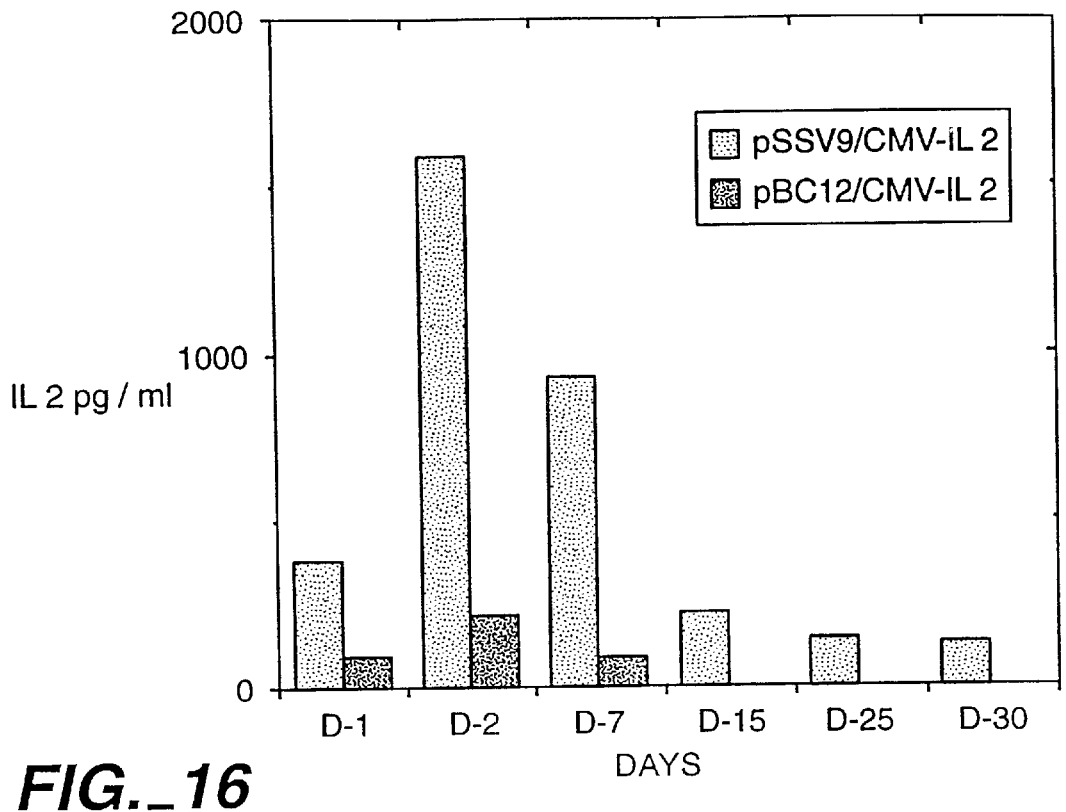
FIG._16
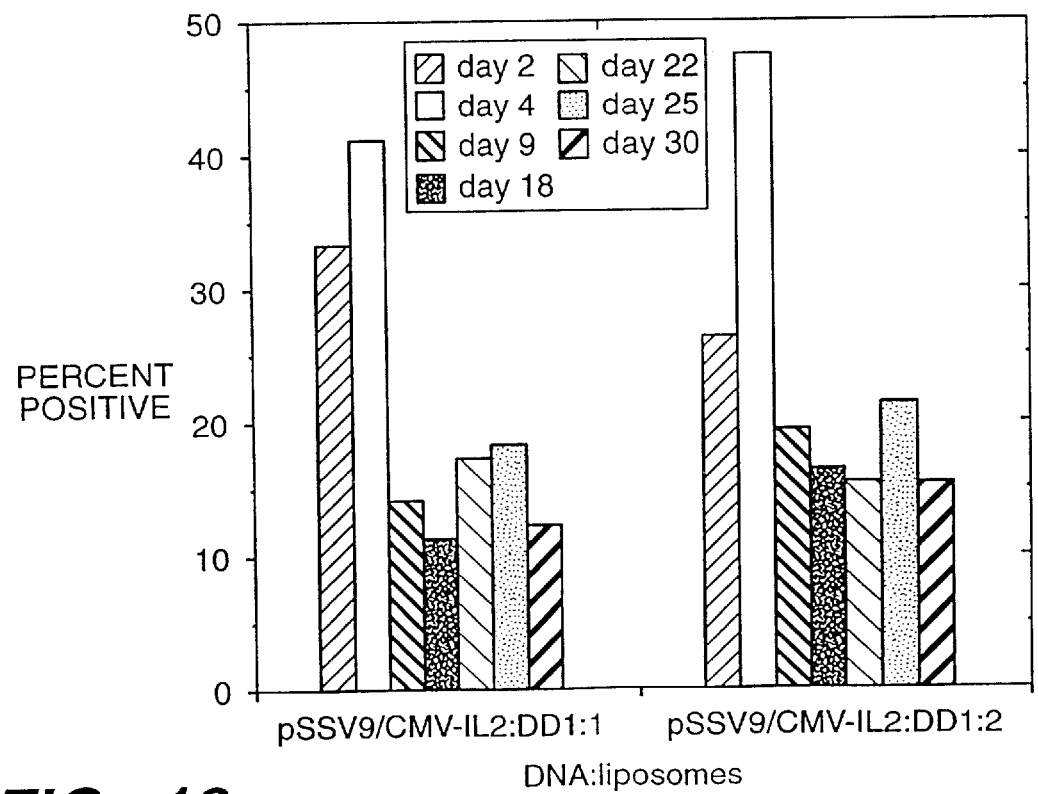
FIG._18

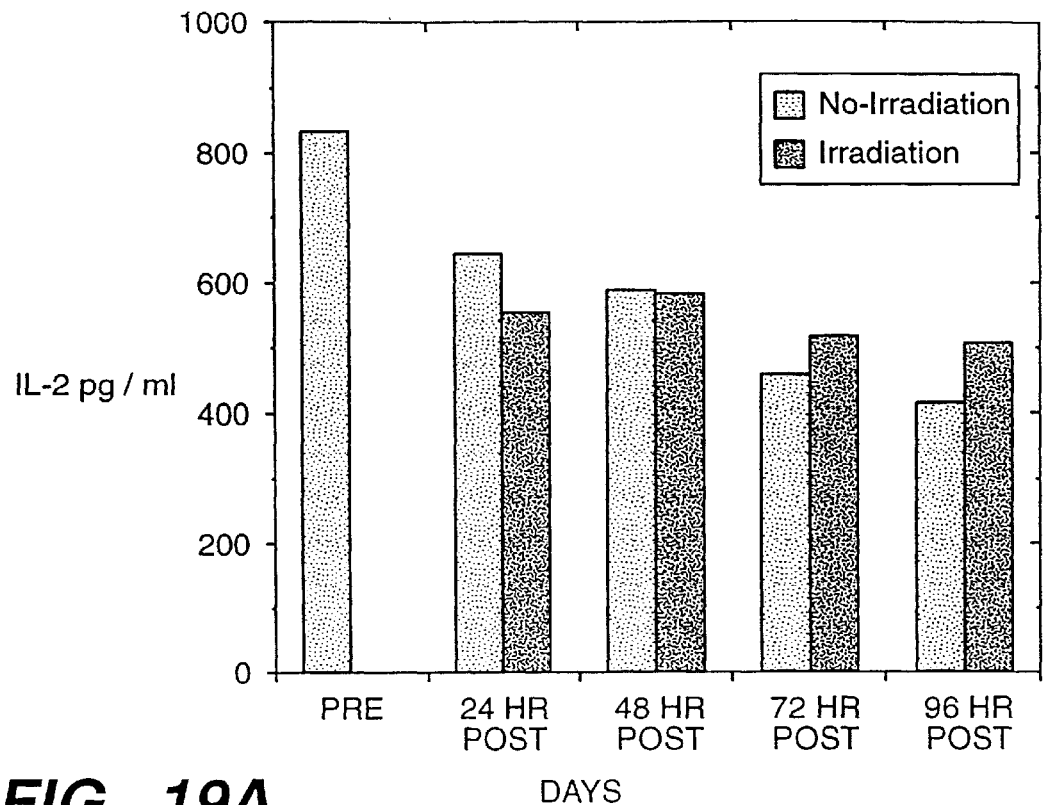
FIG._19A
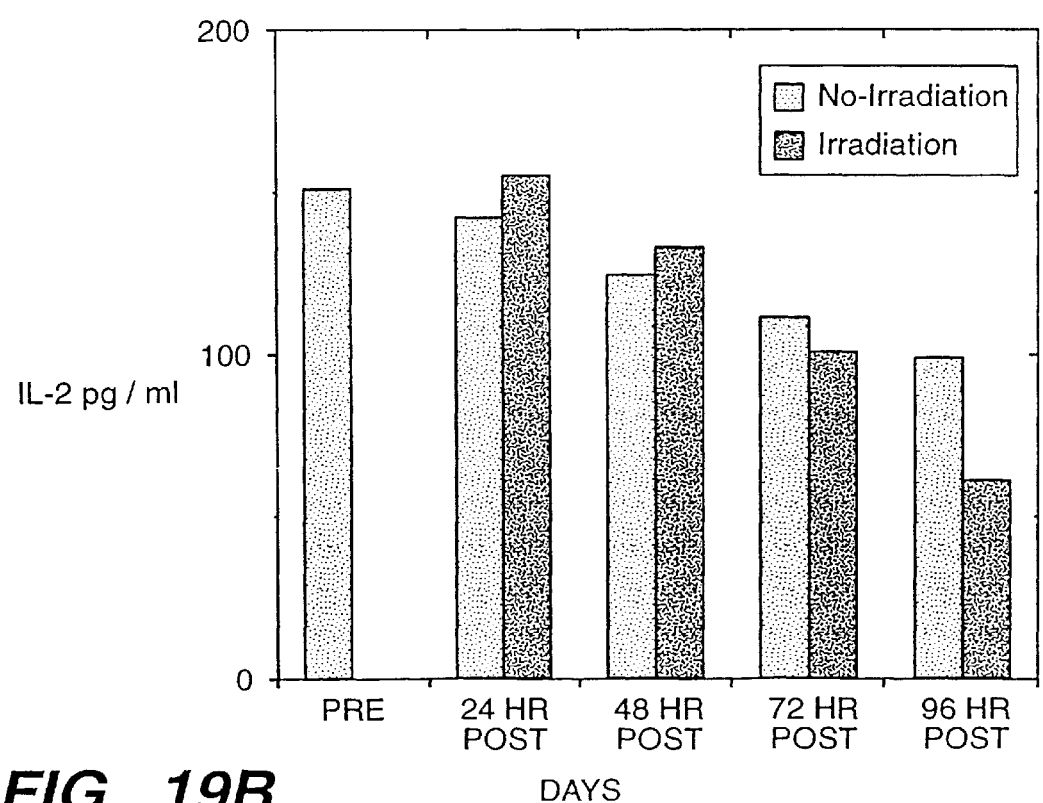
FIG._19B

SEQUENCE LISTING (1) GENERAL INFORMATION:

(iii) NUMBER OF SEQUENCES: 30

(2) INFORMATION FOR SEQ ID NO: 1:

(i) SEQUENCE CHARACTERISTICS:
        (A) LENGTH: 5585 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 1565..2035
        (D) OTHER INFORMATION: /product= "Residues 1565 to 1579 rat
            insulin signal peptide; residues 1580 to 1582 linker;
            residues 1583 to 2035 human IL-2"

(ix) FEATURE:
        (A) NAME/KEY: misc_feature
        (B) LOCATION: 1..44
        (D) OTHER INFORMATION: /product= "Bluescript KS II +
            cloning vector"

(ix) FEATURE:
        (A) NAME/KEY: LTR
        (B) LOCATION: 45..239
        (D) OTHER INFORMATION: /function= "Left terminal region of
            adeno-associated virus"

(ix) FEATURE:
        (A) NAME/KEY: promoter
        (B) LOCATION: 293..1075
        (D) OTHER INFORMATION: /function= "CMV promoter"

(ix) FEATURE:
        (A) NAME/KEY: iDNA
        (B) LOCATION: 1079..1264
        (D) OTHER INFORMATION: /function= "Adeno virus major late
            intervening sequence"

(ix) FEATURE:
        (A) NAME/KEY: iDNA
        (B) LOCATION: 1269..1357

(D) OTHER INFORMATION: /function= "Mouse immunoglobulin
    intervening sequence"

(ix) FEATURE:
    (A) NAME/KEY: 5'UTR
    (B) LOCATION: 1394..1564
    (D) OTHER INFORMATION: /function= "Rat preproinsulin 5'
        untranslated region"

(ix) FEATURE:
    (A) NAME/KEY: polyA_site
    (B) LOCATION: 2085..2471
    (D) OTHER INFORMATION: /standard_name= "SV40
        polyadenylation signal"

(ix) FEATURE:
    (A) NAME/KEY: LTR
    (B) LOCATION: 2579..2762
    (D) OTHER INFORMATION: /function= "right terminal region
        of adeno-associated virus"

(ix) FEATURE:
    (A) NAME/KEY: misc_feature
    (B) LOCATION: 2763..5585
    (D) OTHER INFORMATION: /product= "Bluescript KS II +
        cloning vector"

(ix) FEATURE:
    (A) NAME/KEY: 3'UTR
    (B) LOCATION: 2039..2071
    (D) OTHER INFORMATION: /function= "3' untranslated region
        of human IL-2"

(xi) SEQUENCE DESCRIPTION: SEQ ID NO: 1:

```
CGCGCAATTA ACCCTCACTA AAGGGAACAA AAGCTGGGTA CGATCTGGGC CACTCCCTCT    60

CTGCGCGCTC GCTCGCTCAC TGAGGACGGG CGACCAAAGG TCGCCCGACG CCCGGGCTTT   120

GCCCGGGCGG CCTCAGTGAG CGAGCGAGCG CGCAGAGAGG GAGTGGCCAA CTCCATCACT   180

AGGGGTTCCT GGAGGGGTGG AGTCGTGACG TGAATTACGT CATAGGGTTA GGGAGGTCCG   240

CGCAATTAAC CCTCACTAAA GGGAACAAAA GCTGGGTACC GGGCCCTTCG ATTCGCCCGA   300

CATTGATTAT TGACTAGTTA TTAATAGTAA TCAATTACGG GGTCATTAGT TCATAGCCCA   360

TATATGGAGT TCCGCGTTAC ATAACTTACG GTAAATGGCC CGCCTGGCTG ACCGCCCAAC   420

GACCCCCGCC CATTGACGTC AATAATGACG TATGTTCCCA TAGTAACGCC AATAGGGACT   480

TTCCATTGAC GTCAATGGGT GGAGTATTTA CGGTAAACTG CCCACTTGGC AGTACATCAA   540

GTGTATCATA TGCCAAGTAC GCCCCCTATT GACGTCAATG ACGGTAAATG GCCCGCCTGG   600

CATTATGCCC AGTACATGAC CTTATGGGAC TTTCCTACTT GGCAGTACAT CTACGTATTA   660

GTCATCGCTA TTACCATGGT GATGCGGTTT TGGCAGTACA TCAATGGGCG TGGATAGCGG   720

TTTGACTCAC GGGGATTTCC AAGTCTCCAC CCCATTGACG TCAATGGGAG TTTGTTTTGG   780

CACCAAAATC AACGGGACTT TCCAAAATGT CGTAACAACT CCGCCCCATT GACGCAAATG   840

GGCGGTAGGC GTGTACGGTG GGAGGTCTAT ATAAGCAGAG CTCGTTTAGT GAACCGTCAG   900

ATCGCCTGGA GACGCCATCC ACGCTGTTTT GACCTCCATA GAAGACACCG GGACCGATCC   960

AGCCTCCGCG GCCGGGAACG GTGCATTGGA ACGCGGATTC CCCGTGCCAA GAGTGACGTA  1020

AGTACCGCCT ATAGAGTCTA TAGGCCCACC CCCTTGGCTT CTTATGCGAC GGATCAATTC  1080

GCTGTCTGCG AGGGCCAGCT GTTGGGGTGA GTACTCCCTC TCAAAAGCGG GCATGACTTC  1140

TGCGCTAAGA TTGTCAGTTT CCAAAAACGA GGAGGATTTG ATATTCACCT GGCCCGCGGT  1200

GATGCCTTTG AGGGTGGCCG CGTCCATCTG GTCAGAAAAG ACAATCTTTT TGTTGTCAAG  1260

CTTGAGGTGT GGCAGGCTTG AGATCTGGCC ATACACTTGA GTGACAATGA CATCCACTTT  1320
```

-continued

```
GCCTTTCTCT CCACAGGTGT CCACTCCCAG GTCCAACGAT CCACTAGTTC TAGTACCAGC     1380

TGCTAGAGCT TGGTAAGTGA CCAGCTACAG TCGGAAACCA TCAGCAAGCA GGTATGTACT     1440

CTCCAGGGTG GGCCTGGCTT CCCCAGTCAA GACTCCAGGG ATTTGAGGGA CGCTGTGGGC     1500

TCTTCTCTTA CATGTACCTT TTGCTAGCCT CAACCCTGAC TATCTTCCAG GTCATTGTTC     1560

CAAC ATG GCC CTG TGG ATC GAC AGG ATG CAA CTC CTG TCT TGC ATT GCA     1609
     Met Ala Leu Trp Ile Asp Arg Met Gln Leu Leu Ser Cys Ile Ala
       1               5                  10                  15

CTA AGT CTT GCA CTT GTC ACA AAC AGT GCA CCT ACT TCA AGT TCT ACA     1657
Leu Ser Leu Ala Leu Val Thr Asn Ser Ala Pro Thr Ser Ser Ser Thr
            20                  25                  30

AAG AAA ACA CAG CTA CAA CTG GAG CAT TTA CTG CTG GAT TTA CAG ATG     1705
Lys Lys Thr Gln Leu Gln Leu Glu His Leu Leu Leu Asp Leu Gln Met
            35                  40                  45

ATT TTG AAT GGA ATT AAT AAT TAC AAG AAT CCC AAA CTC ACC AGG ATG     1753
Ile Leu Asn Gly Ile Asn Asn Tyr Lys Asn Pro Lys Leu Thr Arg Met
        50                  55                  60

CTC ACA TTT AAG TTT TAC ATG CCC AAG AAG GCC ACA GAA CTG AAA CAT     1801
Leu Thr Phe Lys Phe Tyr Met Pro Lys Lys Ala Thr Glu Leu Lys His
    65                  70                  75

CTT CAG TGT CTA GAA GAA GAA CTC AAA CCT CTG GAG GAA GTG CTA AAT     1849
Leu Gln Cys Leu Glu Glu Glu Leu Lys Pro Leu Glu Glu Val Leu Asn
 80                  85                  90                  95

TTA GCT CAA AGC AAA AAC TTT CAC TTA AGA CCC AGG GAC TTA ATC AGC     1897
Leu Ala Gln Ser Lys Asn Phe His Leu Arg Pro Arg Asp Leu Ile Ser
                100                 105                 110

AAT ATC AAC GTA ATA GTT CTG GAA CTA AAG GGA TCT GAA ACA ACA TTC     1945
Asn Ile Asn Val Ile Val Leu Glu Leu Lys Gly Ser Glu Thr Thr Phe
            115                 120                 125

ATG TGT GAA TAT GCT GAT GAG ACA GCA ACC ATT GTA GAA TTT CTG AAC     1993
Met Cys Glu Tyr Ala Asp Glu Thr Ala Thr Ile Val Glu Phe Leu Asn
        130                 135                 140

AGA TGG ATT ACC TTT TGT CAA AGC ATC ATC TCA ACA CTG ACT TGATAATTAA  2045
Arg Trp Ile Thr Phe Cys Gln Ser Ile Ile Ser Thr Leu Thr
    145                 150                 155

GTGCTTCCCA CTTAAAACAT ATCAGGGATC GATCCAGACA TGATAAGATA CATTGATGAG     2105

TTTGGACAAA CCACAACTAG AATGCAGTGA AAAAAATGCT TTATTTGTGA AATTTGTGAT     2165

GCTATTGCTT TATTTGTAAC CATTATAAGC TGCAATAAAC AAGTTAACAA CAACAATTGC     2225

ATTCATTTTA TGTTTCAGGT TCAGGGGGAG GTGTGGGAGG TTTTTTAAAG CAAGTAAAAC     2285

CTCTACAAAT GTGGTATGGC TGATTATGAT CCGGCTGCCT CGCGCGTTTC GGTGATGACG     2345

GTGAAAACCT CTGACACATG CAGCTCCCGG AGACGGTCAC AGCTTGTCTG TAAGCGGATG     2405

CCGGGAGCAG ACAAGCCCGT CAGGGCGCGT CAGCGGGTGT TGGCGGGTGT CGGGGCGCAG     2465

CCATGAGGTC GACTCTAGTA GAGCGGCCGC CACCGCGGTG GAGCTCCAAT TCGCCCTATA     2525

GTGAGTCGTA TTACGCGCGT CGAGTCTAGA GAGCTCGGGC CAAGCTTGG TACCCATGGC     2585

TACGTAGATA AGTAGCATGG CGGGTTAATC ATTAACTACA AGGAACCCCT AGTGATGGAG     2645

TTGGCCACTC CCTCTCTGCG CGCTCGCTCG CTCACTGAGA GACCGCGACC AAAGGTCGCC     2705

CGACGCCCGG GCTTTGCCCG GCGGCCTCA GTGAGCGAGC GAGCGCGCAG AGAGGGACAG     2765

ATCCAATTCG CCCTATAGTG AGTCGTATTA CGCGCGCTCA CTGGCCGTCG TTTTACAACG     2825

TCGTGACTGG GAAAACCCTG GCGTTACCCA ACTTAATCGC CTTGCAGCAC ATCCCCCTTT     2885

CGCCAGCTGG CGTAATAGCG AAGAGGCCCG CACCGATCGC CCTTCCCAAC AGTTGCGCAG     2945

CCTGAATGGC GAATGGGACG CGCCCTGTAG CGGCGCATTA AGCGCGGCGG GTGTGGTGGT     3005
```

```
TACGCGCAGC GTGACCGCTA CACTTGCCAG CGCCCTAGCG CCCGCTCCTT TCGCTTTCTT    3065

CCCTTCCTTT CTCGCCACGT TCGCCGGCTT TCCCCGTCAA GCTCTAAATC GGGGGCTCCC    3125

TTTAGGGTTC CGATTTAGTG CTTTACGGCA CCTCGACCCC AAAAAACTTG ATTAGGGTGA    3185

TGGTTCACGT AGTGGGCCAT CGCCCTGATA GACGGTTTTT CGCCCTTTGA CGTTGGAGTC    3245

CACGTTCTTT AATAGTGGAC TCTTGTTCCA AACTGGAACA ACACTCAACC CTATCTCGGT    3305

CTATTCTTTT GATTTATAAG GGATTTTGCC GATTTCGGCC TATTGGTTAA AAAATGAGCT    3365

GATTTAACAA AAATTTAACG CGAATTTTAA CAAAATATTA ACGCTTACAA TTTAGGTGGC    3425

ACTTTTCGGG GAAATGTGCG CGGAACCCCT ATTTGTTTAT TTTTCTAAAT ACATTCAAAT    3485

ATGTATCCGC TCATGAGACA ATAACCCTGA TAAATGCTTC AATAATATTG AAAAAGGAAG    3545

AGTATGAGTA TTCAACATTT CCGTGTCGCC CTTATTCCCT TTTTTGCGGC ATTTTGCCTT    3605

CCTGTTTTTG CTCACCCAGA AACGCTGGTG AAAGTAAAAG ATGCTGAAGA TCAGTTGGGT    3665

GCACGAGTGG GTTACATCGA ACTGGATCTC AACAGCGGTA AGATCCTTGA GAGTTTTCGC    3725

CCCGAAGAAC GTTTTCCAAT GATGAGCACT TTTAAAGTTC TGCTATGTGG CGCGGTATTA    3785

TCCCGTATTG ACGCCGGGCA AGAGCAACTC GGTCGCCGCA TACACTATTC TCAGAATGAC    3845

TTGGTTGAGT ACTCACCAGT CACAGAAAAG CATCTTACGG ATGGCATGAC AGTAAGAGAA    3905

TTATGCAGTG CTGCCATAAC CATGAGTGAT AACACTGCGG CCAACTTACT TCTGACAACG    3965

ATCGGAGGAC CGAAGGAGCT AACCGCTTTT TTGCACAACA TGGGGGATCA TGTAACTCGC    4025

CTTGATCGTT GGGAACCGGA GCTGAATGAA GCCATACCAA ACGACGAGCG TGACACCACG    4085

ATGCCTGTAG CAATGGCAAC AACGTTGCGC AAACTATTAA CTGGCGAACT ACTTACTCTA    4145

GCTTCCCGGC AACAATTAAT AGACTGGATG GAGGCGGATA AAGTTGCAGG ACCACTTCTG    4205

CGCTCGGCCC TTCCGGCTGG CTGGTTTATT GCTGATAAAT CTGGAGCCGG TGAGCGTGGG    4265

TCTCGCGGTA TCATTGCAGC ACTGGGGCCA GATGGTAAGC CCTCCCGTAT CGTAGTTATC    4325

TACACGACGG GGAGTCAGGC AACTATGGAT GAACGAAATA GACAGATCGC TGAGATAGGT    4385

GCCTCACTGA TTAAGCATTG GTAACTGTCA GACCAAGTTT ACTCATATAT ACTTTAGATT    4445

GATTTAAAAC TTCATTTTTA ATTTAAAAGG ATCTAGGTGA AGATCCTTTT TGATAATCTC    4505

ATGACCAAAA TCCCTTAACG TGAGTTTTCG TTCCACTGAG CGTCAGACCC CGTAGAAAAG    4565

ATCAAAGGAT CTTCTTGAGA TCCTTTTTTT CTGCGCGTAA TCTGCTGCTT GCAAACAAAA    4625

AAACCACCGC TACCAGCGGT GGTTTGTTTG CCGGATCAAG AGCTACCAAC TCTTTTTCCG    4685

AAGGTAACTG GCTTCAGCAG AGCGCAGATA CCAAATACTG TCCTTCTAGT GTAGCCGTAG    4745

TTAGGCCACC ACTTCAAGAA CTCTGTAGCA CCGCCTACAT ACCTCGCTCT GCTAATCCTG    4805

TTACCAGTGG CTGCTGCCAG TGGCGATAAG TCGTGTCTTA CCGGGTTGGA CTCAAGACGA    4865

TAGTTACCGG ATAAGGCGCA GCGGTCGGGC TGAACGGGGG GTTCGTGCAC ACAGCCCAGC    4925

TTGGAGCGAA CGACCTACAC CGAACTGAGA TACCTACAGC GTGAGCTATG AGAAAGCGCC    4985

ACGCTTCCCG AAGGGAGAAA GGCGGACAGG TATCCGGTAA GCGGCAGGGT CGGAACAGGA    5045

GAGCGCACGA GGGAGCTTCC AGGGGGAAAC GCCTGGTATC TTTATAGTCC TGTCGGGTTT    5105

CGCCACCTCT GACTTGAGCG TCGATTTTTG TGATGCTCGT CAGGGGGCG GAGCCTATGG    5165

AAAAACGCCA GCAACGCGGC CTTTTTACGG TTCCTGGCCT TTTGCTGGCC TTTTGCTCAC    5225

ATGTTCTTTC CTGCGTTATC CCCTGATTCT GTGGATAACC GTATTACCGC CTTTGAGTGA    5285

GCTGATACCG CTCGCCGCAG CCGAACGACC GAGCGCAGCG AGTCAGTGAG CGAGGAAGCG    5345
```

```
GAAGAGCGCC CAATACGCAA ACCGCCTCTC CCCGCGCGTT GGCCGATTCA TTAATGCAGC    5405

TGGCACGACA GGTTTCCCGA CTGGAAAGCG GGCAGTGAGC GCAACGCAAT TAATGTGAGT    5465

TAGCTCACTC ATTAGGCACC CCAGGCTTTA CACTTTATGC TTCCGGCTCG TATGTTGTGT    5525

GGAATTGTGA GCGGATAACA ATTTCACACA GGAAACAGCT ATGACCATGA TTACGCCAAG    5585
```

(2) INFORMATION FOR SEQ ID NO: 2:

(i) SEQUENCE CHARACTERISTICS:
        (A) LENGTH: 156 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ala Leu Trp Ile Arg Met Gln Leu Leu Ser Cys Ile Ala Leu Ser
 1               5                  10                  15

Leu Ala Leu Val Thr Asn Ser Ala Pro Thr Ser Ser Ser Thr Lys Lys
                20                  25                  30

Thr Gln Leu Gln Leu Glu His Leu Leu Leu Asp Leu Gln Met Ile Leu
            35                  40                  45

Asn Gly Ile Asn Asn Tyr Lys Asn Pro Lys Leu Thr Arg Met Leu Thr
    50                  55                  60

Phe Lys Phe Tyr Met Pro Lys Ala Thr Glu Leu Lys His Leu Gln
65                  70                  75                  80

Cys Leu Glu Glu Glu Leu Lys Pro Leu Glu Glu Val Leu Asn Leu Ala
                85                  90                  95

Gln Ser Lys Asn Phe His Leu Arg Pro Arg Asp Leu Ile Ser Asn Ile
            100                 105                 110

Asn Val Ile Val Leu Glu Leu Lys Gly Ser Glu Thr Thr Phe Met Cys
        115                 120                 125

Glu Tyr Ala Asp Glu Thr Ala Thr Ile Val Glu Phe Leu Asn Arg Trp
    130                 135                 140

Ile Thr Phe Cys Gln Ser Ile Ile Ser Thr Leu Thr
145                 150                 155
```

(2) INFORMATION FOR SEQ ID NO: 3:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 3:

```
Pro Asp Thr Arg Pro Ala Pro Gly Ser Thr Ala Pro Pro Ala His Gly
 1               5                  10                  15

Val Thr Ser Ala
            20
```

(2) INFORMATION FOR SEQ ID NO: 4:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 4:

Ser Gly Pro Ser Asn Thr Pro Pro Glu Ile
1               5                   10

(2) INFORMATION FOR SEQ ID NO: 5:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 5:

Arg Ala His Tyr Asn Ile Val Thr Phe
1               5

(2) INFORMATION FOR SEQ ID NO: 6:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 6:

Thr Asp Leu Tyr Cys Tyr Glu Gln Leu Asn
1               5                   10

(2) INFORMATION FOR SEQ ID NO: 7:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 7:

Ala Glu Pro Asp Arg Ala His Tyr Asn Ile
1               5                   10

(2) INFORMATION FOR SEQ ID NO: 8:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 8:

Lys Cys Asp Ser Thr Leu Arg Leu Cys Val Gln Ser Thr His Val Ile
1               5                   10                  15

Arg Thr Leu (2) INFORMATION FOR SEQ ID NO: 9:

```
    (i) SEQUENCE CHARACTERISTICS:
        (A) LENGTH: 10 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 9:

Gly Thr Leu Gly Ile Val Cys Pro Ile Cys
1               5                   10

(2) INFORMATION FOR SEQ ID NO: 10:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 10:

Asp Thr Pro Leu Ile Pro Leu Thr Ile Phe
1               5                   10

(2) INFORMATION FOR SEQ ID NO: 11:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO: 11:

Pro Arg Ser Pro Thr Val Phe Tyr Asn Ile Pro Pro Met Pro Leu
1               5                   10                  15

(2) INFORMATION FOR SEQ ID NO: 12:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 12:

Phe Leu Arg Gly Arg Ala Tyr Gly Leu
1               5

(2) INFORMATION FOR SEQ ID NO: 13:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 13:
```

```
Arg Gly Ile Lys Glu His Val Ile Gln Asn Ala Phe Arg Lys Ala
1               5                   10                  15
```

(2) INFORMATION FOR SEQ ID NO: 14:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 14:

```
Glu Glu Asn Leu Leu Asp Phe Val Arg Phe
1               5                   10
```

(2) INFORMATION FOR SEQ ID NO: 15:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 15:

```
Ile Val Thr Asp Phe Ser Val Ile Lys
1               5
```

(2) INFORMATION FOR SEQ ID NO: 16:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 16:

```
Leu Leu Gly Arg Asn Ser Pro Glu Val
1               5
```

(2) INFORMATION FOR SEQ ID NO: 17:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 17:

```
Lys Leu Val Val Val Gly Ala Arg Gly Val Gly Lys Ser
1               5                   10
```

(2) INFORMATION FOR SEQ ID NO: 18:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 18:

```
Lys Leu Val Val Val Gly Ala Val Gly Val Gly Lys
1               5                   10
```

(2) INFORMATION FOR SEQ ID NO: 19:

(i) SEQUENCE CHARACTERISTICS:
            (A) LENGTH: 16 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 19:

```
Asp Ile Leu Asp Thr Ala Gly Leu Glu Glu Tyr Ser Ala Met Arg Asp
1               5                   10                  15
```

(2) INFORMATION FOR SEQ ID NO: 20:

(i) SEQUENCE CHARACTERISTICS:
            (A) LENGTH: 8 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 20:

```
Gly Leu Glu Glu Tyr Ser Ala Met
1               5
```

(2) INFORMATION FOR SEQ ID NO: 21:

(i) SEQUENCE CHARACTERISTICS:
            (A) LENGTH: 10 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 21:

```
Glu Leu Val Ser Glu Phe Ser Arg Met Ala
1               5                   10
```

(2) INFORMATION FOR SEQ ID NO: 22:

(i) SEQUENCE CHARACTERISTICS:
            (A) LENGTH: 15 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 22:

```
His Leu Asp Met Leu Arg His Leu Tyr Gln Gly Cys Gln Val Val
1               5                   10                  15
```

(2) INFORMATION FOR SEQ ID NO: 23:

(i) SEQUENCE CHARACTERISTICS:
            (A) LENGTH: 15 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 23:

Ser Arg Leu Leu Gly Ile Cys Leu Thr Ser Thr Val Gln Leu Val
1               5                  10                  15

(2) INFORMATION FOR SEQ ID NO: 24:

(i) SEQUENCE CHARACTERISTICS:
            (A) LENGTH: 9 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 24:

Glu Ala Asp Pro Thr Gly His Ser Tyr
1               5

(2) INFORMATION FOR SEQ ID NO: 25:

(i) SEQUENCE CHARACTERISTICS:
            (A) LENGTH: 10 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 25:

Leu Leu Asp Gly Thr Ala Thr Leu Arg Leu
1               5                  10

(2) INFORMATION FOR SEQ ID NO: 26:

(i) SEQUENCE CHARACTERISTICS:
            (A) LENGTH: 9 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 26:

Tyr Leu Glu Pro Gly Pro Val Thr Ala
1               5

(2) INFORMATION FOR SEQ ID NO: 27:

(i) SEQUENCE CHARACTERISTICS:
            (A) LENGTH: 9 amino acids
            (B) TYPE: amino acid
            (D) TOPOLOGY: linear (ii) MOLECULE TYPE: peptide (v) FRAGMENT TYPE: N-terminal (xi) SEQUENCE DESCRIPTION: SEQ ID NO: 27:

```
Met Leu Leu Ala Val Leu Tyr Cys Leu
1               5

(2) INFORMATION FOR SEQ ID NO: 28:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 28:

Tyr Met Asn Gly Thr Met Ser Gln Val
1               5

(2) INFORMATION FOR SEQ ID NO: 29:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 29:

Tyr Met Asn Gly Thr Met Ser Glu Val
1               5

(2) INFORMATION FOR SEQ ID NO: 30:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 30:

Ala Ala Gly Ile Gly Ile Leu Thr Val Ile Leu Gly Val Leu Leu Leu
1               5                   10                  15

Ile Gly Cys Trp Tyr
                20
```

ADENO-ASSOCIATED VIRAL LIPOSOMES AND THEIR USE IN TRANSFECTING DENDRITIC CELLS TO STIMULATE SPECIFIC IMMUNITY

CROSS-REFERENCE TO RELATED APPLICATIONS

This application claims priority from Provisional Application Nos. 60/001,312, filed Jul. 21, 1995, and 60/007,184, filed Nov. 1, 1995, and is a continuation-in-part of application Ser. No. 08/566,286, filed Dec. 1, 1995, now abandoned which incorporates subject matter of said provisionals and also claims priority thereof; and this application is also a continuation-in-part of U.S. application Ser. No. 08/305,221, filed Sep. 12, 1994, now U.S. Pat. No. 5,834,441, which is a continuation-in-part of U.S. application Ser. No. 08/120,605, filed Sep. 13, 1993 (abandoned in favor of file wrapper continuation U.S. application Ser. No. 08/482,323, filed Jun. 6, 1995).

BACKGROUND OF THE INVENTION

1. Field of the Invention

The invention in the fields of molecular biology and medicine relates to improved methods and compositions for transfecting cells, particularly dendritic cells and other antigen presenting cells, through the use of cationic liposomes to facilitate transfection with adeno-associated viral (AAV) plasmids. Transfected cells expressing genes of interest, such as tumor-associated or viral antigens, are used for immunization and therapy.

2. Description of the Background Art

Transfection of eukaryotic cells has become an increasingly important technique for the study and development of gene therapy. Advances in gene therapy depend in large part upon the development of delivery systems capable of efficiently introducing DNA into a target cell. A number of methods have been developed for the stable or transient expression of heterologous genes in cultured cell types. These include transduction techniques which use a carrier molecule or virus.

Most gene therapy strategies have relied on transduction by transgene insertion into retroviral or DNA virus vectors. However, adenovirus and other DNA viral vectors can produce infectious sequelae, can be immunogenic after repeated administrations, and can only package a limited amount of insert DNA.

Of the viral vector systems, the recombinant adeno-associated viral (AAV) transduction system has proven to be one of the most efficient vector systems for stably and efficiently carrying genes into a variety of mammalian cell types (Lebkowski, J. S. et al., *Mol. Cell. Biol.* (1988) 8:3988–3996). It has been well-documented that AAV DNA integrates into cellular DNA as one to several tandem copies joined to cellular DNA through inverted terminal repeats (ITRs) of the viral DNA, and that the physical structure of integrated AAV genomes suggest that viral insertions usually appear as multiple copies with a tandem head to tail orientation via the AAV terminal repeats (Kotin, R. M. et al., *Proc. Natl. Acad. Sci. USA* (1990) 87:2211–2215). Thus, the AAV terminal repeats (ITRs) are an essential part of the AAV transduction system.

Although recombinant adeno-associated viral (AAV) vectors differ from adenoviral vectors, the transgene DNA size limitation and packaging properties are the same as with any other DNA viral vectors.

AAV is a linear single stranded DNA parvovirus, and requires co-infection by a second unrelated virus in order to achieve productive infection. AAV carries two sets of functional genes: rep genes, which are necessary for viral replication, and structural capsid protein genes (Hermonat, P. L. et al., *J. Virol.* (1984) 51:329–339). The rep and capsid genes of AAV can be replaced by a desired DNA fragment to generate AAV plasmid DNA. Transcomplementation of rep and capsid genes are required to create a recombinant virus stock. Upon transduction using such virus stock, one recombinant virus uncoats in the nucleus and integrates into the host genome by its molecular ends.

Although extensive progress has been made, transduction techniques suffer from variable efficiency, significant concern about possible recombination with endogenous virus, cellular toxicity and host immune reactions. Thus, there is a need for non-viral DNA transfection procedures.

Liposomes have been used to encapsulate and deliver a variety of materials to cells, including nucleic acids and viral particles (Faller, D. V. et al., *J. Virol.* (1984) 49:269–272).

Preformed liposomes that contain synthetic cationic lipids have been shown to form stable complexes with polyanionic DNA (Felgner, P. L. et al., *Proc. Natl. Acad. Sci. USA* (1987) 84:7413–7417). Cationic liposomes, liposomes comprising some cationic lipid, that contain a membrane fusion-promoting lipid dioctadecyldimethyl-ammonium-bromide (DDAB) have efficiently transferred heterologous genes into eukaryotic cells (Rose, J. K. et al., *Biotechniques* (1991) 10:520–525). Cationic liposomes can mediate high level cellular expression of transgenes, or mRNA, by delivering them into a variety of cultured cell lines (Malone, R. et al., *Proc. Natl. Acad. Sci. USA* (1989) 86:6077–6081).

Ecotropic and amphotropic packaged retroviral vectors have been shown to infect cultured cells in the presence of cationic liposomes, such as Lipofectin (BRL, Gaithersburg, Md.), and in the absence of specific receptors (Innes, C. L. et al., *J. Virol.* (1990) 64:957–961).

Even though non-viral techniques have overcome some of the problems of the viral systems, the need still remains for improved transfection efficiency in non-viral systems, increased range of cell types that are transfectable, increased duration of expression in transfected cells, and increased levels of expression following transfection. Some improved efficiency is attained by the use of promoter enhancer elements in the plasmid DNA constructs (Philip, R., et al., *J. Biol. Chem.* (1993) 268:16087–16090).

Immune Destruction of Tumor Cells

Interleukin-2 (IL-2) has been used to treat neoplasms such as metastatic renal cell carcinoma, as one approach to the immune-mediated destruction of human cancer. Although durable complete remissions have been achieved, the overall response rate has been low.

Testing of recombinant IL-2 (rIL-2) (Chiron Corp., Emeryville, Calif.) on cancer patients has revealed dose-limiting toxicity which was dependent upon the route and schedule of IL-2 administration. High dose bolus IL-2 administration was associated with significant toxicity involving nearly every organ system. Moreover, a 4% mortality rate in ECOG 0 performance status patients has been found with high dose IL-2. For an overview of ECOG performance status, see, e.g., Oken, Am. *J. Clin. Oncol.* (CCT) 5:649–655 (1982), Table 2, at p. 654).

As distinguished from bolus administration, use of lower dose ($1$–$7 \times 10^6$ Cetus units/$M^2$/day) continuous intravenous infusion of IL-2 has demonstrated clinical efficacy and lowered toxicity, suggesting an improved safety profile in adoptive immunotherapy of advanced cancer (West, W. H. et al., (1987) *N. Engl. J. Med.* 316:898).

Cell populations which potentially mediate or promote the immune destruction of tumors when combined with IL-2 include lymphokine activated killer (LAK) cells and cytotoxic T lymphocytes (CTL) in particular tumor-infiltrating lymphocytes (TIL). TIL are primarily T lymphocytes found in close apposition to a tumor mass which can be isolated, expanded, and activated in vitro. TIL are of interest in the treatment of neoplasia because of their affinity and presumably their specificity for tumor cells as well as their cytotoxic action. TILs have been reinfused into patients along with exogenous IL-2 (see, e.g., U.S. Pat. No. 5,126,132, Rosenberg, Jun. 30, 1992) which, in some instances, resulted in durable complete remissions of advanced malignancies.

Dendritic Cells

Many attempts have been made to elicit immune responses in subjects that would lead to destruction and removal of unwanted cells, tissues or microorganisms, in particular, tumors or oncogenic viruses such as Epstein-Barr virus (EBV). However, success has been limited. One difficulty is in adequately presenting tumor-associated antigens to the immune system to evoke a cellular immune response. Dendritic cells ("DC"; plural is "DCs") are known to be highly potent antigen-presenting cells ("APC; plural is (APCs"). For a review of DCs and their role in immunogenicity, see Steinman, R., *Annu. Rev. Immunol.* 9:271–296 (1991), which reference is incorporated by reference in its entirety. The present invention employs such cells as a means to present tumor antigens to elicit a specific immune response in vitro or in vivo.

Antigen-specific CTL have been a subject of active investigation for their potential immunotherapeutic utility in the treatment of cancer or virus infection. Tumor-associated antigens (TAA), identified in a number of different types of tumors, including carcinomas can be used for in vitro generation of CTL with lytic activity against cells of the tumor. CEA (carcinoembryonic antigen) is a well-known TAA that is expressed on a majority of colorectal, gastric, pancreatic, non-small cell lung, and breast carcinomas. MART-1 is an example of an antigen associated with melanoma. The present invention targets CEA and melanoma antigens as well as other tumor-associated antigens.

SUMMARY OF THE INVENTION

Cationic liposomes are used to facilitate adeno-associated viral (AAV) plasmid transfections of primary and cultured cell types. AAV plasmid DNA complexed with liposomes results in several-fold higher levels of expression of the DNA than do complexes using standard conventional plasmids. In addition, expression lasts for a period of 30 days without any selection. AAV plasmid:liposome complexes induced levels of transgene expression comparable to those obtained by recombinant AAV transduction. High levels of gene expression were observed in freshly isolated CD4$^+$ and CD8$^+$ T cells, TILs and CD34$^+$ stem cells from normal human peripheral blood.

Primary breast, ovarian and lung tumor cells have been transfected using the AAV plasmid DNA:liposome complexes. Transfected tumor cells also expressed the transgene product after lethal irradiation. Transfection efficiency ranged from 10–50% as assessed by J-galactosidase (J-gal) gene expression. The ability to express transgenes in primary tumor cells is utilized to produce tumor vaccines and to generate lymphoid cells that permit highly specific modulations of the cellular immune response in cancer and AIDS, and in gene therapies.

Disclosed herein is a composition for genetic manipulation of host cells which comprises a liposome comprising lipid material and AAV material. The AAV material is preferably a plasmid, such as pMP6-IL2 or pACMV-IL2. The AAV material can comprise an inverted terminal repeat (ITR), or two or more ITRs. Where two ITRs are present in the AAV material, a DNA sequence (or "genetic material") of interest can be integrated between the two ITRs. Moreover, a promoter can be integrated between two ITRs. The promoter can be any of a number of promoters which are active in eukaryotic, preferably mammalian, more preferably human cells, such as a CMV immediate-early promoter, a CMV immediate-late promoter, a CMV early promoter, an ADA promoter, or a TK promoter. The composition preferably comprises a DNA sequence of interest, such as a an IL-2 gene or a J-gal gene. The lipid material can comprise a cationic lipid. Also provided are cells transfected by the composition, including antigen-presenting cells, more preferably dendritic cells.

Disclosed herein is a method for introducing a genetic sequence of interest into a host cell. The method comprises steps of providing a composition comprising liposome AAV material end a genetic sequence of interest and contacting the composition with a host cell (which comprises genetic material) whereby the sequence of interest is introduced into the host cell. The host cell can be a CD34$^+$ stem cell, a T cell, such as a CD3$^+$, CD4$^+$, or CD8$^+$ cell, a cell of a tumor cell line such as a bladder cancer, prostate cancer or B lymphoma cell, or an embryonic kidney cell line. Alternatively, the tumor cell may be a primary tumor cell. The step of providing a composition can comprise providing a liposome that comprises cationic lipid. Also included is providing a composition of AAV material that comprises a plasmid, for example, pMP6-IL2 or pACMV-IL2. The method for introducing the genetic sequence of interest into a cell can further comprise a step of integrating the sequence of interest into the genetic material of the host cell.

Disclosed is a method for treating a subject, preferably a human. The treatment method comprises (a) providing a subject with a condition in need of treatment, and (b) providing a composition comprising liposome AAV material and a genetic sequence of interest. The method further comprises a step of contacting the composition with a host cell, whereby the genetic sequence of interest is introduced into the host cell. The contacting step can be in vivo, in which case the host cell is a cell of the subject. Alternatively, the contacting can be ex vivo, in which case the method further comprises a step of delivering the host cell which has been transfected with genetic sequence of interest to the subject. The subject of the present method is preferably one having a condition such as a neoplasm (including a malignant neoplasm), an infection, including HIV infection, an autoimmune condition or a genetic abnormality, such as a missing or defective gene.

The genetic sequence of interest may encode a peptide, an anti-sense oligonucleotide, or RNA. Preferred plasmids to be provided include pMP6-IL2 or pACMV-IL2. The genetic sequence of interest comprises may encode a cytokine, including IL-2 (and may comprise IL-2 genomic DNA, a costimulatory factor, an MHC class I molecule, a tumor-specific or a tumor-associated antigen or the MDR I gene. When the method involves contacting the composition of the invention with a host cell, the host cell may be a neoplastic cell (including a primary tumor cell or a cell of a tumor cell line), a bone marrow hematopoietic cell, a peripheral blood cell or a TIL.

Other preferred plasmids have the pMP6 backbone, as described herein, with any other gene of interest inserted in place of the IL-2 gene of the pMP6-IL2 plasmid A preferred expression vector comprises a genetic sequence essentially that depicted in FIG. 3 (SEQ ID NO:1). Also preferred is an expression vector which comprises a genetic sequence substantially that of SEQ ID NO:1. In another embodiment, the expression vector comprises a genetic sequence which is SEQ ID NO:1. In a preferred embodiment, the expression vector comprises a genetic sequence essentially that of the genetic sequence of plasmid pMP6, or substantially that of the genetic sequence of plasmid pMP6 or the genetic sequence of plasmid pMP6. An expression vector comprising a genetic sequence essentially that of genetic sequence of plasmid pMP6 preferably further comprises a DNA sequence of interest to be introduced into a cell being transfected, for example a tumor cell or a DC.

Also provided is a cell that is genetically modified with an expression vector comprising a genetic sequence essentially that of SEQ ID NO:1 or with any of the expression vectors listed above. The genetically modified cell can be a cell of any of the categories described above.

The present invention provides a method for producing a protein comprising the steps of providing a composition comprising liposome, AAV material and a genetic sequence of interest. The foregoing composition is contacted with a host cell which comprises genetic material, whereby the genetic sequence of interest is introduced into the host cell. The protein production method further comprises a step of expressing a protein encoded by the genetic sequence of interest. The host cell can be a CD34$^+$ stem cell, a T cell, a cell of a tumor cell line or a primary tumor cell, a TIL, or any CD3$^+$, CD4$^+$, or CD8$^+$ cell. When the cell is from a cell line, preferably a tumor cell line, it may be a bladder cancer cell, a prostate cancer cell, a B lymphoma, or a cell of an embryonic kidney cell line.

The composition provided in the protein production method, as described above, may comprises cationic lipid and AAV material. The AAV material preferably comprises a plasmid, such as pMP6-IL2 or pACMV-IL2.

The above method for producing a protein can comprise a further step of integrating the genetic material of interest into the genetic material of the host cell. The step of expressing a protein can comprise expressing a lymphokine, such as IL-2, a lymphokine analog, the product of the MDR-I gene or a marker or reporter product such as J-gal or chloramphenicol-acetyl-transferase (CAT)

Another objective of the present invention is to provide methods for generating tumor antigen-specific CTL for use in adoptive immunotherapy. An approach taken by the present inventors involved the use of DC to express and present the desired tumor antigen either by direct loading of the DC with the antigen or by transfection of DC with genetic constructs which will result in expression of the antigen. Such transfections are preferably accomplished using the methods and compositions described herein, namely AAV plasmid DNA (which includes DNA encoding the TAA) complexed with cationic liposomes. The AAV plasmid/cationic liposome methods and compositions are also used to express other antigens on DC, for example, viral antigens, preferably HIV antigens which serve as the target of an effective antiviral T cell or antibody response.

The invention is directed, in one aspect, to the expression of nonendogenous peptides or proteins, in particular TAA or a viral antigen, in or on the surface of DC. The invention is further directed to the use of DC as APCs to generate CTL capable of killing tumor cells or virus-infected cells bearing the antigen. The antigens are provided to the DC either by pulsing the cells with the desired peptide or by transfecting the cells with a vector capable of expressing the desired antigen whereby the DC can appropriately present the peptide on its surface.

Given applicants' discovery that antigen presentation by C cells to CTL provokes a very effective response by CTL, it is believed that a variety of other methods for providing a given protein or peptide antigen to a DC cell can be used to generate CTL capable of killing tumor cells or virus infected cells which are bearing the antigen. The DC are preferably used to stimulate a potent reactive lymphocyte population, preferably CTL, in culture, and such lymphocytes are then administered to the subject to effect treatment of a condition such as a tumor or virus infection. Alternatively or additionally, as a direct form of immunotherapy, the DC expressing the desired antigen in immunogenic form are administered to a subject and used to elicit a CTL response or other protective immune response in vivo.

The present invention provides a non-immortalized DC transfected by a vector including a DNA sequence not native to the DC. Also provided is a DC or other APC transfected by a composition comprising a liposome (which comprises lipid material) and AAV material. The AAV material preferably comprises a plasmid which preferably includes a DNA sequence of interest encoding one or more of a tumor-specific antigen, a tumor-associated antigen, a microbial antigen, a cytokine, a cellular receptor, a reporter molecule or a selectable marker. A preferred plasmid is pMP6 in which is inserted the DNA sequence of interest.

This invention is further directed to a method for introducing a DNA sequence of interest into a DC or other APC comprising the steps of:

(a) providing a composition comprising liposome, preferably cationic lipid, AAV material, preferably a plasmid, and a DNA sequence of interest; and (b) contacting the composition of step (a) with the cell, which cell comprises genetic material, such that the DNA sequence of interest is introduced into the cell. A preferred plasmid is pMP6 in which is inserted the DNA sequence of interest.

In the above method, the DNA sequence of interest preferably encodes one or more of a tumor-specific or tumor-associated antigen, a microbial antigen, a cytokine, a cellular receptor, a reporter molecule or a selectable marker. The tumor-specific or tumor-associated antigen may be carcinoembryonic antigen, a breast tumor antigen, a colorectal tumor antigen, a gastric tumor antigen, a pancreatic tumor antigen, a lung tumor antigen, an ovarian tumor antigen, a bladder tumor antigen, a prostate tumor antigen, a melanoma antigen, a leukemia antigen or a lymphoma antigen. The microbial antigen may be any viral or bacterial antigen. Preferably viral antigens are human retrovirus or human DNA virus antigens, preferably Epstein-Barr viral antigen or an HIV-1 or HIV-2 antigen. The cytokine is preferably IL-2. The receptor may be nerve growth factor receptor. A preferred reporter molecule is bacterial chloramphenicol acetyl transferase.

In the foregoing method, the DNA sequence of interest may or may not integrate into the genetic material of the transfected cell.

The present invention provides a method for treating a subject having a disease or condition which is treatable by stimulating an immune response to a selected antigen in the subject, which method comprises the steps of:

(a) contacting DCs or other APCs of the subject in vivo with a composition comprising liposome, adeno-associated virus material and a DNA sequence of interest which encodes the selected antigen such that the DNA sequence is introduced into the cells; and (b) allowing the antigen encoded by the DNA sequence to be expressed and to stimulate the immune response of the subject, thereby treating the subject.

In a related embodiment, the method comprises steps of:

(a) contacting dendritic cells or other antigen-presenting cells, which cells are autologous or allogeneic to the subject, ex vivo with a composition comprising liposome, adeno-associated virus material and a DNA sequence of interest which encodes the selected antigen such that the DNA sequence is introduced into the cells;

(b) allowing the antigen encoded by the DNA sequence to be expressed in the cells; and (c) delivering the cells expressing the antigen to the subject to stimulate the immune response, thereby treating the subject.

In yet another related embodiment, the method comprises the steps of:

(a) contacting dendritic cells or other antigen-presenting cells, which cells are autologous or allogeneic to the subject, ex vivo with a composition comprising liposome, adeno-associated virus material and a DNA sequence of interest which encodes the selected antigen such that the DNA sequence is introduced into the cells;

(b) allowing the antigen encoded by the DNA sequence to be expressed in the cells;

(c) activating lymphocytes ex vivo by contacting them with the cells expressing the antigen such that the lymphocytes become cytotoxic or otherwise specifically immunoreactive to host cells bearing the antigen; and (d) delivering the activated lymphocytes to the subject to mediate the immune response in the subject, thereby treating the subject.

In the foregoing treatment methods, the condition or disease to be treated may be neoplasia or an infection. Examples of neoplasia which are treated by these methods include breast cancer, colorectal cancer, gastric cancer, pancreatic cancer, lung cancer, ovarian cancer, bladder cancer, prostate cancer, melanoma, leukemia and lymphoma.

Infections which may be treated by these methods include infection with a human retrovirus, preferably HIV-1 or HIV-2, HTLV-1, HTLV-2 and the like, or a human DNA virus, preferably Epstein-Barr virus or other herpesviruses.

In the foregoing treatment methods, the DNA sequence of interest preferably encodes one or more of a tumor-specific antigen, a tumor-associated antigen or a microbial antigen. Tumor-associated or tumor-specific antigens include carcinoembryonic antigen, a breast tumor antigen, a colorectal tumor antigen, a gastric tumor antigen, a pancreatic tumor antigen, a lung tumor antigen, an ovarian tumor antigen, a bladder tumor antigen, a prostate tumor antigen, a melanoma antigen, a leukemia antigen or a lymphoma antigen. Microbial antigens include bacterial or viral antigens, preferably an HIV antigen, for example, an epitope of a protein encoded by the HIV gag, pol, env or nef gene.

In the foregoing treatment methods, the DNA sequence of interest may further encode a cytokine, a costimulatory factor or an antigen of an MHC class I molecule.

This invention is also directed to a method for producing a protein in a dendritic cell comprising:

(a) introducing a DNA sequence encoding the protein into a dendritic cell; and (b) allowing the DNA sequence to be expressed, thereby producing the protein. The introducing is preferably performed by transfecting the cell with a composition comprising liposome, adeno-associated virus material and the DNA sequence, as described herein.

Another aspect of the present invention is the provision of a method for eliciting an immune response to a tumor-associated antigen comprising providing a modified dendritic cell bearing a selected tumor-associated antigen and contacting a cytolytic T cell with said dendritic cell bearing said tumor-associated antigen. The contacting can occur in vivo or in vitro. The term "modified" refers to a dendritic cell that has been changed so that it bears a tumor-associated antigen that has been selected based on the nature of the tumor in a patient to be treated.

BRIEF DESCRIPTION OF THE DRAWINGS

FIG. 1 shows plasmid maps of three plasmids used in the present studies. The plasmid pACMV-IL2 contained the CMV promoter, IL-2 cDNA and rat preproinsulin and SV40 polyadenylation sequences identical to pBC12CMV/IL2 plasmid. pACMV-IL2 also had AAV inverted terminal repeats (ITRs) at both ends. The plasmid pA1CMVIX-CAT was constructed with a CMV promoter and CAT gene inserted between the two AAV ITRs.

FIG. 2 shows a detailed restriction map of the IL-2-expressing form of the pMP6 plasmid, named pMP6-IL2.

FIGS. 3a–3e depicts the nucleotide sequence of the pMP6-IL2 plasmid. Panels 3a–3e depict successive portions of the sequence (SEQ ID NO:1). Portions of the pMP6-IL2 sequence which correspond to known DNA sequences are indicated; the corresponding sequence information is listed directly beneath sequence information for the pMP6-IL2 plasmid. Unmarked sequences are from linkers. The amino acid sequence in panels 3B–3C is SEQ ID No:2.

FIGS. 4a and 4b are graphs depicting the levels of gene expression induced by plasmid DNA:liposome complexes. Various IL-2 plasmid constructs complexed with liposomes were tested for their capability to induce gene expression (expressed as $pg/ml/10^6$ cells) in a rat bladder cell line and a rat prostate cell line (FIG. 4a). In both cell lines, the AAV plasmid construct showed the highest level of expression. FIG. 4b depicts the time-course of gene expression induced by AAV plasmid:liposome complexes. For comparison, the prostate cell line was transfected with the AAV plasmid (pACMV-IL2) and the corresponding control plasmid (pBC12/CMV-IL2) complexed with liposomes. Supernatants were collected at various time points and assayed for IL-2 levels using an ELISA. IL-2 levels were expressed as $pg/ml/10^6$ cells in 24 hrs of culture.

FIGS. 5a–5b compare AAV plasmid:liposome complex-mediated transfection to recombinant AAV transduction. To determine whether the levels of gene expression induced by AAV plasmid:liposome complexes were equivalent to rAAV transduction, The prostate cell line (FIG. 5a) and bladder cell line (FIG. 5b) were used to compare the transfection and transduction of IL-2 gene. IL-2 levels expressed as $pg/ml/10^6$ cells in 24 hrs of culture were assessed using an ELISA.

FIG. 6 is a graph showing expression of the IL-2 gene after lipofection with AAV plasmid:liposome complexes of various primary tumor cells. One lung, one ovarian, and two breast tumor samples were isolated from fresh tumor biopsies. IL-2 levels ($pg/ml/10^6$ cells in 24 hrs of culture) were measured using an ELISA.

FIGS. 7a and 7b are graphs showing expression of IL-2 by transfected cells which were subjected to lethal irradiation. To determine the effect of irradiation on gene expression, the prostate cell line (FIG. 7a) and primary breast tumor cells (FIG. 7b) were transfected as described herein and assessed for expression of the IL-2 gene (as in the preceding Figures) following lethal irradiation. Supernatants were collected 24, 48, 72 and 96 hrs after irradiation and tested for IL-2 levels.

FIG. 8 is a graph showing efficiency (on a per cell basis) of AAV:liposome transfection measured by J-gal gene expression. The prostate tumor cell line was transfected as described herein. The results are presented as percent fluorescent cells (positive for J-gal).

In FIG. 11a, samples were digested with BamHI and HindIII and probed with IL-2 DNA. For FIG. 11b, samples were digested with BamHI and probed with IL-2 DNA. All clones analyzed show presence of IL-2 gene, as demonstrated by the 0.685 kb bands. The lanes in FIGS. 11a and 11b represent the following. Lane 1: 1 kb ladder; lane 2: plasmid cut with BamHI/HindIII (9a) and BamHI/PvuII (9b); lane 3: R33 untransfected; lanes 4–11: clones In FIG. 12a: lane 1: clone 1A11 cut with BamHI/HindIII; lane 2: clone 1B11 cut with BamHI/HindIII; lane 3: clone R33 cut with BamHI/HindIII; lane 4: clone 1A11 cut with BamHI; lane 5: clone 1B11 cut with BamHI; lane 6: clone R33 cut with BamHI; lane 7: clone 1A11 cut with HindIII; lane 8: clone 1B11 cut with HindIII; lane 9: clone R33 cut with HindIII; lane 10: empty; lane 11: pACMV-IL2 plasmid cut with BamHI/HindIII; lane 12: pACMV-IL2 plasmid cut with HindIII/PvuII; lane 13: pACMV-IL2 plasmid cut with BamHI/PvuII. In FIG. 12b, the filter was probed with a 0.85 kb pvuII/HindIII (AAV ITR/CMV) fragment of the plasmid pACMV-IL2. Lane 1: clone 1A11 cut with SmaI; lane 2: clone 1B11 cut with SmaI; lane 3: clone R33 cut with SmaI; lane 4: clone 1A11 cut with PvuII/HindIII; lane 5: clone 1B11, cut with PvuII/HindIII; lane 6: clone R33, cut with PvuII/HindIII; lane 7: pACMV-IL2, cut with BamHI/HindIII; lane 8: pACMV-IL2, cut with HindIII/PvuII; lane 9: pACMV-IL2, cut with SmaI; lane 10: 1 kb ladder FIG. 13 shows the results of T cell receptor (TCR) repertoire analysis using RNAase protection of breast cancer TIL expanded with: (a) autologous tumor, (b) IL-2 transduced tumor, and (c) IL-2 alone. "VJ" is a variable segment of the TCR J chain; "CJ" is the constant segment of the TCR J chain. A, B, and C on the abscissa represent three different human subjects.

FIG. 14 depicts the proliferation of TIL infiltrating a breast tumor measured 5 days after IL-2 gene transfection.

FIG. 15 depicts the efficiency of gene expression in breast cancer TIL transfected with the pMP6 plasmid containing the neomycin resistance gene and the Thy 1.2 gene (pMP6/neo/Thy1.2) (instead of the IL-2 gene). The pMP6/neo/Thy1.2 plasmid was complexed to DDAB:DOPE liposomes. The liposome compositions were the same compositions as those used for FIG. 14.

FIG. 16 shows a comparison of the levels and duration of transgene expression following transfections with various plasmid constructs. The prostate tumor cell line R3327 was transfected with standard plasmid pBC12/CMV-IL2 or the AAV plasmid pACMV-IL2 complexed to DDAB:DOPE liposomes. Supernatants were collected at various time points and assayed by ELISA for IL-2 levels (expressed as $pg/ml/10^6$ cells in 24 hrs of culture).

FIG. 18 shows results of an intracellular assay of the transfection efficiency of the IL-2 gene in prostate tumor cell line R3327. The cells were transfected with the AAV IL-2 plasmid complexed with DDAB:DOPE liposomes (1:1 or 1:2 ratios). Transfected cells were stained at various time points for intracellular IL-2 protein. The results show percent positive cells expressing IL-2 protein. Untransfected cells were used as negative controls and the values of controls were subtracted from the values of transfected groups.

FIGS. 19(A–B) shows expression of IL-2 by irradiated prostate tumor cell line cells (Panel A) and by irradiated primary breast tumor (Panel B). Tumor cells were transfected and assessed for gene expression after lethal irradiation. Supernatants were collected 24, 48, 72 and 96 hrs after irradiation and tested for IL-2 levels ($pg/ml/10^6$ cells in 24 hr culture).

FIG. 33 shows MART-1-specific cytotoxicity on T2 target cells pulsed with MART-1 peptide (T2-MART) or empty T2 cells (T2) at effector:target ratios of 60:1, 30:1, 15:1, or 7.5:1.

FIG. 34 shows MART-1-specific cytotoxicity on an A2$^+$MART-1$^+$ melanoma line (624Mel) or an A2$^+$MART-1 melanoma line (A375) at E:T ratios of 60, 30, 15, or 7.5.

FIG. 35 characterizes the phenotypes of effector cells stimulated with MART-1-loaded DC (DC-MART) or IL-7 only on the day of the cytotoxicity assay. Cells were stained with antibodies to CD3, CD4, CD8, and CD56. Greater than 90% of the effector cells are CD3$^+$CD8$^+$.

FIG. 36 shows MART-1-specific cytotoxicity on T2 cells pulsed with MART-1 peptide (T2-MART) or empty T2 cells (T2) at effector:target ratios of 60 or 30.

FIG. 37 shows MART-1-specific cytotoxicity on an A2$^+$MART-1$^+$ cell line (624Mel) or an A2$^+$MART-1 cell line (Colo) at E:T ratios of 60 or 30.

FIG. 38 characterizes the phenotypes of effector cells stimulated with MART-1-loaded DC (DC-MART) or control unpulsed DC on the day of the cytotoxicity assay. Cells were stained with antibodies to CD3, CD4, CD8, and CD56. About 70% of the effector cells are CD3$^+$CD8$^+$.

DESCRIPTION OF THE PREFERRED EMBODIMENTS

Figure 9A:
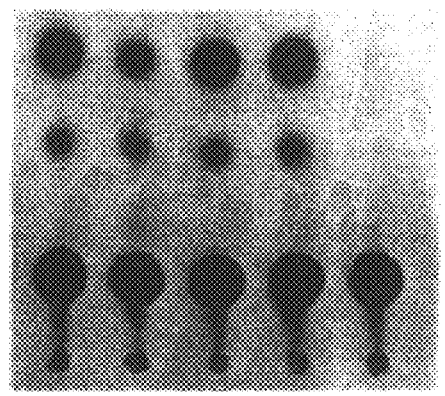
FIGS. 9a–9d present thin layer chromatograms (TLC) made from transfected T lymphocytes. Blood was obtained from two donors referred to as A or B, from which T cells were isolated for transfection. These T cells were transfected using AAV plasmid DNA:liposome complexes. T lymphocytes were fractionated into various subpopulations using AIS MicroCELLector® devices as follows: $CD3^+$ (FIG. 9a), $CD5^+/8^+$ (FIG. 9b), $CD4^+$ (FIG. 9c) or $CD8^+$ (FIG. 9d). The relevant cells were captured and cultured as described herein. Thereafter, $5-10 \times 10^6$ cells were plated and transfected with 50 µg AAV plasmid DNA and 50 or 100 nmoles of liposomes to obtain 1:1 or 1:2 DNA:liposome ratios. The cells were harvested 3 days after transfection. Normalized amounts of protein content from the extracts were assayed for CAT activity using a TLC assay.

The studies, disclosed for the first time herein, examined the transportation into cells of AAV plasmid DNA employing a system that did not involve viral transduction. Alternatively, a method in accordance with the present disclosure efficiently transfected several mammalian cell types by use of liposomes comprising AAV material. The successful transfection utilizes the elegant carrier system of lipofection together with the proficient transduction capability of the AAV plasmid construct. Advantageously, cationic liposomes were used as a means to facilitate the entry of AAV plasmid DNA into cells in the absence of rep and capsid transcomplementation, recombinant virus or wild type AAV.

A lipofection method in accordance with the invention was evaluated to assess the efficiency of gene expression. The present results established the ability to transfect unmodified stem cells, unmodified primary lymphoid cells such as T cells, a variety of freshly isolated tumor cells, and cultured mammalian cell types, with high efficiency leading to both transient and sustained expression of the transfected DNA. The ability to efficiently transfect unmodified T cells, such as tumor infiltrating lymphocytes, unmodified stem cells, tumor cell line cells and primary tumor cells is disclosed for the first time in the art.

Cell and gene therapy of cancer primarily depends on the ability to isolate and manipulate, ex vivo, the effector cell populations utilizing an efficient vector system. The present inventors have used the combination of cationic liposomes with plasmids containing the inverted terminal repeats (ITRs) of adeno-associated virus (AAV) to express transgenes in a variety of primary cell types including monocyte-derived DC. This vector system demonstrated higher levels of expression when compared to the standard plasmid, although equal amounts of DNA was delivered to the cells. DC from peripheral blood mononuclear cell (PBMC) populations were used successfully to generate peptide-specific responses. In addition, using AAV plasmid DNA containing reporter genes, which DNA was complexed to cationic liposomes, the present inventors have achieved transgene expressior in DC with an efficiency of about 10–30%.

Source Materials and Methods

A. Cell Lines

A rat prostate cell line (R3327) and rat bladder cell line (MBT-2) were obtained from Dr. Eli Gilboa, Duke University. Both cell lines were maintained in RPMI-1640 medium supplemented with 5% fetal bovine serum (FBS). Cell line 293 is a human embryonic kidney cell line that was transformed by adenovirus type 5, and was obtained from the ATCC (Graham, F. L., et al., *J. Gen. Virol.* (1977) 36:59–72). 293 cells were grown in Dulbecco modified eagle medium supplemented with 10% FBS.

B. Cell Preparation of Primary Tumor Cells

Primary lung, ovarian and three breast tumor cells were obtained from solid tumors of patients. The tumor samples were minced into small pieces and digested in 200 ml of AIM V medium (Gibco), supplemented with 450 u/ml collagenase IV (Sigma), 10.8 K units/ml DNase I (Sigma), and 2000 u/ml hyaluronidase V (Sigma) (Topolian, S. L. et al., *J. Immunol. Methods* (1987) 102:127–141). After 1–2 hours of digestion, cells were homogenized with a glass homogenizer (Bellco) and washed three times in DPBS-CMF (Whittaker). Lymphocytes were separated from non-lymphoid cells by capture on an AIS MicroCELLector-CD5/8® device (Applied Immune Sciences, Santa Clara, Calif.). Nonadherent cells (mainly tumor cells) were removed and cultured in RPMI 1640 medium supplemented with 2 mM L glutamine, 100 u/ml penicillin-streptomycin, and 10% FBS. Tumor cells were cultured for 2 to 4 weeks prior to transfection.

C. Preparation of Peripheral Blood Mononuclear Cells

Peripheral blood mononuclear cells (PBMCS) from healthy control patients were isolated from buffy coats (Stanford University Blood Bank, Stanford, Calif.) using Lymphoprep (Nycomed, Norway).

T cells, T cell subsets, or $CD34^+$ cells were further isolated using AIS MicroCELLectors (Applied Immune Sciences, Santa Clara, Calif.), devices comprising surfaces having covalently attached specific binding proteins (such as monoclonal antibodies) attached thereto. Briefly, PBMCs were resuspended at $15 \times 10^6$ cells per ml in 0.5% Gamimmune (Miles, Inc., Elkhart, Ind.) and loaded onto washed CD3, CD4, CD8, CD5/8, or CD34 AIS MicroCELLectors®. After 1 hour, nonadherent cells were removed from the AIS MicroCELLectors®. Complete medium, RPMI 1640 (Whittaker) containing 10% fetal bovine serum, 2 mM L-glutamine, and 100 u/ml penicillin/streptomycin was added to the adherent cells in the AIS MicroCELLectors. After 2–3 days in a 5% $CO_2$, 37° C. humidified environment, adherent cells were removed and prepared for transfection.

D. Plasmid Preparation

A first plasmid used in the present studies, pACMV-IL2, contained the human interleukin-2 gene (IL-2) as IL-2 cDNA, and the immediate-early promoter-enhancer element of the cytomegalovirus (CMV) and rat preproinsulin and SV40 polyadenylation sequences, flanked by AAV ITRs at both ends. This plasmid was obtained from and is available from Dr. J. Rosenblatt, UCLA, Los Angeles, Calif. and is also designated pSSV9/CMV-IL2). A corresponding control plasmid pBC12/CMV-IL2, which was identical to pACMV-IL2 but which lacked the AAV terminal repeats, was also used (see FIG. 1).

The plasmid pA1CMVIX-CAT contained the CMV immediate-early promoter enhancer sequences, an intron derived from pOG44 (Stratagene), the bacterial CAT gene, SV40 late polyadenylation signal flanked by AAV terminal repeats in a pBR322 backbone (see FIG. 1).

The plasmids pATK-Jgal and pAADA-Jgal contained the Jgal gene linked to either the TK or ADA promoter, respectively, in an AAV plasmid backbone. These plasmids were provided by Dr. Eli Gilboa, Duke University, Durham, N.C.)

Another plasmid used in the present studies was pMP6. As shown in FIG. 2, this plasmid containing IL-2 DNA (and designated pMP6-IL2) is double stranded and circular. pMP6-IL2 has the human IL-2 gene under the control of a CMV promoter End a SV40 polyadenylation signal. Between the promoter and the coding sequences of IL-2, there is an intron (derived from pOG44) which is understood to enhance the expression of IL-2 or any other exogenous gene placed into the plasmid. The entire expression cassette is between the left and right terminal repeat sequences of AAV. The pMP6-IL2 plasmid also has a Bluescript backbone having a Col-El bacterial origin of replication and an ampicillin resistance gene which facilitates the propagation of this plasmid in *E. coli*.

FIGS. 3a–3e shows the DNA sequence of the pMP6-IL2 plasmid (SEQ ID NO:1) depicted as successive portions of the sequence. Portions of the pMP6-IL2 sequence which correspond to known DNA sequences are indicated; the corresponding sequence information is listed directly beneath sequence information for the pMP6-IL2 plasmid. Unmarked sequences are from linkers.

Standard plasmids containing the IL-2 gene, but that did not contain AAV components were also used. The standard plasmid constructs carried the IL-2 gene, with an adenosine deaminase (ADA), a thymidine kinase (TK) or the immediate-late cytomegalovirus (CMV) promoter (standard plasmids obtained from ATCC). Selected plasmids are described in Table 1, below.

All plasmids were isolated by alkaline lysis and ammonium acetate precipitation, followed by treatment with DNase-free RNase, phenol/chloroform/isoamyl alcohol extractions and ammonium acetate precipitation (Ausubel, F. M. et al., Current Protocols in Molecular Biology, John Wiley and Sons, Inc. 1993)).

TABLE 1

Selected Plasmids Used in Present Studies

| Plasmid Name | Promoter | Genomic Elements |
| --- | --- | --- |
| PACMV-IL2 | CMV (immediate-early) | IL2, AAV |
| pBC12/CMV-IL2 | CMV (immediate-early) | IL2 |
| pA1CMVIX-CAT | CMV (immediate-early) | CAT, AAV |
| pADA-IL2 | ADA | IL2 |
| pTK-IL2 | TK | IL2 |
| pCMV-IL2 | CMV (immediate-late) | IL2 |
| pATC-Jgal | TK | Jgal, AAV |
| pAADA-Jgal | ADA | Jgal, AAV |
| pMP6-IL2 | CMV (early) | IL2, AAV |

E. Liposome Preparation

Small unilamellar liposomes were prepared from the cationic lipid dioctadecyl-dimethylammonium-bromide (DDAB) (Sigma) in combination with the neutral lipid dioleoyl-phosphatidyl-ethanolamine (DOPE) (Avanti Polar Lipids). Lipids were dissolved in chloroform. DDAB was mixed with DOPE in either a 1:1 or 1:2 molar ratio in a round-bottomed flask, and the lipid mixture was dried on a rotary evaporator. The lipid film was rehydrated by adding sterile double distilled water to yield a final concentration of 1 ml DDAB. This solution was sonicated in a bath sonicator (Laboratory Supplies, Hicksville, N.Y.) until clear. The liposomes were stored at 4° C. under argon gas. For in vivo use of liposomes via intravenous administration, a DDAB-:DOPE ratio of 1:4 to 1:5 is used. For intraperitoneal administration, a DDAB:DOPE ratio of 1:1 to 1:2 is used.

F. Preparation of Recombinant AAV (rAAV) for Transduction with Viral Infection

For the preparation of recombinant AAV stocks, cells of the 293 cell line were split and grown to approximately 30–50% confluence. Thereupon, the cells were infected with adenovirus type 5 at a multiplicity of infection of 1 to 5, and incubated at 37° C. After 2 to 4 hours, the infected cells were cotransfected with 10 μg of a plasmid comprising a gene of interest and 10 μg of the rep capsid complementation plasmid, pΔBal, per 100 mm tissue culture dish ($0.5–1\times10^7$ cells). Calcium phosphate coprecipitation was used for transfection (Hermonat, P. L. et al., *Proc. Natl. Acad. Sci. USA* (1984) 81:6466–6470). At 12 to 18 hours after transfection, the medium was removed from the cells and replaced with 5 ml of DMEM medium containing 10% FBS.

At 48 to 72 hours after transfection, AAV was harvested according to the following procedure: Cells and medium were collected together, and frozen and thawed three times to lyse the cells. The suspension of cells and medium was then centrifuged to remove cellular debris, and the supernatant was incubated at 56° C. for 1 hour to inactivate adenovirus (Hermonat, P. L. et al., supra; Tratschin, J. D. et al., *Mol. Cell. Biol.* (1985) 5:3251–3260). After heat inactivation, the virus-containing supernatant was filtered through cellulose acetate filters (1.2 Tm). Viral stocks were then stored at −20° C. One ml of AAV supernatant was used to transduce $10^6$ cells.

G. Cellular Transfection ("Lipofection")

For primary tumor cells and the rat tumor cell lines (R3327 and M3T-2), $10^6$ cells were plated in 2 ml serum-free media per well of a 6 well dish. Thereafter, 5 μg AAV plasmid DNA was mixed with 5 nmoles DDAB as liposomes composed of DDAB and DOPE in a 1:2 molar ratio, respectively. Serum-free media (0.5 ml) was added to the AAV:liposome complex, which was then transferred to the cells. To effect lipofection, the cells were incubated at room temperature for minutes, then FBS was added to the cells to yield a final concentration of 5%.

For T cells, $5–10\times10^6$ cells were plated in 1 ml of serum-free medium per well of a 6 well dish. 50 μg plasmid DNA was mixed with 50 nmoles of DDAB as liposomes composed of DDAB and DOPE in a 1:1 molar ratio. The transfections ("lipofections") were then performed as for tumor cells.

For stem cells, $1–2\times10^6$ cells were transfected with complexes comprising 10 μg plasmid DNA and 10 nmoles liposomes. The transfected cells were cultured with media containing stem cell factor, interleukin-3 (IL-3) and interleukin-1 (IL-1). On days 3 and 7, the cells were harvested and extracts were made.

H. IL-2 Assay

Cells were counted, and $1\times10^6$ cells were plated in 1 ml per well of a 24 well plate. The following day, supernatants were collected and assessed using a Quantikine® IL-2 ELISA kit (R&D Systems, Minneapolis, Minn.). IL-2 levels were defined as pg/ml supernatant.

I. J-Galactosidase Assay

The FluoReporter® lacZ gene fusion detection kit from Molecular Probes (Eugene, OR) was used to quantitate lacZ J-D-galactosidase in single cells by measurement of the fluorescence of the enzyme hydrolysis product, fluorescein. The AAV/J-gal plasmids (pATK-Jgal and pAADA-Jgal) were used with this kit. Fluorescein is produced by enzymatic cleavage of fluorescein di-J-D-galactopyranoside (FDG) in cells that express the marker gene lacZ encoding J-D-galactosidase. The cells were analyzed by flow cytometry (FACScan®, Becton Dickinson. San Jose. Calif.)

Results

A. Level of IL-2 Gene Expression by Use of AAV Plasmid: Cationic Liposome Complex To evaluate the gene transfer efficiency of AAV plasmids, the IL-2 gene transfer efficiencies of AAV plasmids were compared to the efficiencies of standard plasmid constructs. The standard plasmids carried the IL-2 gene, with an adenosine deaminase (ADA) promoter (pADA-IL2), a thymidine kinase (TK) promoter (pTKIL-2), or the immediate-late cytomegalovirus (CMV) promoter (pCMV-IL2). An AAV IL-2 study plasmid (pACMV-IL2) contained the CMV promoter (immediate early), with the IL-2 gene placed downstream of the promoter (FIG. 1). As shown in FIG. 1, the corresponding control plasmid, pBC12/CMV-IL2, was identical to pACMV-IL2, but lacked the AAV ITRs.

For comparison, five plasmids (pACMV-IL2, pBC12/CMVIL2, pADA-IL2, pTK-IL2, pCMV-IL2) containing the IL-2 gene were complexed with liposomes and tested for transfection efficiency on the two cultured tumor cell lines: the rat bladder (MBT-2) and the rat prostate (R3327) cell lines. The cell lines were transfected with 10 μg of plasmid DNA complexed to 10 nmoles of liposomes per $1\times10^6$ cells. Supernatants were collected on day 3 and tested for the levels of IL-2 using an IL-2 ELISA kit.

The AAV plasmid (pACMV-IL2) induced the highest levels of expression in both cell lines (FIG. 4a). The IL-2 gene with an ADA promoter (pADA-IL2) induced the least amount of expression in both cell lines. As shown in FIG. 4a, both TK and CMV (immediate-late promoter) IL-2 constructs induced comparable levels of IL-2 expression in both cell lines. However, the pBC12/CMV-IL2 plasmid, which contained CMV immediate-early promoter showed higher levels of gene expression in the prostate cell line when compared to the bladder cell line. Among the plasmids tested, the AAV IL-2 study plasmid induced the highest level of expression in both cell lines, with a significant level of increase observed in the prostate cell line.

The duration of expression induced by the corresponding control plasmid (pBC12/CMV-IL2) and the AAV IL-2 study plasmid (pACMV-IL2) in the prostate cell line R3327 were studied (FIG. 4b). Expression was assessed up to 30 days in these cultures without any selection. The cells were seeded at $10^6$/ml and supernatants were collected for analysis every 24 hours. The cells doubled every 48 hours in culture. The data in FIG. 4b indicate that, in addition to the enhanced levels of expression, the duration of expression lasted 30 days post-transfection with AAV plasmid (PACMV-IL2). Notably, significant expression continued throughout—the full duration of the time period of evaluation. As shown in FIG. 4b, both plasmids induced maximum levels of expression between day 2 and day 7, by day 15 IL-2 levels declined and then were maintained at approximately 100 pg/ml only in the AAV plasmid transfected group. Similar, sustained levels of expression were observed in the bladder cell line, as well as with cells from primary lung, breast and ovarian tumor, when AAV plasmid:liposome complexes were used for transfection.

B. Comparison of AAV Plasmid:Liposome Transfection "Lipofection" and Recombinant AAV Transduction The prostate and bladder cell lines were transfected and transduced, to determine whether optimal AAV:liposome transfection was comparable to optimal recombinant AAV transduction. For optimal transfection, 10 μg of AAV plasmid DNA was complexed to 10 nmoles of liposomes per $10^6$ cells in 2 ml final volume. For maximal rAAV transduction, 2 ml of the viral supernatant was added to $10^6$ cells in 1 ml of complete media. After 24 hrs, the cells were washed and resuspended in fresh complete media. Supernatant fluids were collected at various time points after transfection and transduction.

In the prostate line (FIG. 5a), transfection induced higher levels of expression than AAV transduction under test conditions (2 ml of viral supernatant for $10^6$ cells, versus 10 μg DNA:10 nmoles of liposomes). Although results on day 3 through day 5 showed approximately 10-fold higher levels of IL-2 with transfection, by day 20 comparable levels were observed in both transfected and transduced groups.

Transduction with recombinant AAV initially induced higher levels of IL-2 production in the bladder cell line, as compared to transfection using liposomes (FIG. 5b). Similar to the prostate cell line, transduction of the bladder cell line also showed a decline in IL-2 levels by Day 20, although IL-2 levels from transfection increased during this period; comparable levels of IL-2 were produced through Day 33 in both transfected and transduced groups.

C. Transfection of Primary Tumor Cells Using AAV Plasmid DNA:Liposome Complexes

In the foregoing experiments, significant transgene expression was demonstrated in cultured cell lines. In order to assess whether cationic liposome:AAV plasmid DNA complexes also mediated comparable transgene expression in freshly isolated primary tumor cells, cells of four different primary tumors were transfected with AAV IL-2 plasmids using liposomes. Tumor cells were cultured in RPMI-1640 media supplemented with 10% FBS for 2–3 weeks prior to the transfection. The cells were plated at $10^6$ cells per ml and transfected with 10 μg DNA complexed with 10 nmoles liposomes. Supernatants were collected on days 2 and 3.

As shown in FIG. 6, all four primary cell types produced significant levels of IL-2 after transfection. The highest level of expression was observed on day 3 during the day study period (lung and one breast sample were studied for longer periods). IL-2 gene expression was followed in cells of the lung tumor and in cells of one of the breast tumors as long as 25 days after transfection in culture. The levels on day were equivalent (100 pg/ml IL-2) in both cell lines, and in the cells derived from primary tumors.

D. Effect of Lethal Irradiation on Transgene Expression

To determine the effect of irradiation on gene expression, the prostate cell line (FIG. 7a) and cells of a primary breast tumor (FIG. 7b) were transfected and assessed for gene expression after lethal irradiation. Both cell types were transfected using optimal AAV plasmid:liposome complexes. On the second day after transfection, an aliquot of each culture was subjected to 6000 rad using a $^{60}$Co irradiator, whereby cellular division is abolished, and the aliquots were then kept in culture. One-half of each culture was maintained as a non-irradiated control. The aliquots were subjected to 6000 rad using a $^{60}$Co irradiator, while the expression level of IL-2 was approximately 300–400 pg/ml. Supernatants were collected 24, 48, 72 and 96 hrs after irradiation, and tested for IL-2 levels.

As shown in FIGS. 7a–7b, lethal irradiation after transfection did not inhibit transgene expression. Neither the prostate cell line nor the primary tumor cells exhibited any change in IL-2 expression after irradiation. Thus, although cellular division was abolished, IL-2 secretion was not sensitive to irradiation. This is advantageous, since many gene therapy strategies involve gene delivery to primary T lymphocytes (which do not generally divide absent activation) and often cannot be transduced via viral infection.

E. Level of B-D-Galactosidase Gene Expression by Use of AAV Plasmid:Liposome Complex To demonstrate the expression levels on a per cell basis, the J-gal gene was used for transfection experiments. Each of two AAV J-gal plasmids (pATK-Jgal and pAADA-Jgal) were complexed with cationic liposomes and used for transfection of the prostate cell line. Ten μg pATK-Jgal or pAADA-Jgal plasmid DNA was complexed with 10 nmoles liposomes and the complexes used to transfect $10^6$ cells in 2 ml volume. At various time points, approximately $5\times10^5$ cells were harvested and stained with fluorescent substrate FDG and analyzed by flow cytometry.

Maximum transgene expression was observed between day 7 and day 15 (FIG. 8). Significant levels of J-gal activity were observed through Day 25. Flow cytometry analysis of J-gal$^+$ cells showed maximal levels of 10 to 50% transfection efficiency with both plasmid constructs. The levels declined to 5 to 10% by day 25. The expression pattern and duration was similar to that of IL-2 expression as set forth above.

F. Transgene Expression Induced by AAV Plasmid:Liposome Complex in Freshly Isolated Peripheral Blood T Cell Subpopulations The effect of AAV plasmid:liposome complex in transfecting freshly isolated human peripheral blood T cell populations was examined. The gene for the CAT enzyme was used as the reporter gene in the pA1CMVIX-CAT plasmid (FIG. 1). The pA1CMVIX-CAT constructs were made using the AAV backbone (pA1) with CMV immediate-early promoter enhancer sequences and CAT gene. Total and purified CD4$^+$ and CD8$^+$ subpopulations of T cells were used for transfections. Both total (CD3- or CD5/8-selected) and purified (CD4- or CD8-selected) subpopulations of T cells (FIG. 9a–d), as well as CD34$^+$ stem cells (FIG. 10; see Section G. below) showed significant levels of CAT gene expression.

Primary T cells freshly isolated from peripheral blood were tested for transgene expression using AAV plasmid DNA:liposome complexes. Results of thin layer chromatography (TLC) assays for CAT activity from CD3$^+$ T cells, CD5/8-selected T cells (total T cells), the CD4$^+$ T cells, and CD8$^+$ T cells are depicted in FIG. 9a–9d, respectively.

T lymphocytes were fractionated as CD3$^+$, or CD5/8$^+$ or CD4$^+$ or CD8$^+$ populations using AIS MicroCELLector® devices. The relevant cells were captured and nonadherent cells were removed by washing. The adherent cells were removed from the devices after 2 days in culture with RPMI-1640 and 10% FBS. Five to $10\times10^6$ cells were plated and transfected with 50 μg AAV plasmid DNA and 50 or 100 nmoles liposomes to obtain 1:1 or 1:2 DNA:liposome ratios. The cells were harvested 3 days after transfection, the cell extracts were normalized by protein content and CAT activity was measured using a TLC assay. Blood was obtained from donors referred to as A or B. Peripheral blood of donor A or B was used to isolate the T cells, and for transfection.

As depicted in FIGS. 9a–9d, the lipid composition of the liposomes comprising AAV was varied, as was the ratio of DNA to liposome. In the study of CD3$^+$ T cells (FIG. 9a) cells from donor A were employed. For the studies of CD5/8 selected T cells (FIG. 9b), CD4$^+$ T cells (FIG. 9c), CD8$^+$ T cells (FIG. 9d), and CD34$^+$ stem cells (FIG. 10) were derived from two donors (A and B).

TABLE 2

Conditions Employed for Studies Depicted in FIG. 9a

| Condition | Parameters |
|---|---|
| 1 | pA1CMVIX-CAT + DDAB:DOPE (1:1), DNA:liposome ratio (1:1) |
| 2 | pA1CMVIX-CAT + DDAB:DOPE (1:1), DNA:liposome ratio (1:2) |
| 3 | pA1CMVIX-CAT + DDAB:DOPE (1:2), DNA:liposome ratio (1:1) |
| 4 | pA1CMVIX-CAT + DDAB:DOPE (1:2), DNA:liposome ratio (1:2) |

TABLE 3

Figure 9B:
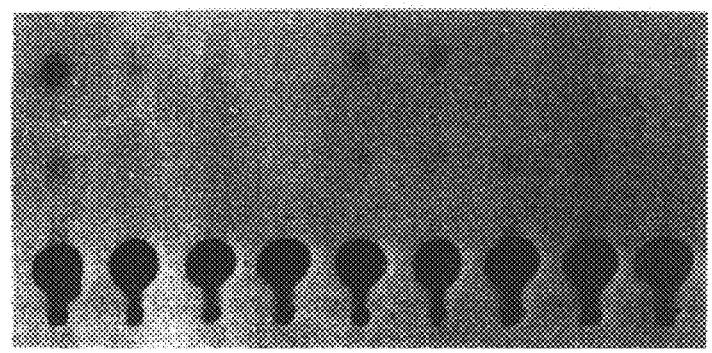
Figure 9C:
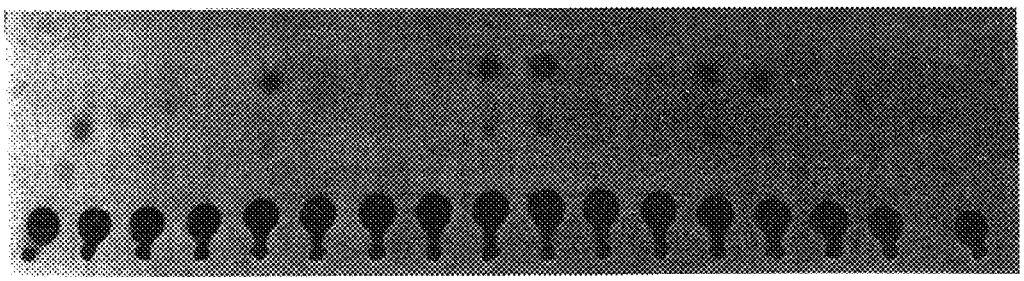
Figure 9D:

Conditions Employed for Studies Depicted in FIGS. 9b–d

| Condition | Parameters |
|---|---|
| 1 | pA1CMVIX-CAT + DDAB:DOPE (1:1), DNA:liposome ratio (1:1) |
| 2 | pA1CMVIX-CAT + DDAB:DOPE (1:1), DNA:liposome ratio (1:2) |
| 3 | pA1CMVIX-CAT + DDAB chol (1:1), DNA:liposome ratio (1:1) |
| 4 | pA1CMVIX-CAT + DDAB chol (1:1), DNA:liposome ratio (1:2) |

TABLE 4

Figure 10:
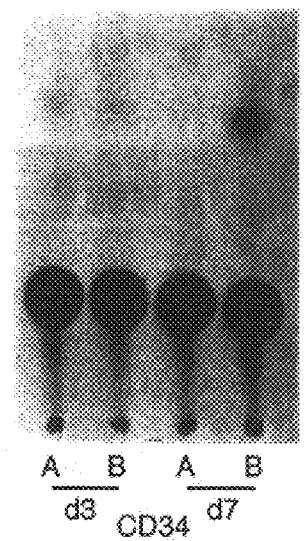
FIG. 10 shows TLCs of peripheral blood $CD34^+$ stem cells transfected with AAV plasmid:liposomes. The cells were harvested on day 3 and day 7 after transfection. Normalized amounts of protein from the extracts were assayed for CAT activity using TLC.

Condition Employed for Studies Depicted in FIG. 10

| Condition | Parameters |
|---|---|
| 1 | pA1CMVIX-CAT + DDAB:DOPE (1:1), DNA:liposome ratio (1:1) |
| 2 | pA1CMVIX-CAT + DDAB:DOPE (1:1), DNA:liposome ratio (1:2) |

For the studies depicted in FIGS. 9a–d, maximum levels of expression were observed on days 2 and 3 in both total and purified subpopulations. Significant levels of expression were detected up to day 14. The cells were harvested 3 days after transfection, and normalized protein content from each extract was analyzed for CAT activity. The same composition of liposome, and the DNA:liposome ratio induced similar levels of expression in all the populations.

G. Transgene Expression Induced by AAV Plasmid:Liposome Complex in Freshly Isolated CD34+ Stem Cells The effect of AAV plasmid:liposome complex in transfecting freshly isolated human peripheral blood CD34+ stem cells was examined. The CAT gene was used as the reporter gene in the pA1CMVIX-CAT plasmid (FIG. 1). The pA1CMVIXCAT constructs were prepared as described above. The level of CAT expression as determined by TLC from CD34+ stem cells is shown in FIG. 10.

Freshly isolated CD34+ peripheral blood stem cells were transfected with AAV CAT plasmid DNA:liposome complexes. CD34+ cells were purified from peripheral blood using AIS CD34 MicroCELLectors® after removing essentially all the T cells using CD5/8 MicroCELLector® device. The stem cells were removed from the device and 0.5–1×10⁶ cells were transfected with complexes comprising 10 μg plasmid DNA and 10 nmoles liposomes. The transfected cells were cultured with medium containing stem cell factor, IL-3 and IL-1. On Day 3 and 7, the cells were harvested and extracts were made. Normalized protein content from the extract was assayed for CAT activity. As shown in FIG. 10, there were significant levels of CAT gene expression in the CD34+ peripheral blood stem cells.

H. Integration Studies

Figure 11A:
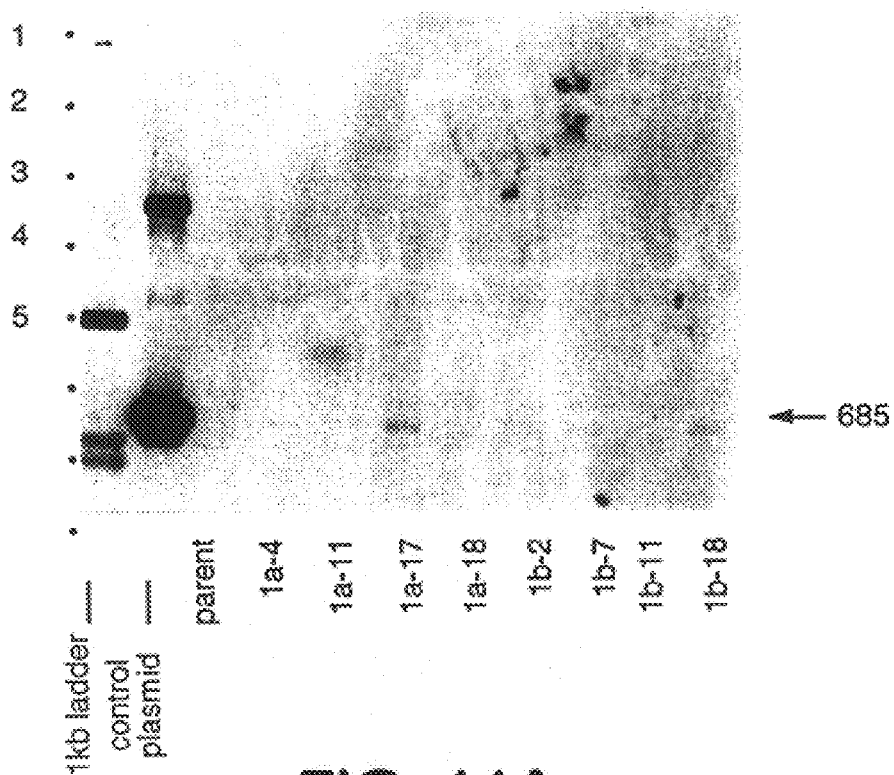
FIGS. 11a–11b shows results of enhanced chemiluminescence (ECL) Southern analysis of genomic DNA from clones transfected with AAV plasmid DNA:liposome complexes.
Figure 11B:
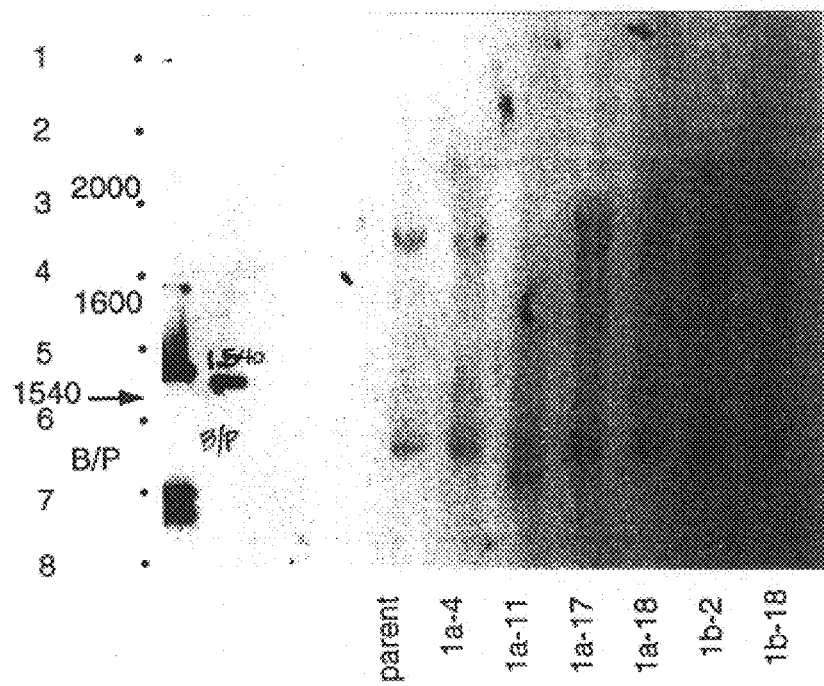

FIGS. 11a–11b illustrate enhanced chemiluminescence (ECL) Southern analyses of genomic DNA from stable clones (clones stable at least beyond day 30) that were transfected with AAV plasmid DNA:liposome complexes in accordance with the invention. Genomic DNA was isolated and analyzed using the ECL direct nucleic acid labelling and detection system (Amersham). IL-2 probe was prepared from the 0.685 kb IL-2 gene from pACMV-IL2. After hybridization, the membrane was washed twice in 0.5×SSC/0.4% SDS at 55° C. for 10 minutes and twice in 2×SSC at room temperature for 5 minutes.

In FIG. 11a, samples were digested with BamHI and HindIII and probed with IL-2. As shown in FIG. 11a, all clones showed the presence of the IL-2 gene, as demonstrated by the 0.685 kb band in BamHI and HindIII digested genomic DNA.

For the results shown in FIG. 11b, samples were digested with BamHI and probed with IL-2. Again, all clones showed IL-2 gene integration. As shown in FIG. 11b, integration of IL-2 was demonstrated by the high molecular weight bands (between 1.6 and 2 kb), bands which is consistent with integration of the gene in conjunction with attached host genomic material obtained via digestion. The results in FIG. 11b indicate that there was more than one integration site, since there were multiple high molecular weight bands in the BamHI digested genomic DNA. Furthermore, the integration site was shown to be in different locations in different clones, as demonstrated by the different size bands in the digested clones (FIG. 11b).

Figure 12A:
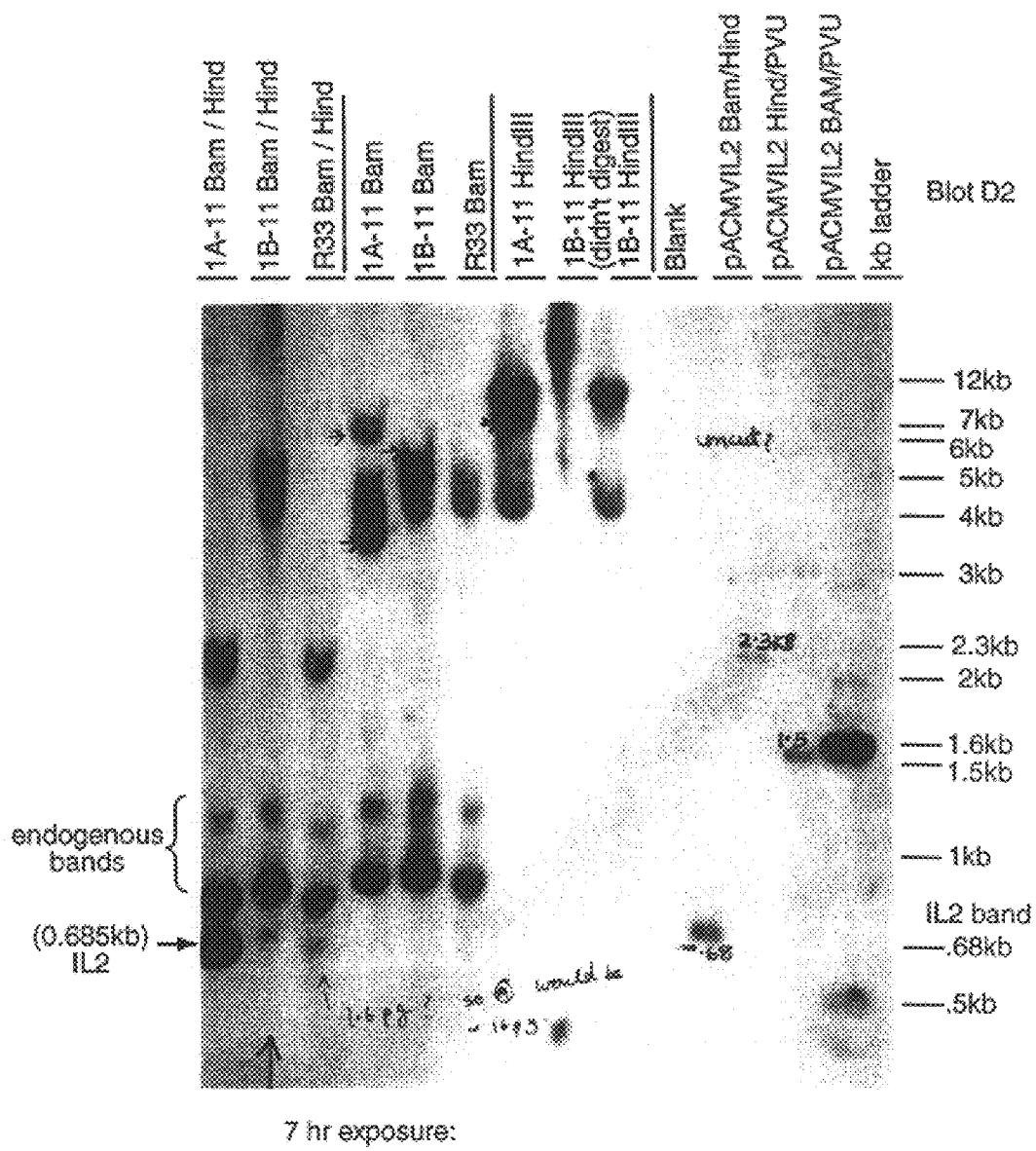
FIGS. 12a–12b show results of Southern analysis ($^{32}$P) of clone 1A11 and 1B11. After Southern blotting, the filter depicted in FIG. 12a was probed with a 0.68 kb IL2 BamHI/HindIII fragment of pACMV-IL2.
Figure 12B:
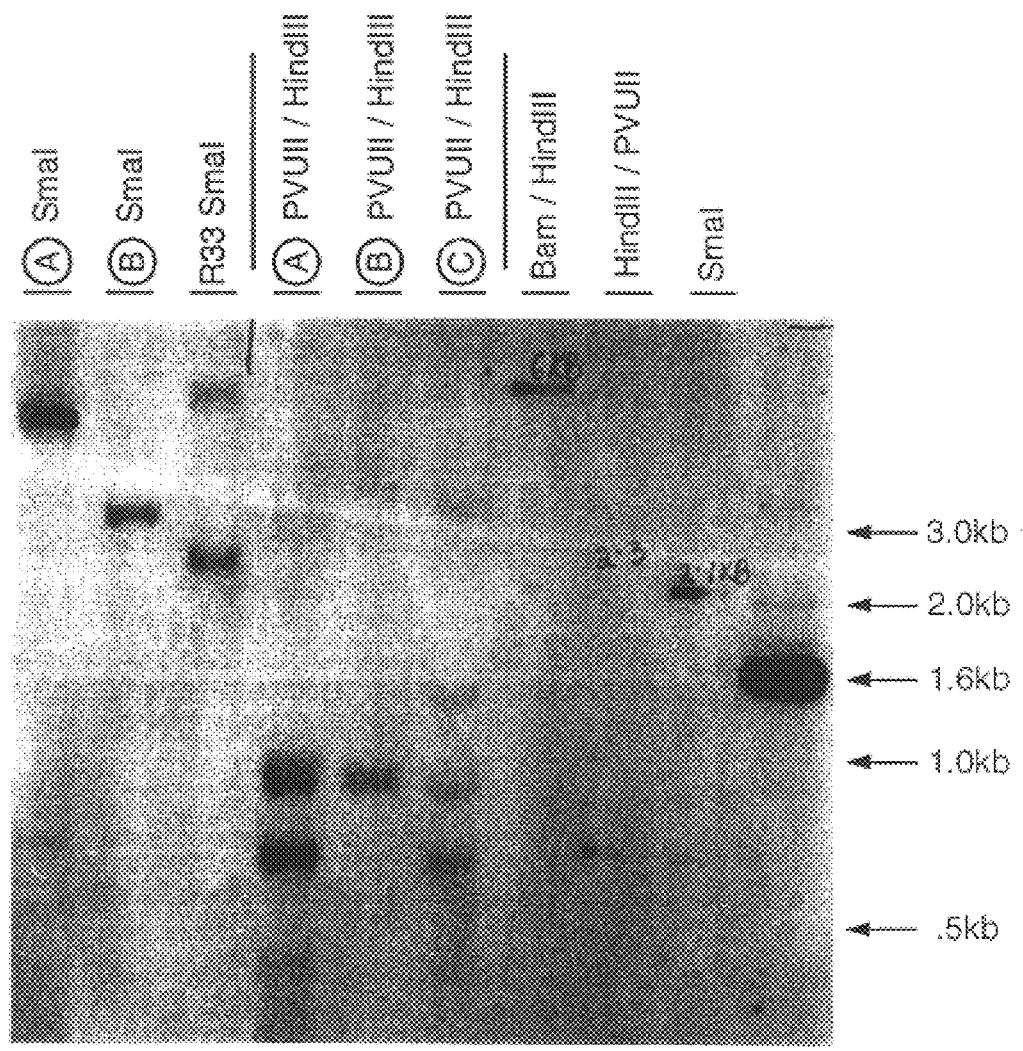

FIGS. 12a–12b depict chromosomal DNA analyses, using a $^{32}$P Southern assay, of two clones obtained from the present study. Nuclear DNA was isolated from the two IL-2 clones (1A11 and 1B11) using the Hirt fractionation protocol. As a negative control, total DNA was isolated from untransfected cells of the R3327 cell line. After restriction enzyme digestion, 10 μg of each sample, along with appropriate plasmid controls, were loaded onto a 1% agarose gel, electrophoresed, denatured and transferred onto Hybond+ membrane. The filters were hybridized overnight at 68° C. with DNA fragments labelled with $^{32}$P by random priming. The membranes were then washed twice at 68° C. for 30 minutes each with 2×SSC, 0.1% SDS and 0.2×SSC, 0.1% SDS. Autoradiograms of these filters were exposed on x-ray film.

In the study shown in FIG. 12a, the IL-2 gene was again used as the probe. After Southern blotting, the filter was probed with a 0.685 kb IL2-BamHI/HindIII fragment of pACMV-IL2. The results indicate that the number of integrated copies of the IL-2 gene varied from clone to clone, as evidenced by the various densities of the 0.685 kb band in the digests of cells of the two clones (see description of this drawing, supra). Higher molecular weight bands were also demonstrated, consistent with integration of the IL-2 gene together with host genomic material obtained from the various digest protocols.

FIG. 12b shows results of a study in which the filter was probed with a 0.85 kb PvuII/HindIII (AAV ITR/CMV) fragment of the plasmid pACMV-IL2. The presence of the 0.8 kb band in the SmaI and PvuII digested chromosomal DNA demonstrates the presence of the right AAV ITR. The presence of the 2.1 kb band in the SmaI and PvuII digested chromosomal DNA indicates the presence of the left AAV ITR in clone A.

EXAMPLES

A method in accordance with the invention utilizes liposomes comprising AAV viral material to deliver genes for cytokines, costimulatory molecules such as B7, and MHC class I antigens into a wide variety of cell types. For example, DNA encoding any of the foregoing proteins or peptides is delivered into primary tumor cells or tumor cell lines such that when this introduced DNA is expressed, the modified tumor cells serve as a tumor vaccine. Furthermore, DNA encoding any of the foregoing proteins or peptides is delivered into peripheral blood cells or bone marrow cells to treat hematologic or neoplastic diseases or conditions.

The present invention provides a method by which liposomes containing AAV viral material are used to deliver and express (a) genes encoding proteins or peptides, (b) anti-sense DNA or RNA oligonucleotides, or (c) RNA. Expression of such proteins/peptides, anti-sense oligonucleotides or RNA in a subject modulates the subject's immune response. The term "modulate" includes inducing, augmenting, suppressing or preventing the immune response.

Accordingly, HIV infection is treated by delivery of anti-sense oligonucleotides, RNA, or ribozymes that have been expressed in accordance with the invention.

Additionally, an anti-tumor immune response is modulated using peptides or RNA expressed in accordance with the invention to enhance reactivity to tumor-specific and/or tumor-associated antigens. Non-immunogenic or weakly immunogenic tumors are rendered immunogenic by delivery of DNA or RNA according to the invention such that the tumors induce a cytolytic T cell response or other forms of anti-tumor immunity in vivo and in vitro.

The method of this invention is used to deliver genes to primary lymphoid cells, including B lymphocytes or T lymphocytes. In another embodiment, genetic material is delivered to $CD34^+$ stem cells. The genes delivered to and expressed in the lymphoid cells or stem cells result in modified cells which are used to treat any of a variety of diseases and conditions including HIV infection, genetic defects, neoplasias, and autoimmunity. The conditions to be treated are those wherein expression of a gene of interest is desired, as is appreciated by one of ordinary skill in the art. For example, for treatment of a malignant neoplastic condition, the MDRI gene is delivered and expressed in cells of the tumor in accordance with the invention, resulting in a therapeutic effect.

In another example, $CD8^+$ cells are selected with AIS MicroCELLectors®. These $CD8^+$ cells are obtained, for example, from the peripheral blood of subjects infected with HIV or from tumor tissue of cancer patients. These T cells are then activated according to methods known in the art, such as by use of polyclonal T cell activating substances including IL2, phytohemagglutinin (PHA) and Concanavalin A (Con A). The activated $CD8^+$ T cells are grown in culture for about 20 days. Thereafter, the cells are transfected in accordance with the invention, with AAV:liposome complexes comprising IL-2 genomic material. The cells originally obtained from a given subject are returned to the subject after transfection according to this invention. As a result of the expressed IL-2 gene, the need for subsequent administration of IL-2 to the patient to maintain cytotoxic T cell activity is reduced or eliminated, thereby reducing or eliminating the undesired side effects and possible lethal dose-related toxicity of IL-2 infusion.

A. Tumor Vaccination

Conventional tumor vaccination protocols employ non-proliferating neoplastic cells in which proliferation is prevented by exposure of the cells to radiation, chemical inhibitors or exposure to high pressure chambers. It is believed that the body is able to mount an effective antitumor response to neoplastic cells present in the body (apart from initial tumor masses or foci).

Past tumor vaccination trials have used genetically-modified tumor (GMT) in efforts to enhance tumor cell antigenicity in melanoma and renal cell cancer patients. These trials have relied upon ex vivo retroviral gene transfer, which suffers from the disadvantages that it is very complex and requires active cell division of the cells being transfected to achieve incorporation and expression of the delivered genes. Moreover, it can be very difficult to culture sufficient numbers of neoplastic cells ex vivo to provide a suitable quantity of therapeutic product.

In contrast to retroviral gene transfer, plasmid constructs possessing the terminal repeat elements of AAV at sites 3' and 5' to the gene to be transduced were expressed efficiently when introduced via nonviral liposome-mediated transfer. For example, as discussed in greater detail below, liposomes were used to deliver AAV plasmid, such as pMP6-IL2, that comprised cDNA encoding IL-2 into primary human tumor cells, such as melanoma cells. The primary tumor cells then expressed IL-2. Tumor cell lines were also effectively transfected.

The expression of IL-2 following AAV-liposome transfection has been durable and high level. The levels of cytokine secretion from cells genetically modified by AAV plasmid-liposome compositions has exceeded the levels obtained from retrovirally infected cells.

Accordingly, cells are genetically modified using a composition comprising AAV plasmid and liposomes; these modified cells are utilized in therapeutic tumor vaccination regimens. Advantageously, such a gene modification method as disclosed herein successfully modified primary tumor cells. This is an important development because it obviates the need to first establish a tumor cell line from primary tumor cells in order to effect gene modification which process was required prior to the present invention. It is highly advantageous that tumor cells that are genetically modified to express IL-2, when infused into a patient in a therapeutic regimen, do not require co-administration of systemic IL-2 which is known to cause extremely serious side effects and possibly death.

B. Lipofection of Cells with Transgene DNA for Use in Therapeutic Administration Systemic IL-2 is currently used to treat certain serious conditions such as cancer. Additionally, activated T cells become dependent on exogenous IL-2 for their growth and survival both in vitro and in vivo. When the IL-2 stimulus is withdrawn, the T cells undergo apoptosis (DNA fragmentation) and death within a few days. Systemically administered IL-2 is, however, known to cause severe side effects, including death. There is a need, therefore, to develop therapies which eliminate or decrease dependence on systemic IL-2 administration.

The studies presented below addressed the delivery into T cells of AAV plasmid DNA and transgene DNA using a novel system that does not involve viral transduction. More particularly, the present results show successful transfection utilizing the elegant carrier system of lipofection and the proficient transduction capability of AAV plasmid constructs.

An AAV plasmid containing a transgene and AAV terminal repeats was used as a DNA vector, and cationic liposomes were used as carrier molecules. (For a general discussion of transfection and expression in T lymphocytes, see, Philip et al., *Mol. Cell. Biol.* (1994) 14:2411–2418.) In a preferred embodiment, the transgene encodes IL-2. AAV plasmid:liposome complexes induced levels of transgene expression comparable to levels obtained by recombinant AAV transduction. Advantageously, the cationic liposomes facilitated the entry of AAV plasmid DNA into cells in the absence of rep and capsid transcomplementation, recombinant virus or wild-type AAV. The AAV plasmid DNA:liposome complexes efficiently transfected TILs. AAV plasmid DNA complexed with liposomes provided several-fold higher levels of expression than complexes with standard plasmids. Moreover, expression lasted for a period of 30 days without any selection.

The IL-2 gene expression system for T cells disclosed herein enables activated cells to produce sufficient endogenous IL-2 to support their maintenance in vivo thereby preventing apoptosis and obviating the need for systemic IL-2 administration.

In a controlled study, various T cell populations were transfected with an AAV plasmid, carrying IL-2 cDNA, complexed to liposomes. These cell populations were tested for their ability to maintain growth and proliferation without exogenous IL-2 in vitro.

For T cells, assays showed that when transfected with the IL-2 gene, primary and activated $CD8^+$ T cells proliferate to attain higher numbers of cells than "control" transfected with an irrelevant "control" gene or DNA sequence.

IL-2-transfected $CD8^+$ cells grew in culture without a need for exogenous IL-2, and apoptosis was significantly reduced. Southern blot analysis of such transfected T cells showed the presence of the IL-2-encoding plasmid for up to 25 days. These results demonstrated that transfer of the IL-2 gene into ex vivo-activated and expanded $CD8^+$ cells promoted the growth of such cells and prevented their apoptotic death, without the need for exogenous IL-2.

Cells that can be genetically modified according to the present invention include, but are not limited to: primary lung, ovarian and breast carcinoma cells, melanoma cells, autologous fibroblasts, transformed B cells, dendritic cells and cells of any desired cultured cell line. Such genetically modified cells can be used alone or in conjunction with tumor cells (unmodified or genetically modified) to stimulate TIL. Genetically modified cells have be made to express tumor-associated antigens, including HER2, K-ras, mucins useful as stimulatory antigens for TILs or other T lymphocytes in culture. T cells, including non-MHC-restricted T cells are generated in response to mucin antigens, such as human mucin 1 (MUC1) present on the core protein of mucin and may be specific for a peptide epitope thereof appearing as a variable number of tandem repeats having the amino acid sequence PDTRPAPGSTAPPAHGVTSA (SEQ ID NO:3). MUC1 is expressed on adenocarcinomas of the breast, pancreas and ovary and in multiple myeloma. CTL specific for these antigens on various types of tumor cells have been found in patients with the foregoing cancers and can be found in lymph nodes or generated from blood lymphocytes (Barnd, D. L. et al., Proc. Natl. Acad. Sci. USA 86:7159 (1989); Jerome, K. R. et al., Canc. Res. 51:2908 (1991); Ioannides, C. G. et al., J. Immunol. 151:3693–3703 (1993); Finn, O. J., Biotherapy 4:239 (1992); Jerome, K. R. et al., J. Immunol. 151:1654–1662 (1993); Takahashi, T. et al., J. Immunol. 153:2102–2109 (1994), which references are hereby incorporated by reference). Target cell can be transfected to express MUC1 (Jerome et al., 1991, 1993, supra).

Moreover, known types of APCs, such as transformed B cells and dendritic cells, can be genetically modified to express tumor-associated antigenic peptides such as MAGE-1 and MART-1 for presentation to and stimulation of TILs in culture. The present invention as described herein enables the efficient transfection of,T cells or neoplastic cells wherein the transfected DNA is expressed both transiently and for a sustained duration. The transfection described herein occurred in the absence of any recombinant virus (producible from rep and capsid particles in adenovirus-infected cells). The cells obtained by AAV transfection according to this invention are used to treat patients and achieve notable therapeutic benefit.

1. Reactant Preparation and Protocols
    a. Plasmids
    i. Plasmid pACMV-IL2

Plasmid pACMV-IL2 contains the human IL-2 gene as IL-2 CDNA, and the immediate-early promoter-enhancer element of the human cytomegalovirus (CMV), and rat preproinsulin and SV40 polyadenylation sequences, flanked by AAV ITRs at both ends. A corresponding control plasmid, pBC12/CMV-IL2, was identical to pACMV-IL2 but lacked the AAV terminal repeats. FIG. 1 depicts plasmid maps of pACMV-IL2 and pBC12/CMV-IL2.

ii. Plasmid pMP6-IL2

As shown in FIG. 2, plasmid pMP6-IL2 is a double stranded circular plasmid in which the human IL-2 gene is under the control of a CMV promoter and a SV40 polyadenylation signal. Between the promoter and the coding sequences of IL-2, there is an intron which enhances the expression of IL-2. The whole expression cassette is between the left and right terminal sequences of AAV. The pMP6-IL2 plasmid also has a Bluescript backbone; the backbone has a Col-E1 bacterial origin of replication and an ampicillin resistance gene which facilitates the propagation of this plasmid in *E. coli*.

FIGS. 3a–3e depict the DNA sequence of the pMP6-IL2 plasmid (shown in successive portions). In these Figures, portions of the pMP6-IL2 sequence which correspond to known DNA sequerces are indicated; the corresponding sequence information is listed directly beneath sequence information for the pMP6-IL2 plasmid. Unmarked sequences are from linkers.

The pMP6-IL2 plasmids were purified by alkaline lysis and ammonium acetate precipitation. The concentration of nucleic acid was determined by absorption at 260 nm.

iii. Plasmid pA1CMVIX-CAT

Plasmid pA1CMVIX-CAT contains the CMV promoter enhancer element, the intervening splice acceptor sequences, the bacterial CAT gene and the simian virus 540 late polyadenylation signal flanked by AAV terminal repeats in a pBR322 derivative. Plasmids were purified by alkaline lysis and ammonium acetate precipitation. Nucleic acid concentration was measured by absorption at 260 nm.

b. Liposome Preparation
i. Liposomes used with pACMV-IL2

Small unilamellar liposomes were prepared from the cationic lipid, dioctadecyl-dimethyl-ammonium-bromide (DDAB) (Sigma Chemical Co.), in combination with the neutral lipid, dioleoyl-phosphatidyl-ethanolamine (DOPE) (Avanti Polar Lipids). The lipids were dissolved in chloroform. DDAB was mixed with DOPE in a 1:1 molar ratio in a round-bottomed flask. The lipid mixture was dried on a rotary evaporator. The lipid film was rehydrated by adding sterile double distilled water to yield a final concentration of 1 ml DDAB. This solution was sonicated in a bath sonicator until clear. The liposomes were stored at 4° C. under argon gas.

ii. Liposomes used with pMP6-IL2

Liposomes were prepared by combining the cationic lipid DDAB with the neutral lipid DOPE in a 1:1 molar ratio; or by combining DDAB with cholesterol in a 1:0.6 molar ratio, and evaporating the lipids to dryness in a rotary evaporator. The lipids were resuspended in sterile deionized water to yield a concentration of 1 mM DDAB and then sonicated to clarity in an ultrasonic bath. Liposomes were stored under argon gas at 4° C. and were stable for at least 4 months.

iii. Liposomes used for TIL stimulation

Liposomes were prepared by combining the cationic lipid DDAB with either the neutral lipid DOPE or cholesterol in a 1:1 or 1:2 molar ratio and evaporating the lipids to dryness in a rotary evaporator. The lipids were resuspended in sterile deionized water to yield a concentration of 1 ml DDAB. The solution was then sonicated to clarity in an ultrasonic bath. Liposomes were stored under argon at 4° C. and were stable for at least 4 months.

C. Cell Preparation i. Isolation of TILs

TIL cells were selected with AIS MicroCELLectors®. The source material was tumor tissue or lymphatic tissue samples taken from cancer patients. The T cells were then activated according to methods known in the art such as stimulation by IL-2. The activated cells were grown for 20 days.

ii. Isolation of T cells and Neoplastic Cells

Primary T cell populations were isolated from peripheral blood mononuclear cells, and TIL and tumor cells were isolated by use of AIS MicroCELLector® devices. The cells were prepared for transfection by standard methods.

1) Neoplastic Cells from a Solid Tissue

To obtain a cell population for transfection, cells were obtained from solid primary or metastatic lesions, or from lymphatic tissues. For example, biopsies of breast tumors were obtained from patients undergoing surgery with a pre-operative diagnosis of suspected refractory or recurrent breast cancer. These studies were also successfully performed with cells from ovarian tumors. The biopsy tissue cores were divided into fragments which were processed for routine pathology by light microscopy and immunohistochemical analysis.

Freshly excised tumors were cut into 0.5 cm cubes. Up to 10 tumor tissue cubes were transferred to a 25 ml spinner flask containing 25 ml of AIM V media (GIBCO). The flask was placed in an incubator at 37° C. which contains 5% $CO_2$, and the flask was gently stirred at 100–120 RPM for 12–18 h. After incubation, any tissue that was not disaggregated was filtered, and cells in suspension were pelleted by centrifugation. The pelleted breast cancer cells were placed into tissue culture flasks (Falcon) in AIM V medium and were maintained in humidified air containing 5% $CO_2$ at a temperature of 37° C.

After 48 hours of culture in the serum-free medium, adherent and non-adherent cells were separated by aspirating the non-adherent cells. The non-adherent cells were washed and then recultured in a fresh flask. During reculture, the adherent cells were grown to confluence, removed with 0.05% trypsin and 0.02% EDTA, and passaged at high cell density into new flasks.

Alternatively, primary tumor cells of lung, ovarian and breast tumor origin were obtained from solid tumor samples and isolated as follows: The tumor was minced and subjected to enzymatic digestion for 2 hours. The tissue was homogenized and washed with PBS. Lymphocytes were separated from non-lymphoid cells by capture on AIS MicroCELLector-CD5/8® devices. The nonadherent population contained tumor cells which were cultured in RPMI 1640+10% FBS with L-glutamine and antibiotics.

2) Neoplastic Cells from a Fluid

As an alternate source of cells for transfection, autologous neoplastic cells were isolated from malignant ascites fluid or pleural effusions. Malignant ascitic or effusion fluid was centrifuged, and the cell pellet was resuspended in AIM V media. Cells were counted, and the lymphocyte population was depleted either by using a 2-step Ficoll gradient or by using AIS CELLector CD5/CD8® devices. The choice between these two methods was made based on the total cell number, as would be appreciated by one of ordinary skill in the art. Isolation of neoplastic cells from a fluid source is particularly important in malignancies such as ovarian and lung cancer which are known to result in pleural effusions. The T cell-depleted cell fraction was enriched in neoplastic cells.

All autologous neoplastic cells were characterized by light microscopy, flow cytometry and immunohistochemical staining to assess oncogene expression and to establish a proliferation index. For example, for studies of breast cancer, only cells with the morphology of breast cancer cells or that stained with breast cancer-specific antibodies were deemed autologous tumor cells and utilized as such.

3) Cell Lines

Cells of the murine B lymphoma cell line 38C13 were provided by Dr. Bernd Gansbacher (Memorial-Sloan Kettering Cancer Center); rat prostate cell line R3327 cells were provided by Dr. Eli Gilboa (Duke University); and, MDA-231 breast tumor cell line cells were obtained from the ATCC.

d. Cellular Transfection ("Lipofection")

i. Lipofection of TILs

For transfection of TILs, $5-10\times10^6$ cells were plated in 1 ml of serum-free media per well of a 6-well dish. 50 µg of plasmic. DNA comprising IL-2 genomic material (e.g., pMP6-IL2) was mixed with 50 nmoles of DDAB (as the liposomes composed of DDAB and DOPE in a 1:1 molar ratio). Serum-free medium (0.5 ml) was added to the AAV-:liposome complex which was then added to the cells. To effect lipofection, the cells were incubated at room temperature for 5 minutes, and FBS was added to a final concentration of 5%.

The transfected TILs are returned to the patient from whom they originated. These cells provide the therapeutic benefits equal to or greater than conventional cytotoxic TILs administered in combination with IL-2. The need to systemically co-administer IL-2 to maintain cytotoxic T cell activity is reduced or eliminated which provides an advantage to the patient of avoiding adverse and potentially lethal toxicity.

ii. Lipofection of Neoplastic Cells

A culture of neoplastic cells such as breast cancer cells or ovarian tumor cells was transfected in the following manner: $10^6$ tumor cells were transfected with 5 µg plasmid DNA (e.g., pMP6-IL2) mixed with 30 nmoles total lipid, wherein the lipid comprises liposomes composed of DDAB and DOPE in a 1:1 molar ratio. One ml of AIM V media was added to the liposome-DNA complex and the mixture incubated at room temperature for 30 minutes. This mixture was then added to the cells and incubated at 37° C. for 24 hours after which the cells were lethally irradiated with 10,000 rads.

Alternatively, DNA-liposome complexes were formed by the following method: The desired amount of DNA was transferred to a sterile vial and 1 or 2 nmole DDAB per µg DNA was added with mixing. Then, 1 ml serum free medium was added to the liposome-DNA complex. Cells to be transfected were plated in six well plates. Primary tumor and tumor cell lines were plated at $10^6$ cells/well in 2 ml serum-free medium. The liposome-DNA complex was added to the cells and incubated for 5 min at room temperature. FBS was added to a final concentration of 10%.

e. Assay of Transgene Expression i. Extracellular Assays

Expression of the transgene was documented by assaying IL-2 production by the irradiated cells. IL-2 can be assayed by ELISA using methods well-known in the art.

Cell-free supernatants were collected and the IL-2 concentration determined by ELISA at various time points. For example, IL-2 assays were performed on 72 hour supernatants, in duplicate. Successful transfection of the IL-2 transgene was defined as IL-2 concentrations of >100 pg/72 h/$10^6$ cells.

ii. Intracellular Assays

Cells were harvested at various time points, washed with PBS and resuspended in cold 1% paraformaldehyde in PBS. After 10 minutes at 4° C., cells were washed with cold saponin buffer (0.1% saponin, 10% FBS in PBS) and stained with mouse anti-human IL-2 antibody for 15 minutes at 4° C. Cells were then washed with cold saponin buffer and stained with FITC-conjugated goat anti-mouse F(ab')$_2$ antibody for 15 min at 4° C. Cells were washed with saponin, then PBS, and were analyzed by flow cytometry.

f. Southern Hybridization to Detect IL-2 DNA

Chronosomal DNA was isolated by Hirt fractionation. After restriction digestions, 5μg DNA per sample was electrophoresed, transferred to Hybond N+® nylon membrane and hybridized with the 0.685 kb IL-2 fragment.

g. Cytotoxicity Assay

Target cells were labelled with 100 μCi 51Cr per $10^6$ cells. 5000 target cells were plated in triplicate in 96 well microplates. Effector cells were added to yield a 20:1 effector-:target ratio. After a 4 hr incubation, 100 μl supernatant were collected from each well and the radioactivity counted in a K-counter.

h. Proliferation Assay $5\times10^4$ cells in 100 Tl AIM V media were plated in triplicate in 96 well microplates. Each well was pulsed with 1 μCi $^3$H-thymidine. Cells were harvested 24 hours later and the radioactivity determined in a scintillation counter.

i. TCR Analysis

TILs were frozen after various times in culture and after stimulation. TCR usage was analyzed by reverse transcriptase polymerase chain reaction (RT-PCR) using methodologies known in the art.

2. RESULTS a. Ex vivo Activation of Tumor Specific CTL: Stimulation of TIL Cells During Culture TILs were stimulated in culture for 5–7 days by autologous irradiated tumor cells or by IL-2-transfected, irradiated autologous tumor cells at a ratio of TILs/Stimulators of 50:1. The responses were compared to those of TILs cultured in AIM V medium supplemented with 600 IU/ml rIL-2. The stimulated TILs were analyzed for changes in phenotype, cytotoxic activity, proliferation and TCR repertoire. This simple and rapid method of stimulating TILs during culture is utilized for both in vitro and in vivo gene transfer protocols.

As an alternate means for stimulating TILs in culture, tumor-associated antigenic peptides may be added directly to the TIL cultures.

i. Stimulation of TIL with transfected tumor cells

Neoplastic cells were transfected, for example, with pMP6-IL2 to further increase their antigenicity. Transfected cells were irradiated and, 24 hrs later, the transfected cells were washed, harvested by trypsinization, pelleted by centrifugation and resuspended in culture medium. The transfected, irradiated neoplastic cells were then cultured with TIL.

Tumor-specific reactivity was retained by the TIL during culture and expansion.

Autologous tumor cells or HLA-matched allogeneic tumor cells were used to re-stimulate selected TILs during the expansion phase of culture. This is of significant value because the specificity of T cells for their target is sometimes known to diminish during the course of expansion. Long term culture of TILs often results in polyclonal expansion, with a diminution of tumor-specificity by the expanded cell population. As shown in FIG. 13, stimulation of expanded TIL with autologous tumor cells resulted in enhanced specificity as measured by TCR usage. The specificity of TILs stimulated with IL-2-transduced tumor cells was greater than that of TIL stimulated with unmodified tumor cells (assessed by TCR repertoire). The enhanced specificity of TILs stimulated by transfected tumor cells was particularly notable after 30 days of culture.

The results demonstrated that cationic liposomes complexed to an AAV plasmid efficiently transfected primary tumor cells as well as cultured tumor cell lines. Up to 50% of the transfected cells expressed IL-2 measured as intracellular IL-2 levels, and the duration of expression was up to 30 days. Irradiation of tumor cells after transfection did not alter transgene expression. TCR analysis demonstrated expansion of tumor-specific T cells from bulk expanded TIL under the stimulatory influence of gene-modified autologous tumor cells.

b. Proliferation of TIL After Transfection with the IL-2 Gene

Results in FIG. 14 show the reactivity of breast TIL which had been isolated from pleural effusion using a AIS Micro-CELLector CD80 device and cultured for three weeks in medium containing 600 IU/ml IL-2. Analogous experiments were performed with TILs from an ovarian tumor, with consistent results.

Approximately $10^7$ TILs were transfected with various compositions comprising pMP6-IL2 DNA:liposome complexes. Two compositions of liposomes, "RPR DDAB" (Nattermann Phospholipid GmBH, Cologne, Germany) and "1100–28" (Applied Immune Sciences, Inc., Santa Clara, Calif.) were tested. The RPR DDAB liposomes had a DDAB:DOPE ratio of 1:1; the 1100–28 liposomes had a DDAB:DOPE ratio of 1:0.6. The transfected TIL cells were then cultured without exogenous IL2. Positive controls were cultured in the presence of 600IU/ml IL-2.

Five days after transfection, proliferation (or growth) of transfected cells and untransfected control cells were assessed using $^3$H-thymidine incorporation. The counts from the positive control cells were set to be 100%. Percent growth (relative to the controls) ranged from 40–80% for the RPR DDAB liposome-transfected groups, and from 40–60% for the 1100–28 liposome group. Results presented in FIG. 14 demonstrate that breast cancer TILs, when transfected with the IL-2 gene, did not require exogenous IL-2 to maintain proliferation in vitro.

C. Thy 1.2 Gene Expression in TIL (FIG. 15)

Breast cancer TILs were transfected with pMP6 containing the neomycin-resistance gene and the murine Thy1.2 gene (pMP6/neo/Thy1.2). This was an alternate embodiment of the pMP6 plasmid containing the IL-2 gene. The pMP6/neo/Thy1.2 plasmid was complexed to the same DDAB:DOPE liposomes described above (in FIG. 14). On day 2, the transfected cells were stained with anti-Thy1.2 antibodies conjugated to phycoerythrin (PE) (Pharmingen, San Diego, Calif.) and analyzed by flow cytometry. As depicted in FIG. 15, the mouse T cell surface marker Thy1.2 was expressed efficiently in transfected human $CD8^+$ TILs.

d. Transgene Expression in Irradiated Human Melanoma Cells Following Transfection Melanoma cells were successfully transfected with pMP6-IL2. For these transfections, lipid compositions in addition to DDAB:DOPE were utilized. These various lipid compositions successfully produced lipofection and subsequent cytokine expression.

Melanoma cells were isolated from metastatic foci using conventional enzymatic digestion methods known in the art. Cells were grown in DMEM supplemented with 5–10% fetal calf serum and maintained in culture for between 5 days and 8 years.

In preparation for lipofection, tumor cells were plated on 60 mm dishes at a density of $5\times10^5$ cells/dish. The next day, liposomes comprising 10–30 nmol of cationic lipid and 2–10 μg DNA were admixed and transferred in serum-free medium to the adherent monolayers. After 1–5 hours incubation, FCS was added to the medium.

Various liposome preparations were employed successfully, including: DMRIE:DOPE in a 1:1 molar ratio (Vical, San Diego Calif.); DOSPA:DOPE, 3:1 mass ratio (Gibco, Gaithersburg, Md.) and DDAB:DOPE in a 1:2 molar ratio.

The transfected cells were exposed to lethal X-irradiation (5000 rads) 24 hours following lipofection. Culture supernatants were collected at 72 hours and the IL-2 levels therein were measured by ELISA using standard methods. The results appear in Table 5, below, which shows the highest level of IL-2 expression attained with each liposome preparation. High-level expression (>5000 pg/ml) was detected in nonproliferating viable cells up to 26 days lowing irradiation.

TABLE 5

| | IL-2 Levels (picograms/ml) | | |
| --- | --- | --- | --- |
| | | LIPOSOMES | |
| Cell Line | DMRIE:DOPE | DOSPA:DOPE | DDAB:DOPE |
| DM92 | 33,275 | 12,650 | 1,238 |
| DM175 | 24,968 | 5,758 | not tested |
| DM208 | 10,650 | 9,100 | 8,900 |
| nw31s | 26,022 | 35,150 | 31,769 |
| DM336 | 24,967 | not tested | 15,775 |
| DM336 | not tested | 18,730 | 8,713 |
| DM377 | 5,504 | 3,546 | not tested |

These results demonstrate successful transfection of human melanoma cell lines by nonviral, liposome-mediated delivery of plasmid pMP6-IL2 which resulted in significant production of IL-2 (following lethal irradiation).

e. Extracellular Assays of Transgene Expression in a Prostate Tumor Cell Line

To compare the level and duration of transgene expression following transfections with different plasmid constructs, the prostate tumor cell line, R3327, was transfected with 10 μg standard plasmid (pBC12/CMV-IL2) or 10 μg AAV plasmid (pACMV-IL2) complexed to 10 nmole DDAB as DDAB:DOPE 1:2 liposomes.

Supernatants were collected at various time points and assayed for IL-2 levels by ELISA. FIG. 10 shows IL-2 levels expressed as $pg/ml/10^6$ cells in 24 hrs of culture. Transfection with AAV plasmid produced IL-2 levels significantly higher than with standard plasmid. In addition, transfection with AAV plasmid caused production of IL-2 for at least 30 days, in contrast to only 7 days with a conventional IL-2 plasmid.

Figure 17:
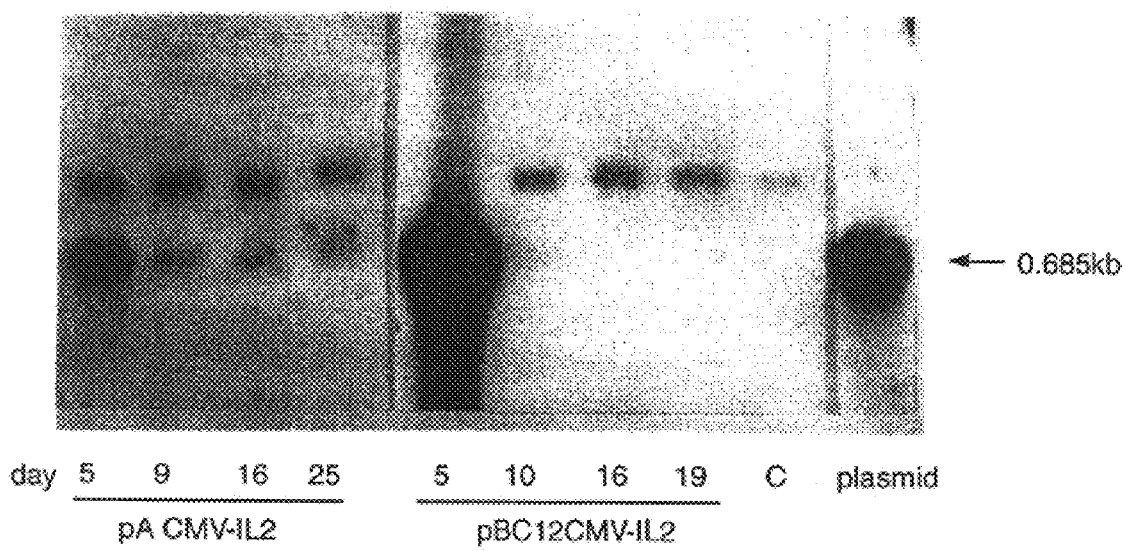
FIG. 17 shows Southern blot analysis of chromosomal DNA from R3327 cells transfected with either the AAV plasmid pACMV-IL2 or the standard plasmid pBC12/CMV-IL2. The blot was probed with the 0.685 kb BamHI/HindIII fragment of the IL-2 gene. The lane marked "C" contained DNA from untransfected cells. The IL-2 insert is shown in the last lane marked "plasmid".

FIG. 17 depicts a Southern blot analysis of chromosomal DNA from R3327 cells transfected with an AAV plasmid (pACMV-IL2) or the standard plasmid (pBC12/CMV-IL2). The blot was probed with the 0.685 kb BamHI/HindIII fragment of the IL-2 gene. Control (C) represents DNA from untransfected cells. The IL-2 insert is shown in the last lane.

f. Intracellular Assays of Transgene Expression in a Prostate Tumor Cell Line Transfected With AAV Plasmids The prostate cell line R3327 was transfected with AAV IL-2 plasmid (such as pACMV-IL2) complexed with DDAB:DOPE liposomes; the liposomes in a 1:1 or 1:2 DDAB:DOPE composition ratio. The DNA:liposome ratio was 10 μg DNA:10 nmole DDAB in both groups.

Transfected cells were assessed at various time points for intracellular IL-2 protein using immunostaining in a modified flow cytometry procedure as described herein. The results are shown in FIG. 18 (as percent positive cells expressing IL-2 protein). Untransfected cells were used as negative controls and the values of these controls were subtracted from the values of transfected groups.

g. Transgene Expression in Primary Tumor Cells

AAV plasmid-liposome complexes were employed to transfect various primary tumor cells. One lung, one ovarian, and two breast tumor samples were isolated from fresh tumor biopsies. Tumor cells were cultured in RPMI-1640 medium supplemented with 10% FBS for 2–3 weeks prior to the transfection.

The primary tumor cells were transfected with 10 μg plasmid (such as pACMV-IL2) complexed to 10 nmoles of DDAB as DDAB:DOPE 1:1. Supernatants were collected on days 2 and 3 and the IL-2 levels measured by ELISA. The results are shown in FIG. 6 (expressed as pg $IL-2/ml/10^6$ cells in 24 hours of culture.

h. Transgene Expression by Irradiated Primary Breast Tumor Cells and Prostate Tumor Line Cells To determine the effect of irradiation on IL-2 gene expression, primary breast tumor cells and cells of a prostate cell line (R3327) were transfected with a composition comprising pACMV-IL2 and DDAB:DOPE liposome complexes, and assessed for gene expression after lethal irradiation. The results for the tumor cell line are shown in FIG. 19A, and the results for the primary tumor cells is are in FIG. 19B. On day 2, an aliquot of the cells was irradiated with 6000 rads using a $^{60}$Co irradiator and then returned to culture. Supernatants were collected 24, 48, 72 and 96 hrs after irradiation and tested for IL-2 levels. As shown in FIG. 19, lethal irradiation following transfection did not inhibit transgene expression, measured as pg $IL-2/ml/10^6$ cells in 24 hr culture.

IV. DISCUSSION

In the present studies, the AAV plasmid which contained a transgene and AAV terminal repeats was used as a DNA vector, and cationic liposomes were used as carrier molecules. The results demonstrated that the AAV plasmid DNA:liposome complexes efficiently transfected primary tumor cells, cultured cell lines, primary lymphoid cells, and $CD34^+$ stem cells. In the absence of any recombinant virus (producible from rep protein and cap capsid particles in adenovirus-infected cells), high levels of integration and sustained expression of a transgene was achieved by the elegant transfection process of this invention.

In addition to high levels of expression, the combination of AAV plasmid:liposomes disclosed herein induced long-term (up to 30 days) expression of genes (FIGS. 5a–5b), in contrast to the transient expression which typically follows liposome-mediated transfection. Notably, sustained expression was demonstrated in the AAV plasmid lipofected group, as well as in the recombinant AAV transduced group (FIGS. 5a–5b). Moreover, ten-fold higher levels of expression were observed with AAV plasmid as compared to standard plasmid transfection, as shown in FIGS. 4a–4b.

Under the test conditions disclosed herein, there was no difference in efficiency between optimal AAV transduction and maximal AAV plasmid:liposome transfection. Concerning the time-course of expression, cationic liposomes had previously been shown to mediate only transient expression of standard plasmid DNA in mammalian cell types (Felgner et al., supra; Rose et al., supra). Moreover, much lower efficiency of integration into the host genome was observed in prior art liposome-mediated transfection as compared to the results disclosed herein (Shaefer-Ridder, M. et al., *Science* (1982) 212:166–168). As shown herein, cationic liposomes complexed with AAV-plasmid DNA carrying the AAV terminal repeats increased the genomic DNA integration relative to the standard plasmid that lacked only the AAV ITRs. Liposomes comprising AAV plasmid material delivered the plasmid DNA in the absence of any specific cell surface receptors, and replaced the function of virus in gene delivery.

The foregoing disclosure demonstrates that virus vectors can be altogether replaced by liposomes, and efficient expression and integration attained by utilizing the present construct, including the viral elements responsible for both the efficiency and integration. Production of virus for infection is therefore avoided, virtually eliminating the possibility of a dangerous virus recombinational event. The end results were accomplished by use of an elegant transfection process combining AAV plasmid and cationic liposomes.

In a preferred embodiment, the combination of AAV plasmid and cationic liposomes not only transfected cultured cell lines efficiently, but also transfected primary tumor cells and fresh blood-derived cells including T cells and stem cells. These observations are noteworthy because most gene therapy strategies involve gene delivery to primary T lymphocytes or tumor cells. Up until now, these strategies have relied primarily upon transgene insertion into retrovirus or DNA virus vectors. A fundamental disadvantage of the retrovirus system is the inability to transfect non-dividing primary cells. The present invention shows that cationic liposomes comprising AAV material mediates transfection of dividing and non-dividing cell types. Accordingly, AAV plasmid:cationic liposomes provide a highly efficient transfection system for sustained, high-level gene expression.

Advantageously, plasmid DNA:liposome complexes can be delivered in vivo, such as by intravenous, intraperitoneal and aerosol administration, without any measurable toxicity (Philip, R. et al., 1993, supra; Stribling, R. et al., *Proc. Natl. Acad. Sci. USA* (1992) 89:11277–11281; Zhu, N. et al., *Science* (1993) 261:209–211; Stewart, M. J. et al., *Human Gene Therapy* (1992) 3:267–275). In accordance with the invention, DNA concentration can be optimized to obtain maximum expression. Thus, gene transfer using liposomes comprising AAV material successfully transferred AAV and transgene material into a wide variety of cell types ex vivo, and can be used in vivo as well. The present invention therefore provides an immense advantage to any gene therapy protocol.

Moreover, various primary neoplastic cell types, neoplastic cell lines, and several T cell subpopulations were transfected with AAV plasmids using DNA:liposome complexes. As shown herein, cationic liposomes facilitated AAV plasmid transfections into cells. The ability to transfect primary tumor cells has great importance because such cells have generally been very difficult to transfect. In addition to the high level of gene expression effected by the present method, the use of AAV plasmid:liposomes induced long term (>30 days) expression of transgenes. Moreover, when activated and naive T cells were transfected with IL-2 plasmids, the plasmids were detected in the cells a minimum of 25 days post-transfection under nonselective conditions. These achievements constitute an important step forward from the short term expression in the prior art using conventional liposome-mediated transfection with standard plasmids.

TILs transfected with a cytokine transgene were found to proliferate without a need for exogenous cytokine or growth factors. This capability is very advantageous because TILs prepared in accordance with this invention can be provided to patients without the need for simultaneous systemic infusions of IL-2.

IL-2 gene expression in transfected T cells prepared according to this invention altered the dependence of those T cells on exogenous IL-2 and the effects of IL-2 withdrawal. Notably, IL-2-transfected effector T cells produced sufficient endogenous IL-2 to maintain their growth and proliferation and to prevent apoptosis that normally occurs when exogenous IL-2 is withdrawn. The dependence on exogenous IL-2 was eliminated.

Primary breast, lung and ovarian tumor cells were transfectable using AAV plasmid DNA:liposome complexes of this invention. Transfected primary and cultured tumor cells expressed the transgene product even after lethal irradiation.

According to the present invention, tumor cells (both autologous and HLA-matched allogeneic) can be used to re-stimulate selected TILs during the expansion phase. Transfected tumor cells are used as potent immunogens in tumor vaccination protocols. For treatment, the transfected neoplastic cells are typically provided together with a pharmaceutical excipient, as is known in the art. Transfected neoplastic cells are also used to stimulate corresponding TIL cells during culture. Analysis of cell phenotype, cytotoxic activity and TCR usage demonstrated that TILs which initially show tumor specificity upon isolation, but which generally lose this specificity when cultured in rIL-2, maintained and increased their tumor specificity when cultured in the presence of tumor cells, most preferably tumor cells transfected according to the present invention.

EXAMPLES OF USE OF TRANSFECTED OR ANTIGEN-LOADED DENDRITIC CELLS TO INDUCE ANTI-TUMOR AND ANTI-VIRAL IMMUNITY

Using the methods and compositions of the present invention, the inventors have employed peptide-loaded or AAV/liposome transfected DC to induce (1) primary CTL responses to tumor antigens and to viral antigens in lymphocytes from healthy donors and (2) secondary responses in lymphocytes of cancer patients or virus-infected subjects to either tumor or viral antigens. Based on these findings, it is feasible to generate tumor antigen-specific and viral antigen-specific CTL for adoptive immunotherapy in the patients having the corresponding tumor or virus infection.

TAA-specific as well as EBV-specific CTL were generated using peptide-loaded or antigen-expressing gene-modified DC from the peripheral blood of cancer patients or from EBV$^+$ normal individuals. PBMC-derived DC were either (a) pulsed with MART-1 (a melanoma-specific antigen), CEA, or EBV peptide, which antigens are presented in the context of the HLA-A2 major histocompatibility glycoprotein; or (b) transfected with MART-1, CEA, or EBNA constructs to express these proteins.

DC can similarly be pulsed ("loaded") or transfected with any other TAA, for example, proteins or peptide epitopes of MUC1 (or the MUC1 peptide PDTRPAPGSTAPPAHGVTSA, SEQ ID NO:3), K-ras, HER2 (supra), p53, Mage1, Mage3, gp100, tyrosinase, Mart 1 (Melan A), CEA, PSA, PSMA, Rage, Bage and Gage and other tumor-associated antigens including, for example, the antigens identified in Storkus, W. and Lotze, M., *Biologic Therapy of Cancer: Principles and Practice*, Second Edition, Section 3.2, "Tumor Antigens Recognized by Immune Cells," pp. 64–77, J.B. Lippincott Co. publishers (1995). A list of tumor-associated antigens which may be used in the practice of the present invention is presented below in Table 6.

the adherent PBMC were cultured in RPMI-10% FCS with granulocyte/macrophage colony stimulating factor (GM-CSF; 800 U/ml) and interleukin-4 (IL-4; 500 U/ml) for 5–7 days. Cells were harvested and dendritic cells were further purified by removing T cells using AIS CD5/8 MicroCEL-Lectors®. Dendritic cells were 60–90% pure as determined by flow cytometric analysis.

Figure 20:
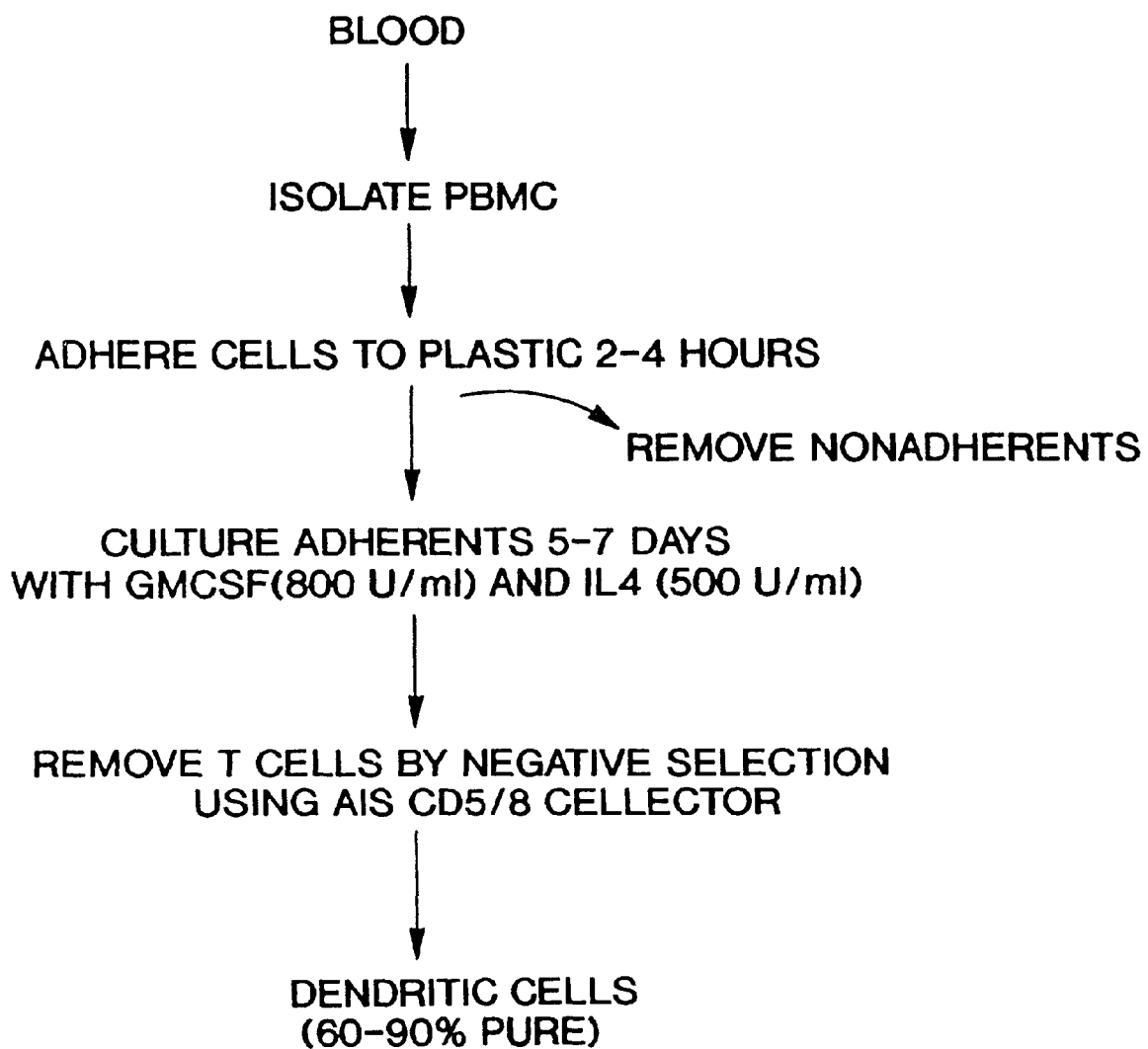
FIG. 20 shows a schematic diagram describing isolation of the dendritic cells.

As shown in FIG. 20, DC have been isolated to 60–90% purity. The cells have characteristic DC markers and are more potent than PBMC in inducing responses in mixed leucocyte culture (MLC) and to tetanus toxoid (shown in Table 7, below).

TABLE 7

Characteristics of Isolated Dendritic Cells

| Cell Surface Marker | Level of Expression |
|---|---|
| CD3, 14, 15, 16, 19, 20 | -- |
| HLA-A, B, C | ++ |

TABLE 6

Tumor-Associated Antigens and Peptide Epitopes

| Source | TAA | Amino Acid Sequence |
|---|---|---|
| Adenovirus | E1A | p234–243; SGPSNTPPEI (SEQ ID NO: 4) |
| HPV-16 | E6/E7 | mutiple putative |
|  | E7 | p49–57; RAHYNIVTF (SEQ ID NO: 5) |
|  | E7 | p20–29; TDLYCYEQLN (SEQ ID NO: 6) |
|  | E7 | p45–54; AEPDRAHYNI (SEQ ID NO: 7) |
|  | E7 | p60–79; KCDSTLRLCVQSTHVIRTL (SEQ ID NO: 8) |
|  | E7 | p85–94; GTLGIVCPIC (SEQ ID NO: 9) |
| EBV | EBNA-2 | p67–76; DTPLIPLTIF (SEQ ID NO: 10) |
|  | EBNA-2 | p276–290; PRSPTVFYNIPPMPL (SEQ ID NO: 11) |
|  | EBNA-3A | p330–338; FLRGRAYGL (SEQ ID NO: 12) |
|  | EBNA-3C | p332–346; RGIKEHVIQNAFRKA (SEQ ID NO: 13) |
|  | EBNA-3C | p290–299; EENLLDFVRF (SEQ ID NO: 14) |
|  | EBNA-4/6 | p416–424; IVTDFSVIK (SEQ ID NO: 15) |
| p53 | p53 | p264–272; LLGRNSPEV (SEQ ID NO: 16) |
| p21$^{ras}$ | ras | p5–17; KLVVVGARGVGKS (SEQ ID NO: 17) |
|  | ras | p5–16; KLVVVGAVGVGK (SEQ ID NO: 18) |
|  | ras | p54–69; DILDTAGLEEYSAMRD (SEQ ID NO: 19) |
|  | ras | p60–67; GLEEYSAM (SEQ ID NO: 20) |
| HER2/neu | neu | p971–980; ELVSEFSRMA (SEQ ID NO: 21) |
|  | neu | p42–56; HLDMLRHLYQGCQVV (SEQ ID NO: 22) |
|  | neu | p783–797; SRLLGICLTSTVQLV (SEQ ID NO: 23) |
| Human | MAGE1 | p161–169; EADPTGHSY (SEQ ID NO: 24) |
| Melanoma | gp100 | p457–466; LLDGTATLRL (SEQ ID NO: 25) |
|  | gp100 | p280–288; YLEPGPVTA (SEQ ID NO: 26) |
|  | Tyrosinase | p1–9; MLLAVLYCL (SEQ ID NO: 27) |
|  | Tyrosinase | p368–376; YMNGTMSQV (SEQ ID NO: 28) |
|  | Tyrosinase | p368–376; YMNGTMSEV (SEQ ID NO: 29) |
|  | MART-1/Aa | p27–47; AAGIGILTVILGVLLLIGCWY (SEQ ID NO: 30) |

Such antigen-loaded or transfected DC were then employed in vitro to stimulate CD8+ cells as described below. These DC are useful for treating subjects having primary tumors, recurring tumors or metastases in vivo, the cells of which express the relevant TAA either by direct administration or by administration of T lymphocytes stimulated and activated ex vivo by such DC.

Isolation and Characterization of DC

Isolation of DC is performed, with some modifications, as described by Romani, N. et,al., *J. Exp. Med.* (1994) 180:83–93. Peripheral blood mononuclear cells (PBMC) were isolated from healthy donor buffy coats by Lymphoprep gradient separation. PBMC were plated into 6 well plates at 15×10$^6$ cells per well and allowed to adhere to the plastic for 2–4 hours at 37° C. Nonadherent cells were removed and TABLE 7-continued Characteristics of Isolated Dendritic Cells

| Cell Surface Marker | Level of Expression |
|---|---|
| HLA-DR | ++ |
| CD4 | + |
| CD8 | -- |
| CD1a | +++ |
| CD11c | +++ |
| CD33 | ++ |
| CD40 | +++ |
| CD45RO | + |
| CD54 (ICAM) | ++ |

TABLE 7-continued

Characteristics of Isolated Dendritic Cells

| Cell Surface Marker | Level of Expression |
| --- | --- |
| CD58 (LFA3) | ++ |
| CD80 (B7) | + |
| Property | |
| Concentration of Antigen for Tetanus Toxoid Response | $<10^{-11}M^a$ |
| Number of cells for 50% MLC Response | $<1000^b$ |

[a]Compared to $>10^{-9}M$ for peripheral blood mononuclear cells
[b]Compared to 80,000 for peripheral blood mononuclear cells DCs are also generated in vitro by culturing human CD34+ progenitor or stem cells from peripheral blood, bone marrow or cord blood in the presence of GM-CSF and tumor necrosis factor-I, with the optional presence of IL-3 (Caux, C. et al., *Nature* 360:258–261 (1992); Reid, C. D. et al., *J. Immunol.* 149:2681–2688 (1992); Santiago-Schwarz, F. et al., *J. Leukocyte Biol.* 52:274 (1992), which references are incorporated by reference in their entirety). Such in vitro-generated DC have the capacity to capture and process native antigens and can prime naive T cells (Caux, C. et al., *J. Immunol.* 155:5427–5435 (1995). DCs generated in this way are used to express tumor antigens, viral antigens, etc., as has been described herein for DC isolated as such from peripheral blood.

Transfection of DC

Plasmids were purified by alkaline lysis and ammonium acetate precipitation. Nucleic acid concentration was measured by UV absorption at 260 nM.

Liposomes were prepared by combining the cationic lipid dimethyldioctadecylammonium bromide (DDAB) with the neutral lipid dioleoylphosphatidylethanolamine (DOPE) alone or with both DOPE and cholesterol in the desired molar ratios as described above. After evaporating the lipids to dryness in a rotary evaporator, they were resuspended in sterile deionized water to yield a concentration of 1 ml DDAB. The solution was then sonicated to clarity in an ultrasonic bath. Liposomes were stored under argon gas at 4° C.

To form the DNA-liposome complexes, the desired amount of DNA was transferred to a sterile vial and the desired amount of DDAB was added and mixed. 1 ml serum free medium was added to the liposome-DNA complex. Cells to be transfected were plated in 2 ml serum free medium in 100 mm dishes. The liposome-DNA complex was added to the cells and allowed to incubate for 10 minutes at room temperature. Medium containing serum, IL-4 and GM-CSF was added to reach the desired final volume.

To measure expression of CAT, cells were harvested 3 days post-transfection, and cell extracts were prepared and normalized according to protein content. Extracts were mixed with 200 nmoles acetyl coenzyme A and 0.3 TCi $^{14}$C-chloramphenicol and incubated for 16 hours at 37° C. Acetylated and nonacetylated chloramphenicol species were extracted with cold ethyl acetate and resolved on silica TLC plates with 95:5 (vol/vol) chloroform/methanol solvent. The radiolabelled products were visualized by autoradiography.

For determination of intracellular IL-2, cells were treated with monensin 18 hours before immunostaining. After washing, cells were permeabilized with ethanol, blocked to prevent nonspecific binding using IgG and immunostained with mouse anti-human IL-2 antibody followed by FITC-conjugated goat anti-mouse antibody. Cells were then analyzed by flow cytometry.

In the case of NGFR, three days after transfection with the NGFR gene, cells were analyzed for expression of NGFR by staining with an antibody specific for NGFR followed by flow cytometry.

In addition to providing an antigen for antigen presentation by lipofection, the antigen can be provided by "pulsing" DC with the desired protein or peptide. For example, DC have been isolated from the peripheral blood of an HLA-A2+ melanoma patient, stripped of endogenous peptide associated with HLA-A2, and pulsed with an HLA-A2 restricted peptide, MART-1, a melanoma-associated antigen. (See, for example, Restifo, NP et al., *Cancer Res* (1995) 55:3149–3157).

Figure 21:
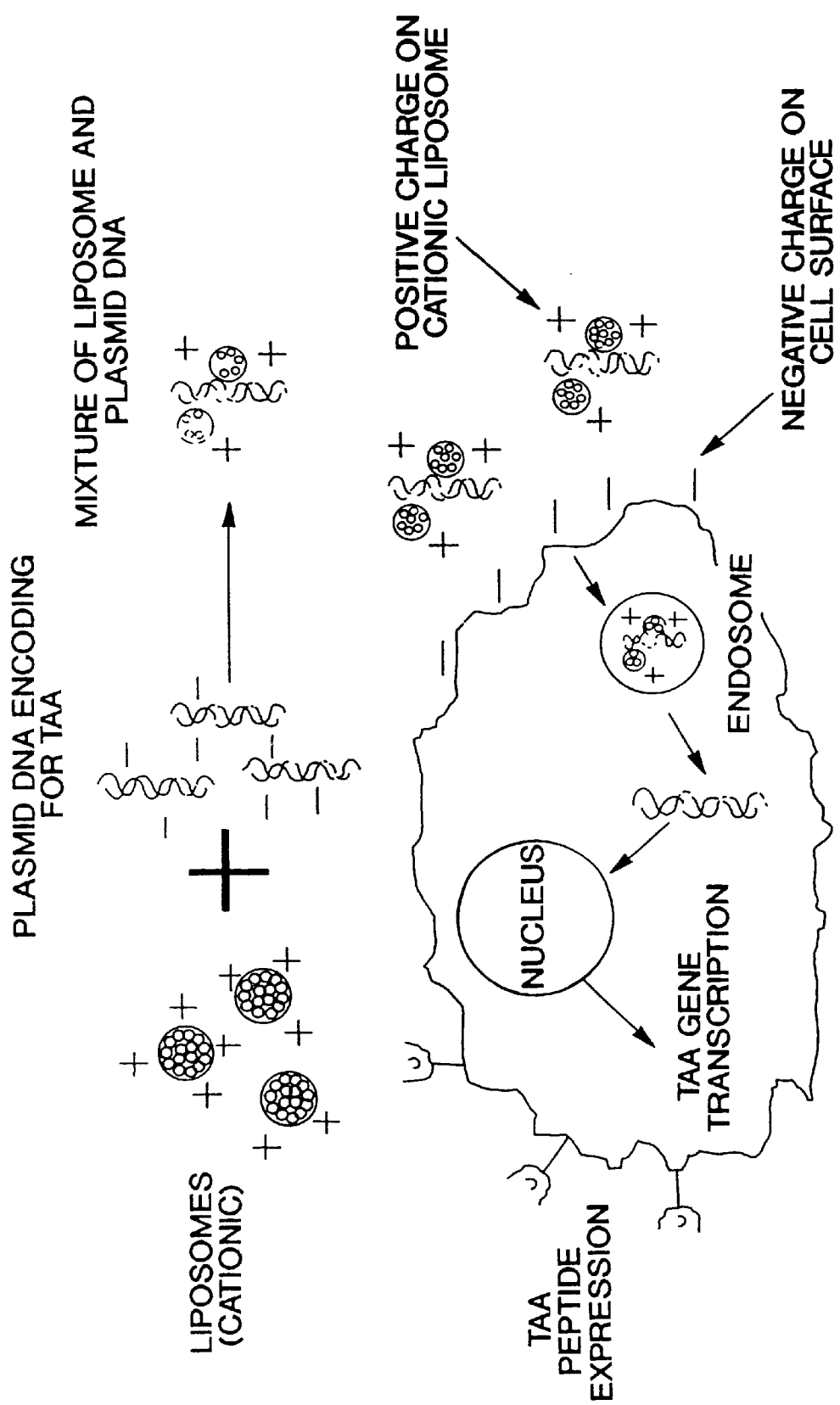
FIG. 21 is a schematic diagram showing the transfection of dendritic cells with a mixture of liposomes and plasmid DNA.

The isolated dendritic cells have been transfected using the AAV plasmid:liposome gene delivery system described herein and in PCT publication WO 95/07995 (Mar. 23, 1995). FIG. 21 provides an outline of this method. Cationic liposomes complexed to AAV plasmid DNA result in successful transfection of either dividing or nondividing cell types.

Figure 23:
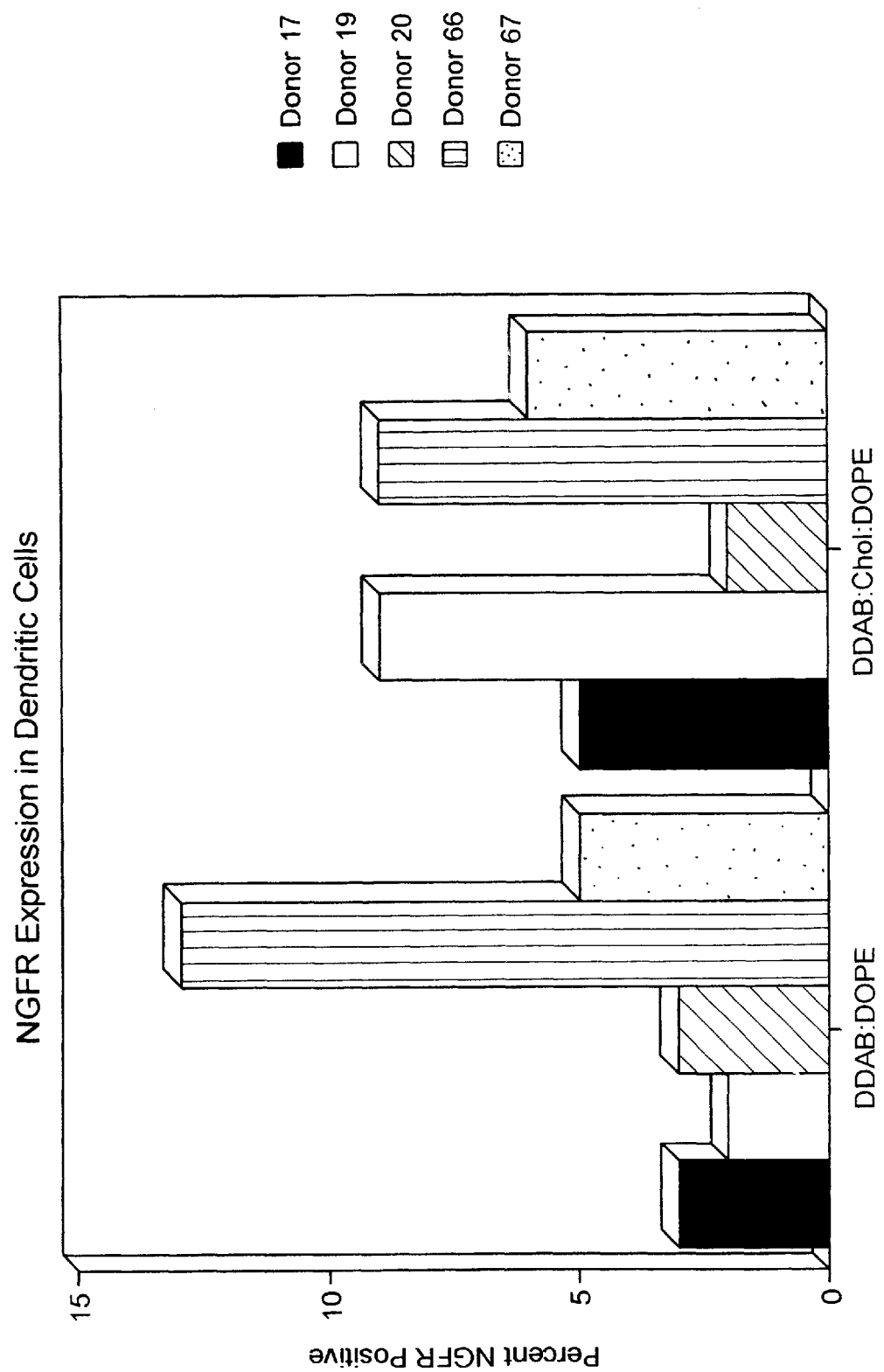
FIG. 23 is a graph showing the expression of nerve growth factor receptor (NGFR) by dendritic cells lipofected with an AAV plasmid containing the NGFR gene.
Figure 24:
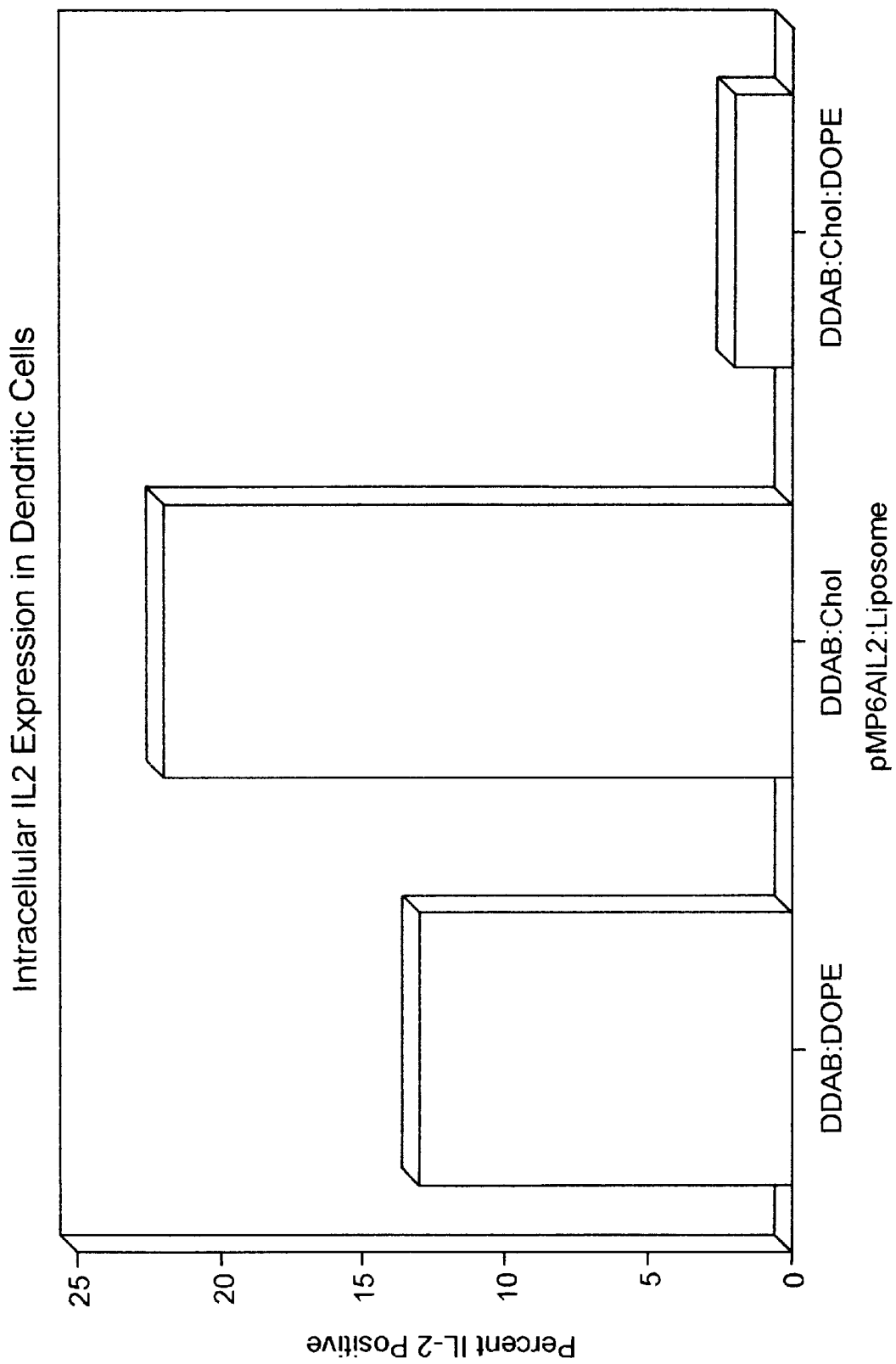
FIG. 24 shows production of IL-2 with dendritic cells lipofected as in FIG. 23.

Using the vector system described herein, the genes encoding the CAT reporter gene as well as genes encoding NGFR and IL-2 were transfected or "lipofected" into the isolated dendritic cells. Production of the proteins encoded by the transfecting DNA was observed (FIGS. 22–24).

Figure 22A:
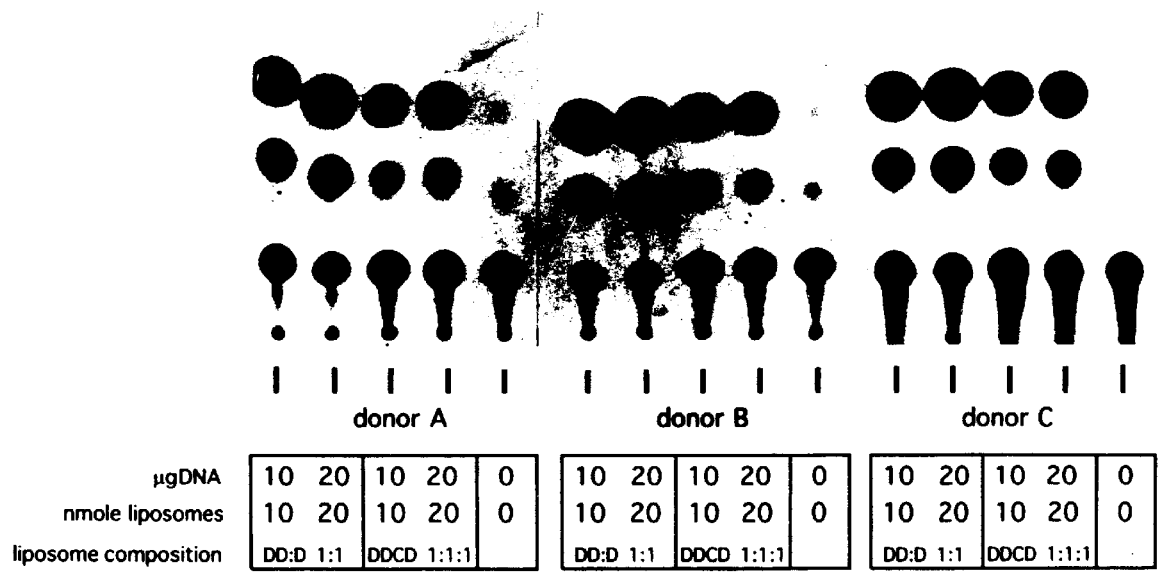
FIG. 22 shows the results of the analysis of dendritic cells lipofected with an AAV plasmid containing the chloramphenicol acetyl transferase (CAT) reporter gene.
Figure 22B:
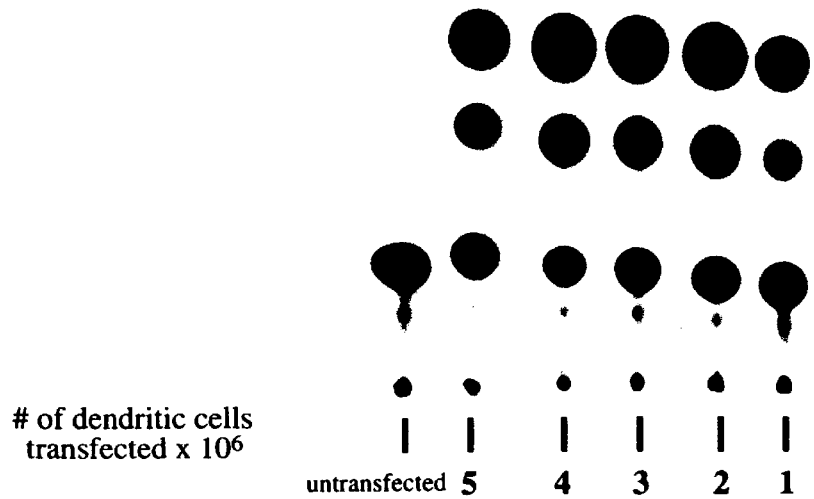

With reference to FIG. 22, DC were lipofected with AAV plasmid containing the CAT gene complexed to DDAB:DOPE liposomes (lanes 1,2) or DDAB:CHOL:DOPE liposomes (lanes 3,4). Three days following transfection, CAT expression was analyzed as described. All three donors (A, B and C) showed unreacted chloramphenicol, as well as expression of both the monoacetylated position 1 and the monoacetylated position 3 forms of chloramphenicol. The mock-transfected DC (lane 5) showed only unreacted chloramphenicol. CAT expression was detected in as few as $1 \times 10^6$ dendritic cells.

In addition to the genes described above, the dendritic cells are preferably pulsed with genes encoding a tumor-associated peptide such as EBV-associated peptides. For example, DC cells are pulsed with HLA-A2- or HLA-B8-restricted EBV peptides or with peptides derived from the oncogene HER2, carcinoembryonic antigens (CEA) (see below), MUC1 supra, K-ras and the like. Alternatively, DNA constructs containing the genes encoding these tumor-associated peptides are lipofected, as described herein, into DC. Expression efficiencies of 10–30% have been achieved.

Figure 32:
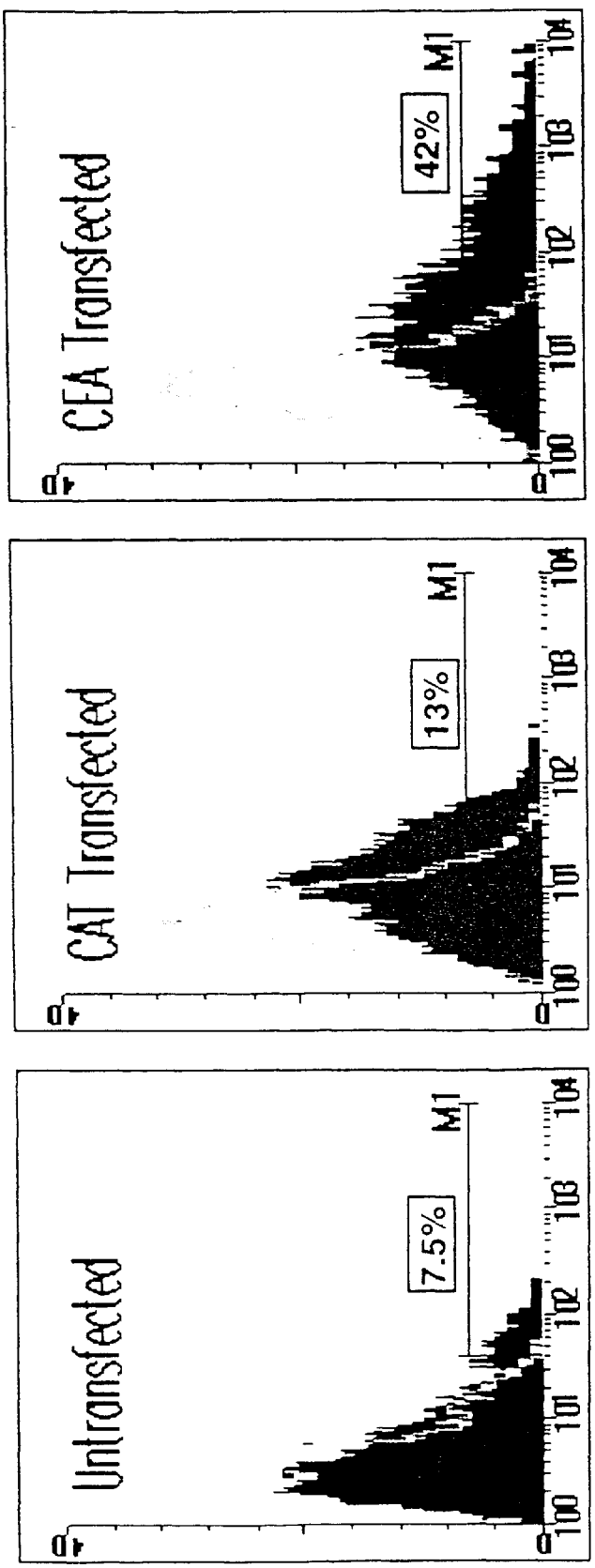
FIG. 32 shows the results of a flow cytometric analysis of the expression of the CEA gene transfected into of MCF7 cells using an anti-CEA antibody. The left panel shows untransfected cells. The middle panel shows CAT transfected cells. The right panel shows CEA-transfected cells.

As an example of the foregoing, the MCF7 cell line was transfected with the AAV plasmid containing the CAT gene complexed to DDAB:DOPE liposomes ("mock" transfected) or transfected with the AAV plasmid containing the CEA gene complexed to DDAB:DOPE liposomes. Three days following transfection CEA expression was analyzed by flow cytometric analysis of the cells stained with an antibody specific for CEA. The results are shown in FIG. 32. CEA transfected cells show approximately 30% CEA expression compared with mock transfected cells (42% positive vs. 13% positive).

Stimulation of CTL Activity by DC or Other Antigen Presenting Cells

The antigen presenting DC, prepared either by pulsing with peptide or by lipofection with the relevant gene are then used to elicit an immune response in the subject.

In one approach, CTL are isolated from the subject, for example, by harvesting CD8+ cells using methods well-known in the art. The CD8+ cells are then cultured with the antigen-presenting DC. Antigen-specific CD8+ cells, stimulated by the DC, are expanded in culture to obtain numbers of cells which are capable of adoptively transferring immune reactivity to the subject, and are administered to the subject.

In another embodiment, the antigen-presenting DC are administered directly to the subject wherein they induce the subject's immune system to generate CTL specific for the tumor-antigens expressed on the DC. The CTL are then able to attack tumor cells bearing the relevant antigen in vivo.

Tumor cells themselves are used as APC in a similar manner employing the AAV-based vector/liposome system described herein. The AAV-based expression plasmid is derived from AAV by replacing the viral rep and capsid genes with a heterologous gene. This differs from the non-AAV expression plasmid by the presence of two viral inverted terminal repeats (ITR) at either side of the promoter-gene construct. When compared to cells transfected with an identical plasmid lacking the ITRS, expression is elevated several fold. Efficient expression has been obtained in freshly isolated (uncultured) tumor cells from breast cancer, lung melanoma and ovarian tumors. For example, expression of IL-2 in such cells persisted for up to 35 days. Such IL-2 expressing cells were been used to stimulate a cytotoxic anti-tumor response in animal models for breast and ovarian cancer. When CD8+ cells were modified to contain this expression system (for IL-2 result), they were resistant to apoptotic death.

Transformed DC have been used to generate antigen-specific human CTL. PBMC from a human subject infected with Epstein Barr virus were separated from buffy coat (EBV+) cells. The dendritic cells in this population were grown by collecting the plastic-adherent cells and incubating them in GM-CSF and IL-4 for 5 days. Nonadherent PBMC were frozen for later use. The resulting dendritic cells were harvested and transfected with two vectors derived from pMP6Neo, one containing the EBV-induced nuclear antigenic peptide EBNA 3b and the other containing EBNA 3c. The transfected DC were incubated in complete medium (RPMI+10% FBS) containing GM-CSF and IL-4 for 3 days; nontransfected DC were used as controls.

To test their ability to induce cytotoxic activity, the DC were harvested, irradiated, and co-cultured with autologous nonadherent PBMC (which had been frozen during the days required to generate the DC and which were thawed immediately before culture. The nonadherent cells serve as the source of cytotoxic effector cells. The co-culture cells was incubated in AIM V medium (GIBCO/BRL) supplemented with IL-7 (10 ng/ml) for 5 days before testing.

Figure 25:
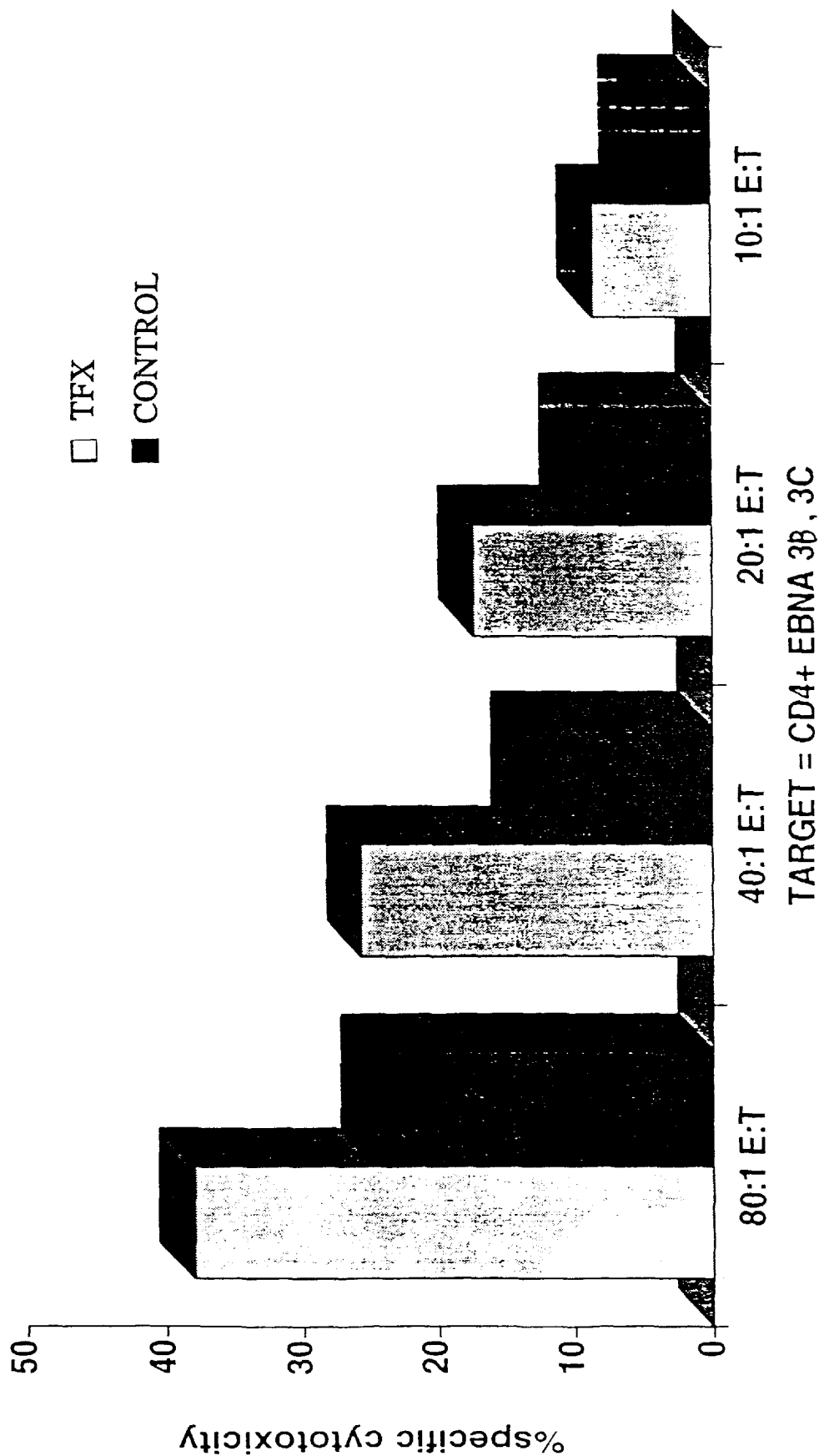
FIG. 25 shows stimulation of T cell-mediated cytotoxicity by dendritic cells transfected with pMP6Neo vectors containing EBNA 3b and 3c.

CTL activity was assessed using a $^{51}$Cr release assay. The assay was conducted using autologous CD4+ cells infected with either a vaccinia viral vector containing EBNA 3a, 3b, and 3c, or with a control vaccinia vector. The assay used an effector:target ratio of 80:1. The results are shown in FIG. 25.

DC transfected with pMP6NeoEBNA clearly stimulated specific cytotoxic effector cells. The stimulated effector cells showed about 40% specific cytotoxicity, while control effector cells (which had been co-cultured with control DC cells) had a background level of cytotoxicity (about 25%). Although the % cytotoxicity in such assays typically decreases with decreasing effector:target ratios, the cytotoxicity ratio, the present results levels of cytotoxicity (stimulated by transfected versus nontransfected DC) remained relatively constant.

GENERATION OF CEA-SPECIFIC CTL

Two strategies are used to generate CEA-specific CTL:
1) a peptide-based approach in which DC are pulsed with a CEA peptide (YLSGANLNL; Tsang, K. Y. et al., *J. Natl. Canc. Inst.* 87:982–989 (1995)) that is recognized by CTL in the context of Class I HLA-A2 molecules; and
2) a gene-based approach in which DC are transfected with a CEA-encoding plasmid containing the ITRs of AAV complexed to cationic liposomes. These systems and their utility in generating CEA-specific CTL is described below.

DC Isolation

DC were isolated using a modification of Romani et al. (supra). Briefly, 1.5×10$^8$ PBMC from an HLA-A2+ donor were allowed to adhere to a T150 flask for 2 hours at 37° C. in RPMI-10% FCS. After incubation, the nonadherent cells were removed, and the adherent cells were cultured in 30 ml of RPMI-10% FCS medium containing 800 units/ml GM-CSF and 500 units/ml IL-4. After 6–7 days of culture the differentiated DC were harvested, stripped of endogenous peptides, loaded with CEA peptide (YLSGANLNL) and used to stimulate CD8+ T cells.

Peptide Stripping and Loading

For peptide stripping, DC were washed once in a cold solution of 0.9% NaCl, 1% BSA solution, resuspended at 10$^7$ cells/ml in stripping buffer (0.13M L-ascorbic acid, 0.06M sodium phosphate monobasic, pH 3, 1% BSA, 3Tg/ml B2M, 10 µg/ml peptide) and incubated for 2 min on ice. The cells were then neutralized with 5 volumes of neutralizing buffer (0.15M sodium phosphate monobasic, pH 7.5, 1% BSA, 3 µg/ml B2M, 10 µg/ml peptide) and spun at 1500 rpm for 5 min. Finally, the cells were resuspended in peptide solution (PBS-CMF, 1% BSA, µg/ml DNAase, and 40 µg/ml peptide) and incubated for 4 hr at room temperature. The cells were irradiated (3000 rad) and washed prior to being used for stimulation.

Generation of CTL

PBMC were separated from peripheral blood leukophoresis of HLA-A2+ patients or buffy coats from healthy donors by Ficoll-Hypaque density gradient centrifugation. Responder lymphocyte precursors of peptide-specific CTL were prepared by capturing CD8+ cells on AIS MicroCEL-Lector® flasks. Captured CD8+ cells were stimulated with irradiated DC loaded with CEA peptides at a stimulator:responder (S:R) ratio of 1:3. These co-culture cells were incubated in RPMI-10% FCS containing 10 ng/ml IL-7. At days 10–12, the lymphocytes were restimulated with DC pulsed with CEA peptide (1:5 S:R ratio). Responder cells were restimulated weekly for a total of 3–4 stimulations at S:R ratios ranging between 1:5 and 1:15. As a control, CD8+ captured cells were cultured with either (a) DC pulsed with an irrelevant peptide, (b) unpulsed DC or (c) IL-7 only.

Evaluation of Cytotoxicity

HLA-A2-restricted recognition of CEA by the CTL generated as above was assessed using a standard 4hr $^{51}$Cr release cytotoxicity assay. Recognition of CEA peptide by CTL was assessed using T2 cells (a cell line defective in antigen processing which expresses "empty" HLA-A2 molecules until stabilized by the addition of peptide) preincubated for 2–4 hr with peptide at 40 µg/ml. In addition CEA specific cytotoxicity was evaluated using as targets the CEA-expressing cell lines SW403 (HLA-A2$^+$) and SW1417 (HLA-A2$^-$). Target cells were labeled overnight with 100 µCi $^{51}$Cr, washed and mixed with effector cells at varying effector:target (E:T) ratios in U-bottom microtiter plates. After a 4 hr incubation, supernatants were harvested, and the amount of $^{51}$Cr released was measured in a scintillation counter. % specific cytotoxicity was calculated as follows:

$$\frac{(\text{cpm of test sample} - \text{cpm of spontaneous } ^{51}\text{Cr release})}{(\text{cpm of maximal } ^{51}\text{Cr release} - \text{cpm of spontaneous } ^{51}\text{Cr release})} \times 100$$

RESULTS

Figure 26:
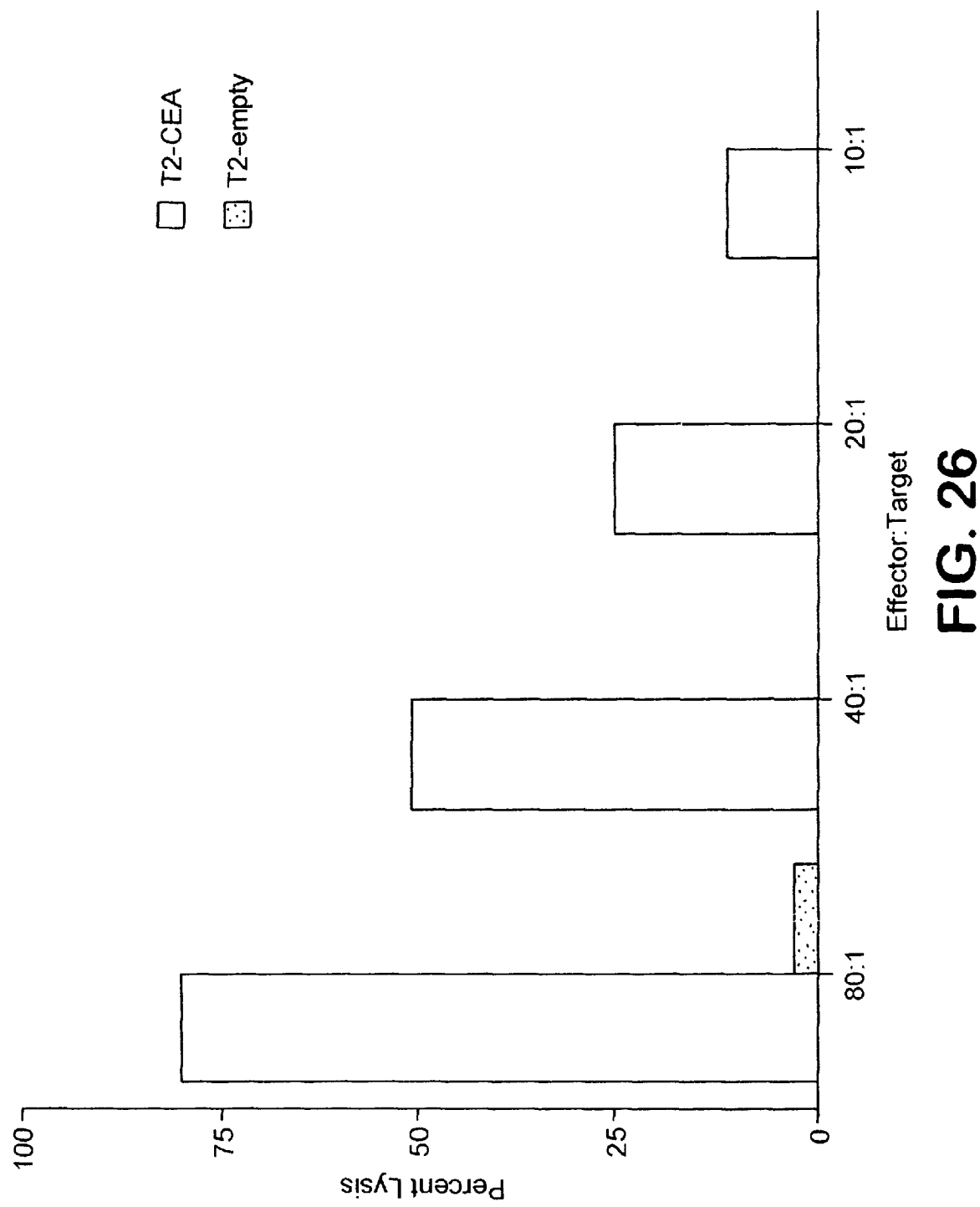
FIG. 26 shows the CEA-specific cytotoxic activity of $CD8^+$ T cells from a healthy $HLA-A2^+$ donor which were stimulates by CEA peptide-pulsed DC. Effector:target ratios are 80:1, 40:1, 20:1, 10:1.

CEA specific cytotoxicity by normal human T cells on T2 target cells pulsed with CEA peptide and "empty" T2 cells is shown in FIG. 26. Here, autologous, normal CD8$^+$ captured responder cells had been stimulated with CEA-pulsed DC and cultured in 10 ng/ml IL-7. Cytotoxicity was assayed after 3 rounds of restimulation with CEA peptide pulsed DC.

Figure 27:
FIG. 27 shows the phenotype of the cells used in FIG. 26. Cells stimulated with CEA-pulsed DC ("CEA") or with cytokines alone ("Cytokines") were stained with antibodies to CD3, CD4, CD8, and CD56.

The phenotype of the above effector cells on the day of CTL assay is shown in FIG. 27. The DC-CEA-stimulated and cytokine-stimulated T cells were stained with antibodies to CD3, CD4, CD8, and CD56. The large majority of cells in this effector cell population were CD3$^+$8$^+$.

Figure 28:
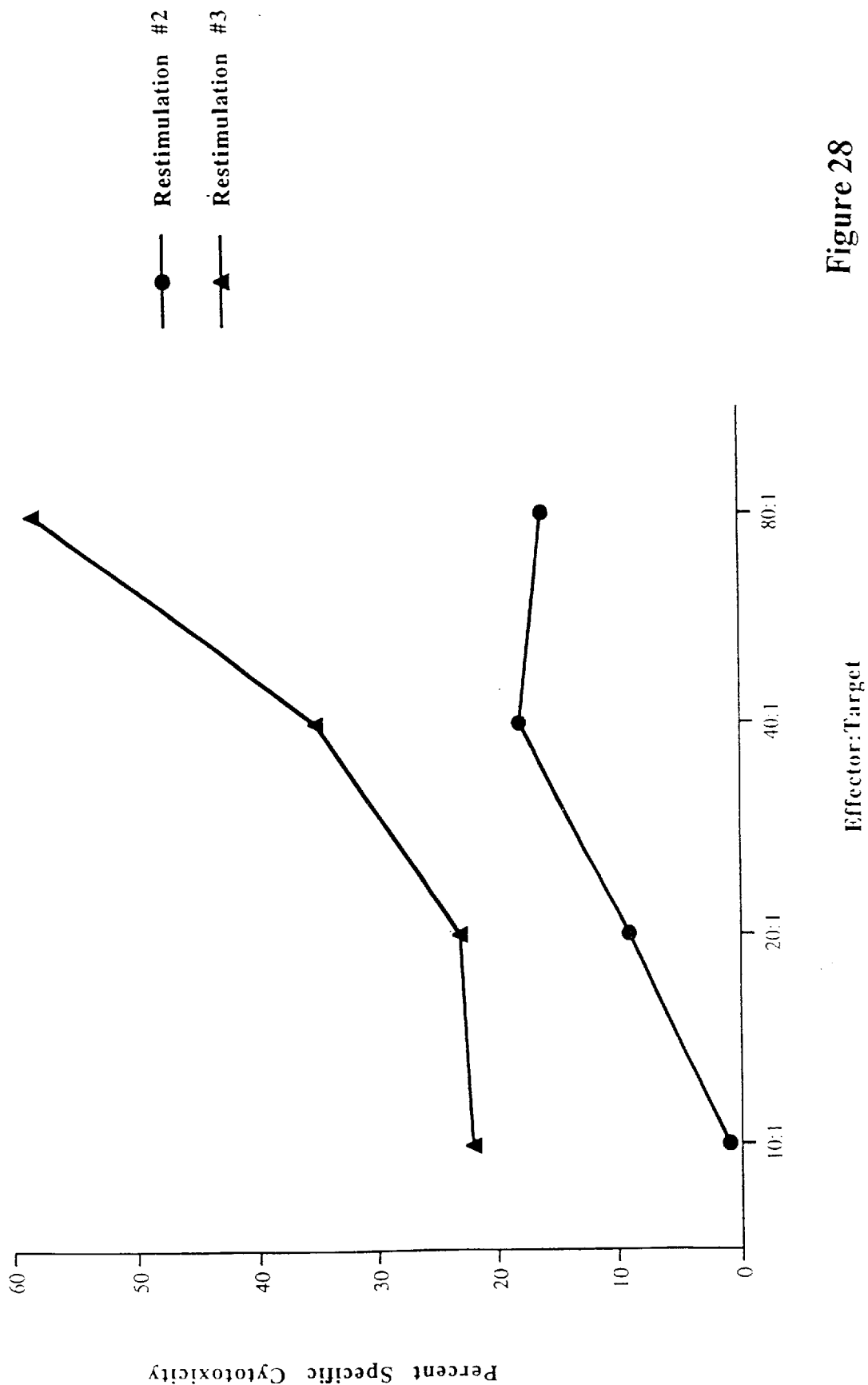
FIG. 28 shows the CEA-specific cytotoxic activity of CD8$^+$ T cells from a pancreatic cancer patient which were stimulated by CEA peptide-pulsed DC. Effector:target ratios are 80:1, 40:1, 20:1, 10:1. The background cytotoxicity on empty T2 cells has been subtracted.

The generation of CEA specific cytotoxicity by T cells from a pancreatic cancer patient on T2 target cells pulsed with CEA peptide is shown in FIG. 28. Autologous CD8$^+$ captured responder cells were stimulated with CEA-pulsed DC and cultured in 10 ng/ml IL-7. Cytotoxicity was assayed after 2 or 3 rounds of restimulation with CEA peptide pulsed DC at effector:target ratios of 80:1, 40:1, 20:1, 10:1.

Figure 29:
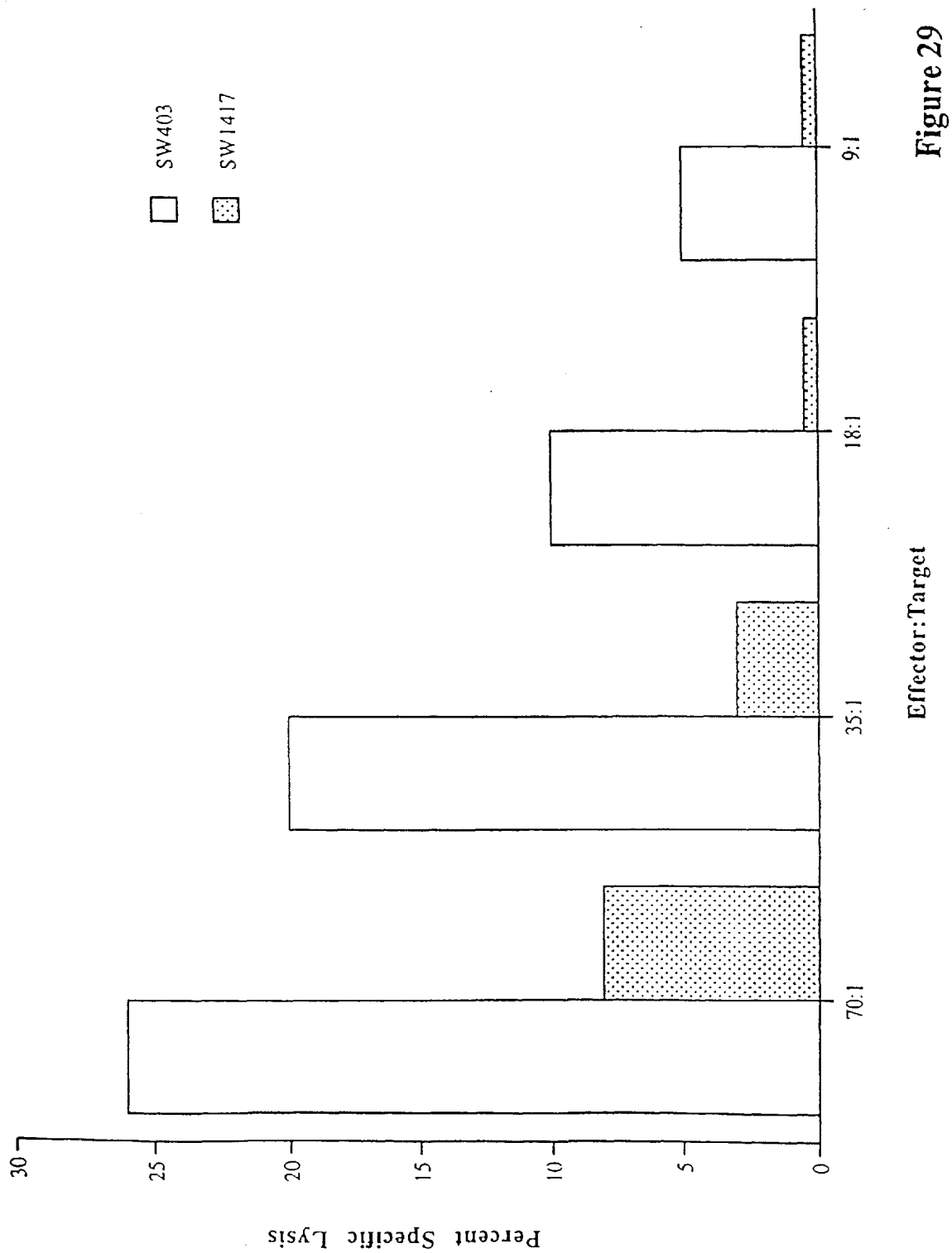
FIG. 29 shows the CEA-specific cytotoxic activity of CD8$^+$ T cells from an HLA-A2$^+$ breast cancer patient which were stimulated by CEA peptide-pulsed DC. Cytotoxic activity is tested on two target cells. SW403 is an HLA-A2$^+$CEA$^+$ cell line. SW1417 is an HLA-A2$^-$CEA$^+$ cell line. Effector:target ratios: 70:1, 35:1, 18:1, 9:1.
Figure 30:
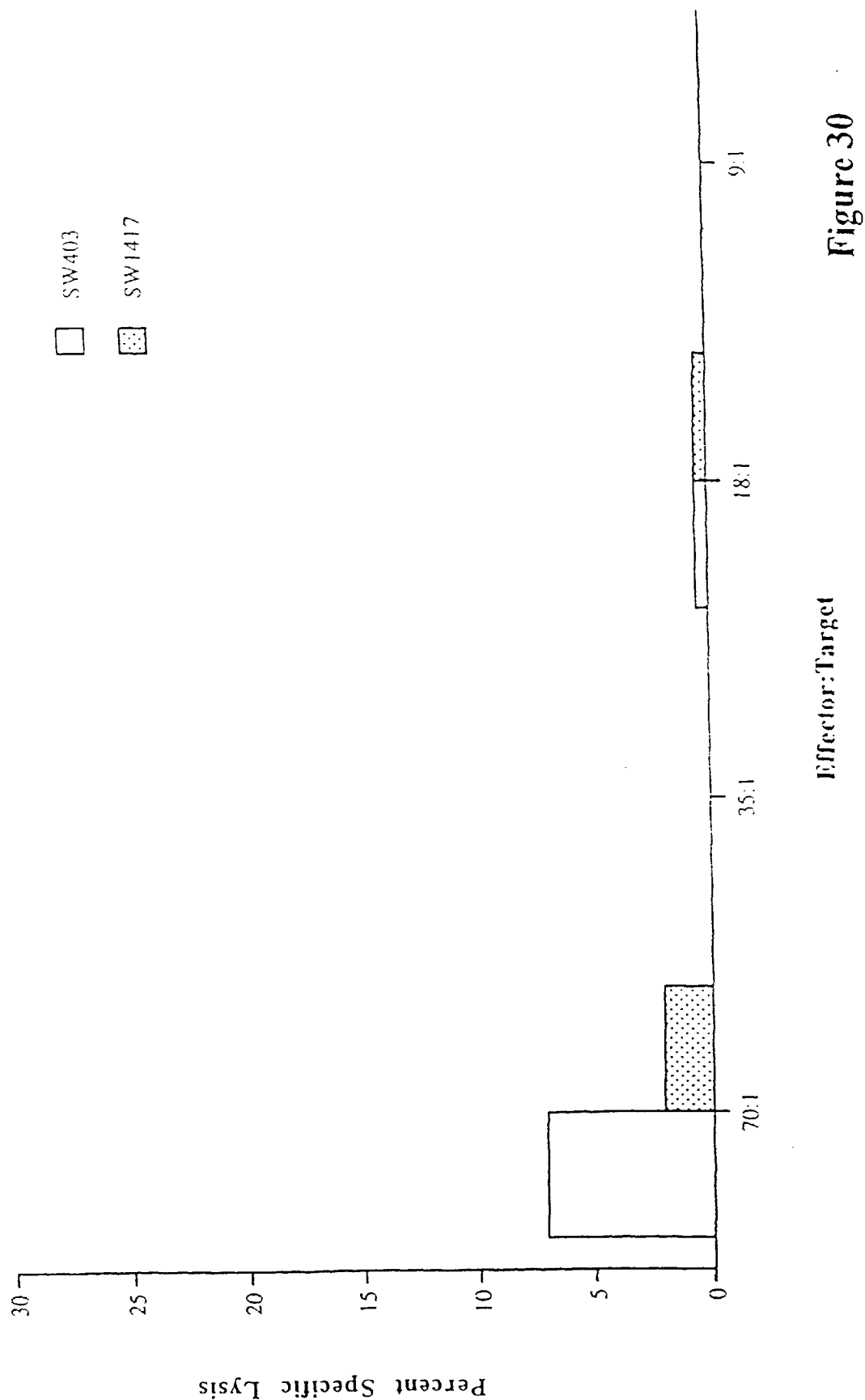
FIG. 30 shows the background cytotoxic activity of CD8$^+$ T cells from an HLA-A2$^+$ breast cancer patient which were cultured with 10 ng/ml interleukin-7 (IL-7) without DC. Target cells and effector:target ratios are the same as in FIG. 29.

T cells from an HLA-A-2$^+$ breast cancer patient were tested for stimulation of CEA-specific CTL by autologous DC pulsed with CEA (in the presence of long/ml IL-7). The CTL generated were tested on two different target cells: an HLA-A2$^+$CEA$^+$ cell line (SW403) and an HLA-A2$^-$CEA$^+$ cell line (SW1417). The results are shown in FIG. 29. The CTL activity appeared to be MHC restricted as the killing of HLA-A2$^-$ cells was markedly lower that killing of HLA-A2$^+$ cells. Furthermore, the generation of CTL was dependent on the presence of CEA-pulsed DC in the stimulatory phase, as little killing was observed with effector cells stimulated by cytokines alone (FIG. 30).

Figure 31:
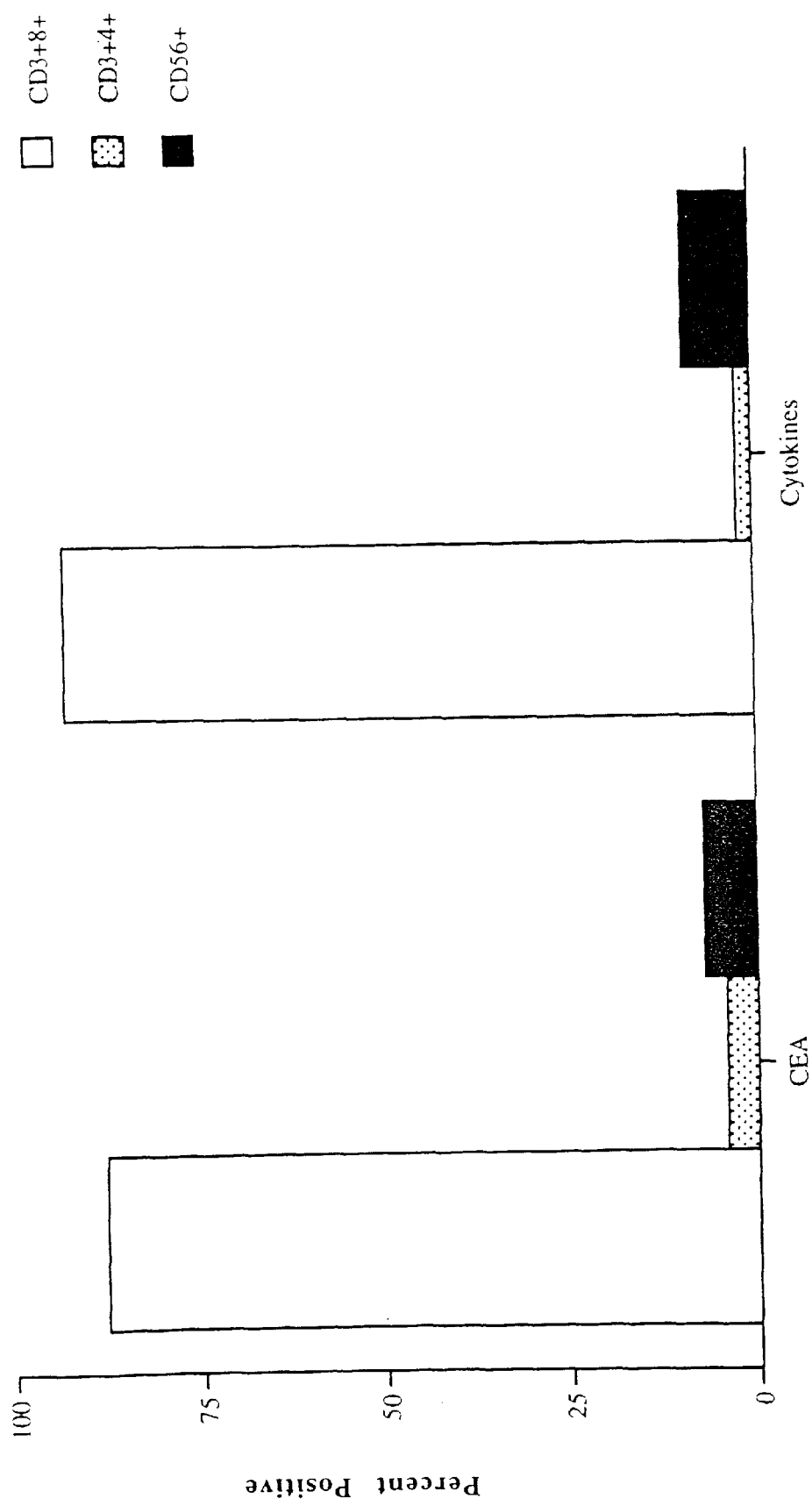
FIG. 31 shows the phenotype of the cells used in FIGS. 29 and 11. Cells stimulated with CEA-pulsed DC ("CEA") or with cytokines alone ("Cytokines") were stained with antibodies to CD3, CD4, CD8, and CD56.

The phenotype of the breast cancer patient's effector cells (on the day of CTL assay) is shown in FIG. 31. The DC-CEA-stimulated and cytokine-stimulated T cells were stained with antibodies to CD3, CD4, CD8, and CD56. The large majority of cells in this effector cell populations were CD3$^+$8$^+$.

REVERSE TRANSCRIPTASE (RT)—POLYMERASE CHAIN REACTION (PCR) ANALYSIS OF TRANSFECTED DENDRITIC CELLS

This example shows successful gene transfer to the dendritic cells using AAV/liposome transfection. The data presented below indicates that the desired genes were successfully transferred to the dendritic cells since mRNA encoding the respective transfected genes was present in the cells.

Dendritic Cell Isolation

PBMCs from normal donor peripheral blood were isolated on Ficoll. 1.5×10$^8$ PBMCs were allowed to adhere to a T150 flask for 2–4 hours at 37° C. in RPMI-10% FCS. After incubation, the nonadherent cells were removed and the adherent cells were cultured in 30 ml of RPMI-10% FCS medium containing 800 units/ml GM-CSF and 500 units/ml IL-4. After 7 days, the differentiated dendritic cells were harvested, washed, and counted.

Transfection

3×10$^6$ cells in serum-free RPMI in 100 mm dishes were transfected for each condition. 30 µg of plasmid pMP6CAT, pMP6ACEA, or pMP6AMART1 DNA were complexed to 60 nmole total lipid as DDAB:DOPE 1:1 liposomes. After the cells were incubated with the complex, additional medium containing fetal calf serum, GM-CSF, and IL-4 was added to bring the final concentration to 10% FCS, 800 units/ml GM-CSF, and 500 units/ml IL-4. The cells were harvested 1, 2, or 3 days after transfection.

Figure 42:
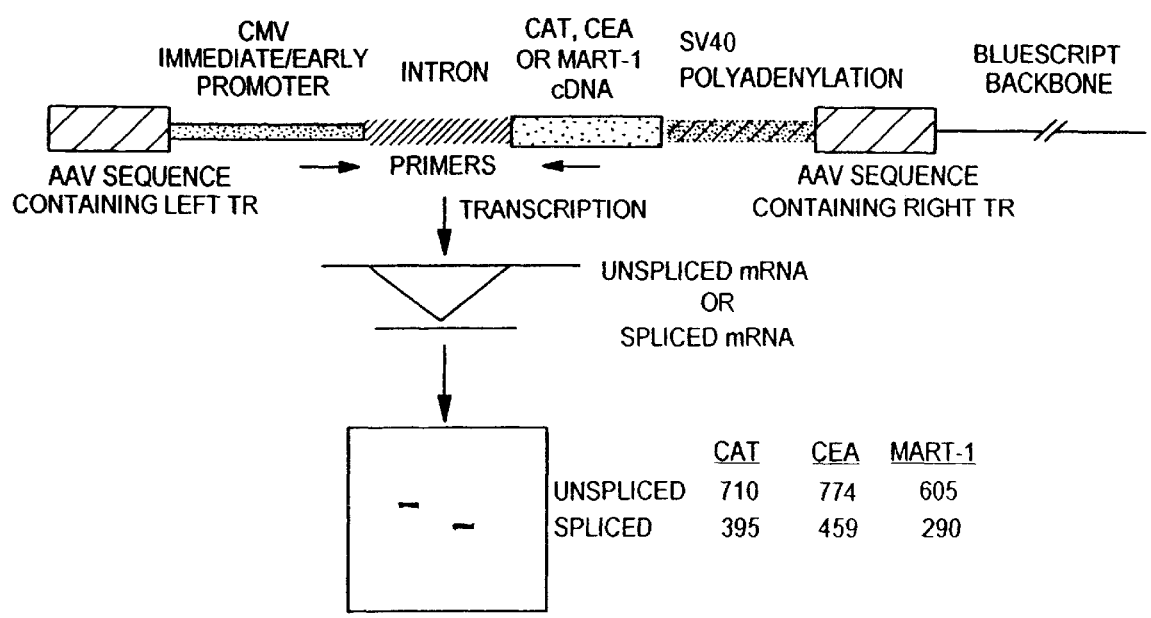
FIG. 42 shows a general schematic of the plasmids containing CAT, CEA or MART-1 and the relationship of the plasmid DNA to the mRNA produced in the reverse transcriptase-polymerase chain reaction analysis of the transfected dendritic cells.

In addition to the dendritic cells, two tumor cell lines were also transfected following the protocol presented above for transfection of the dendritic cells. The tumor cells lines were MCF7 and CEM. MCF7 is a breast cancer tumor cell line and CEM is a lymphoblastoid cell line.

mRNA Isolation mRNA was isolated and treated with DNase to remove contaminating plasmid DNA. Untransfected cells were treated similarly. A portion of mRNA was amplified by PCR without reverse transcriptase. The remaining mRNA was used to synthesize cDNA, which was then amplified by PCR. As a control, plasmid DNA was also amplified by PCR. PCR amplification was carried out using primers that flank the intron portion of the plasmid constructs. These primers will yield a full length product (same size as plasmid control) if the mRNA is unspliced, but a smaller product if the intron has been spliced out (see FIG. 42). PCR products were visualized by gel electrophoresis and their size was determined.

Results

Figure 43:
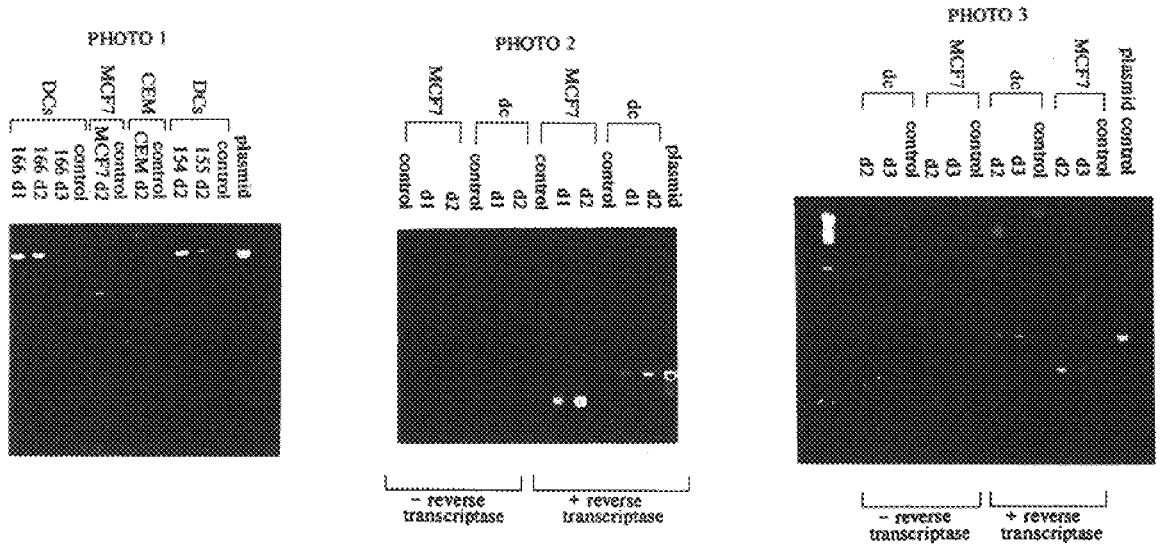
FIG. 43 shows an analysis of the mRNA present in dendritic cells following transfection with either CAT, CEA or MART-1.

The results of the experiments are presented in FIG. 43. Successful gene transfer to dendritic cells was confirmed by the presence of CAT, CEA, and MART-1 transgene mRNA. In all cases, a full-length product (CAT=710, CEA=774, MART-1=605) was detected, indicating that the mRNA from dendritic cells is unspliced. In contrast, mRNA analysis of tumor cell lines (MCF-7, CEM) transfected with the same constructs are positive for the smaller, spliced form. Untransfected cells and samples amplified without reverse transcriptase are negative for transgene mRNA.

Although the mRNA detected in transfected dendritic cells is unspliced, protein expression still occurs, as demonstrated by CAT protein assays and the ability to generate antigen specific CTL. It is believed that increasing the amount of spliced mRNA in dendritic cells may enhance protein expression.

GENERATION OF MELANOMA ANTIGEN-SPECIFIC CTL

A peptide-based approach was employed in which DC were pulsed with MART-1 ("melanoma antigen recognized by T cells"), a tumor-associated antigen that is specifically expressed on melanoma cells and normal melanocytes. An immunodominant MART-1 peptide (AAGIGILTV) is recognized by CTL in the context of Class I HLA-A2 molecules (*J. Exp. Med.* 180:347 (1994)) and was used in the present studies.

DC Isolation

DC were isolated essentially as described above in the studies of anti-CEA responses. After 6–7 days of culture the differentiated DC were harvested, stripped of endogenous peptides, loaded with MART-1 peptide (AAGIGILTV; *J. Exp. Med.* 180:347 (1994)) and used to stimulate CD8+ T cells.

Peptide Stripping and Loading

This was accomplished as described above in the studies of anti-CEA responses.

Generation of CTL

CTL were generated as described above in the anti-CEA responses, except that patient donors were HLA-A2+ melanoma patients. Here, the stimulator DC or T cell-depleted PBMC pulsed with MART-1 peptide (1:5 stimulator:responder ratio) and plated in 24-well plates at a density of $1.5-2\times10^6$ responder cells/well. Two days later, 20U/ml IL-2 was added. Responders were restimulated weekly for a total of 3–4 rounds of stimulation at stimulator:responder ratios ranging between 1:5 and 1:15. Here too, controls included CD8+ captured cells cultured with either (a) DC pulsed with an irrelevant peptide, (b) unpulsed DC or (c) IL-7 only.

Evaluation of Cytotoxicity

HLA-A2-restricted recognition of MART-1 by the CTL generated as above was assessed in a standard 4 hr $^{51}$Cr release assay described above for anti-CEA responses. Recognition of MART-1 peptide by CTL was assessed using T2 target cells preincubated for 2–4 hr with peptide at 40 μg/ml. In addition MART-1-specific cytotoxicity was evaluated using the following HLA-A2+ cell lines as targets: 624 mel (MART-1+), A375 (MART-1−), and/or Colo205 (MART-1−). Labeling of target cells and the assay itself are described above for anti-CEA responses.

RESULTS

Figure 33:
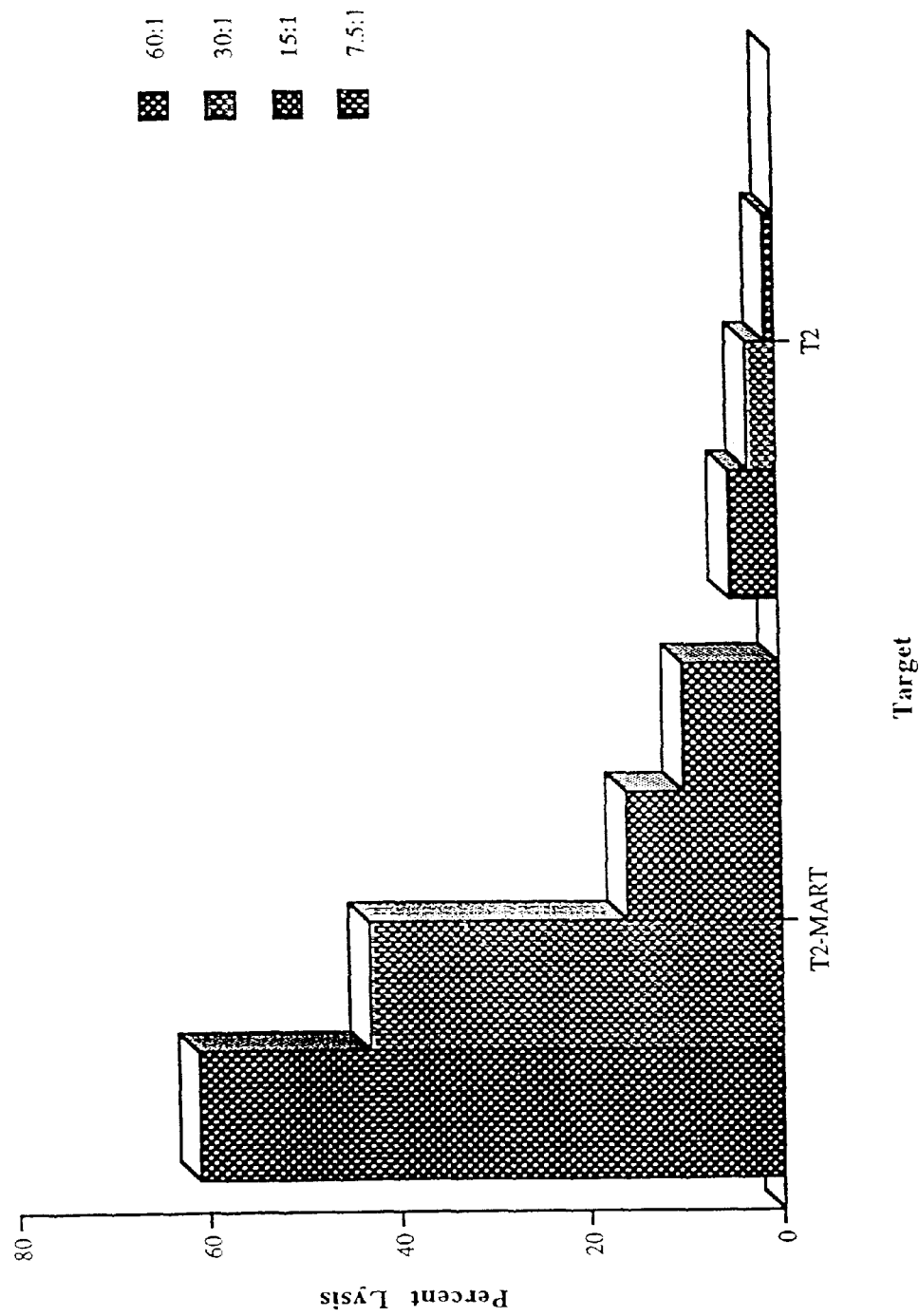
FIGS. 33–35 summarize the "secondary" response of a melanoma patient's lymphocytes to the MART-1 peptide.
Figure 34:
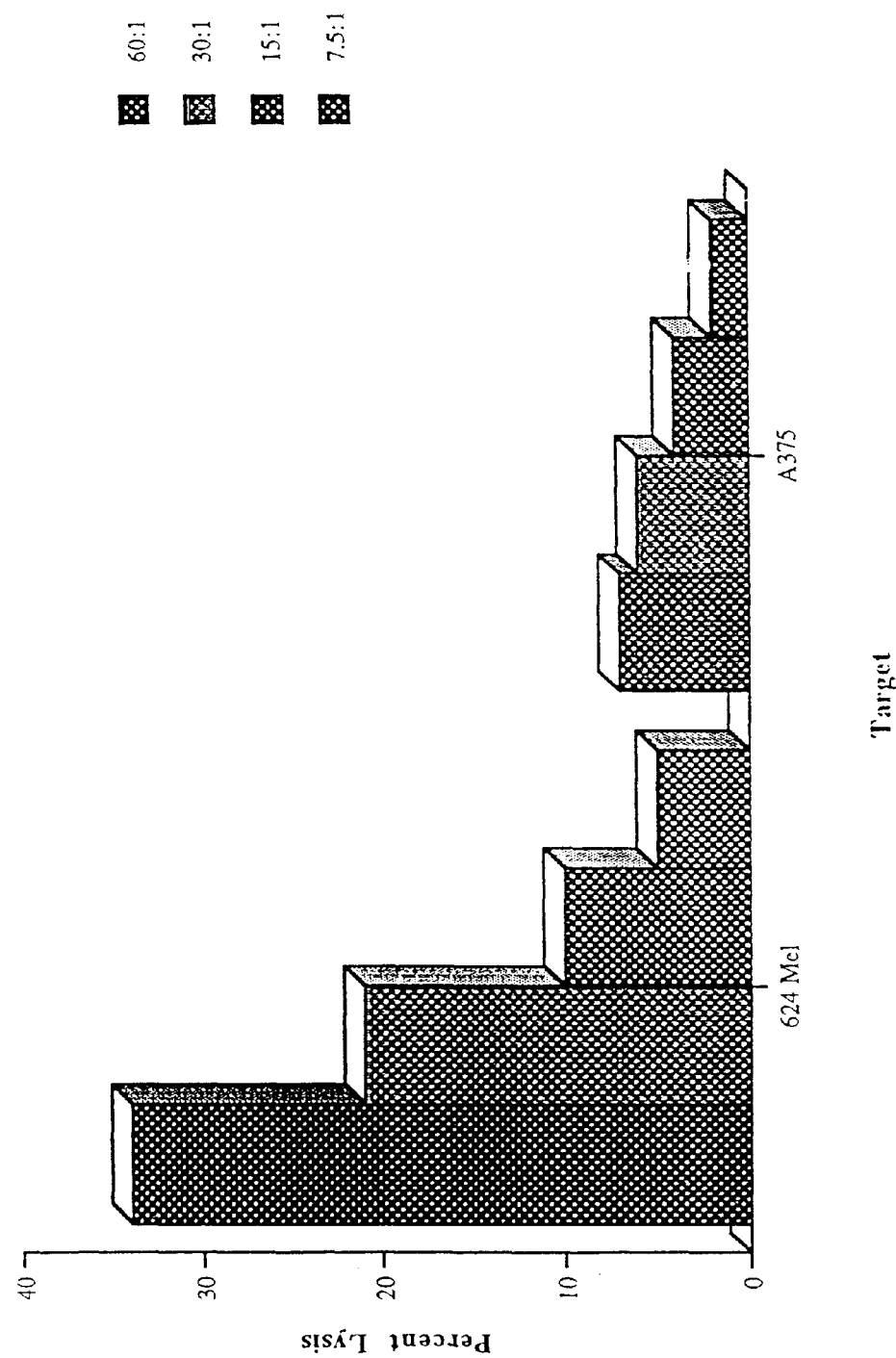
Figure 35:
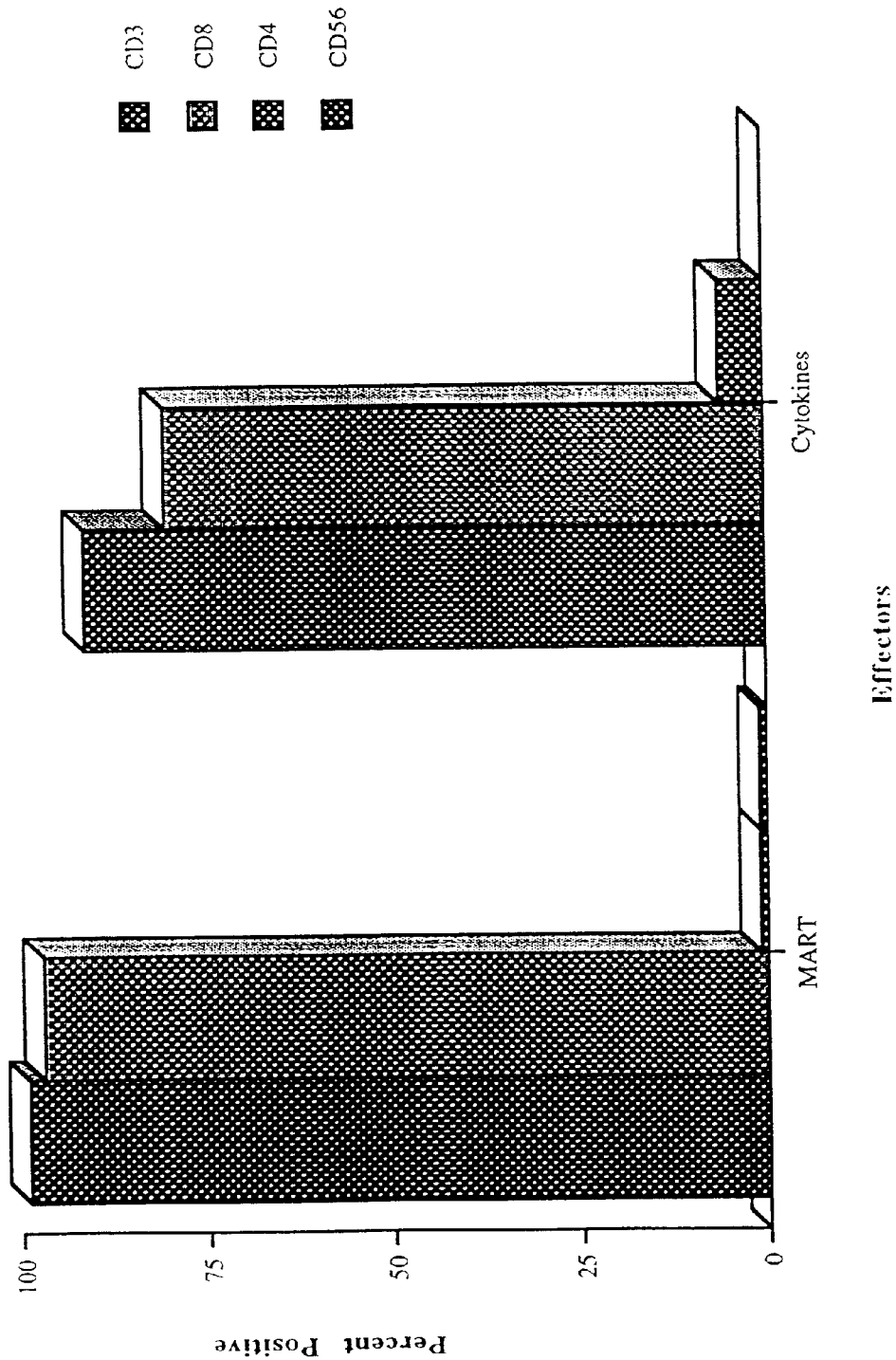

MART-1 specific cytotoxicity by T cells from a melanoma patient on T2 target cells pulsed with MART peptide (T2-MART) and "empty" T2 cells (T2) is shown in FIGS. 33–35. CD8-captured cells stimulated with irradiated DC loaded with MART-1 peptides and cultured with IL-7, and subjected to 3 rounds of stimulation showed a specific cytotoxic response seen as the markedly higher killing of the MART-1-pulsed targets. Specific cytotoxicity against T2-MART (after subtraction of activity on T2) was 60%, 40% and 15% at E:T ratios of 60, 30, and 15, respectively (FIG. 33).

Specificity of the cytotoxic response was also seen by the markedly higher killing of the MART-1+ targets (624mel) compared to MART-1− targets (A375) (FIG. 34). Specific cytotoxicity against 624Mel (after substraction of activity on MART-1− targets) was 25%, 15% and 5% at E:T ratios of 60, 30 and 15, respectively.

The phenotype of the above effector cells on the day of CTL assay is shown in FIG. 35. The DC-MART-stimulated and IL-7-stimulated patient T cells were stained with antibodies to CD3, CD4, CD8, and CD56. Greater than 90% of the effector cells are CD3+CD8+.

Similar studies were done with peripheral blood T cells obtained from a normal, healthy donor (shown in FIGS. 36–38) which presumably reflect a primary response.

Figure 36:
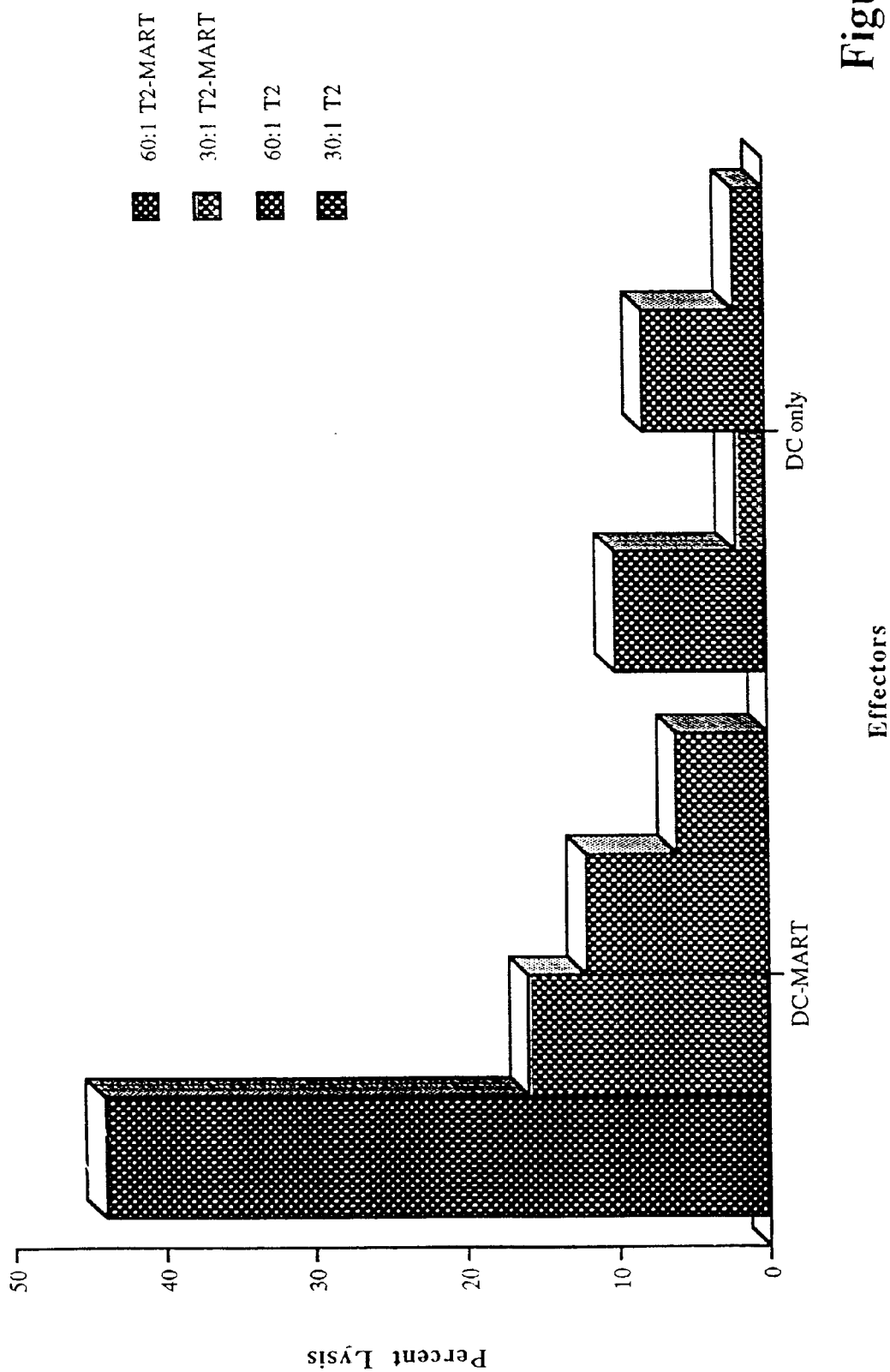
FIGS. 36–38 summarize primary responses of lymphocytes from a healthy donor to the MART-1 peptide

Specificity of the CTL response was demonstrated by the markedly higher killing of the MART-1-pulsed targets compared to unpulsed targets (FIG. 36). Specific cytotoxicity against T2-MART (after subtraction of activity on T2) was 30% and 10% at E:T ratios of 60 and 30, respectively.

Figure 37:
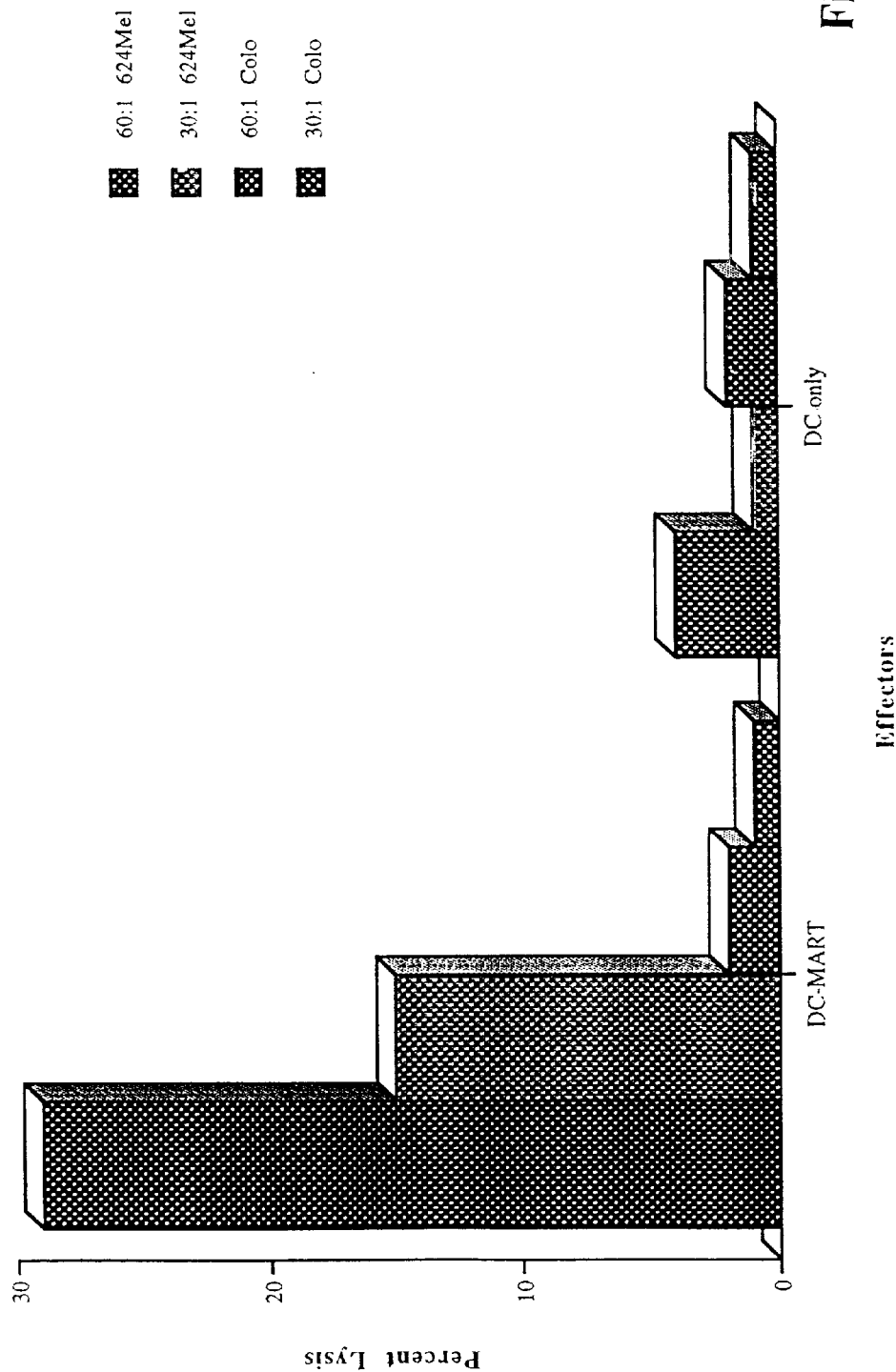

Further evidence for the specificity of the CTL response is shown in FIG. 37, where killing of the MART-1+ targets was markedly higher than killing of MART-1− targets. Specific cytotoxicity against 624Mel (after substraction of activity on MART-1− Colo targets) was 30% at an E:T ratio of 60.

Figure 38:
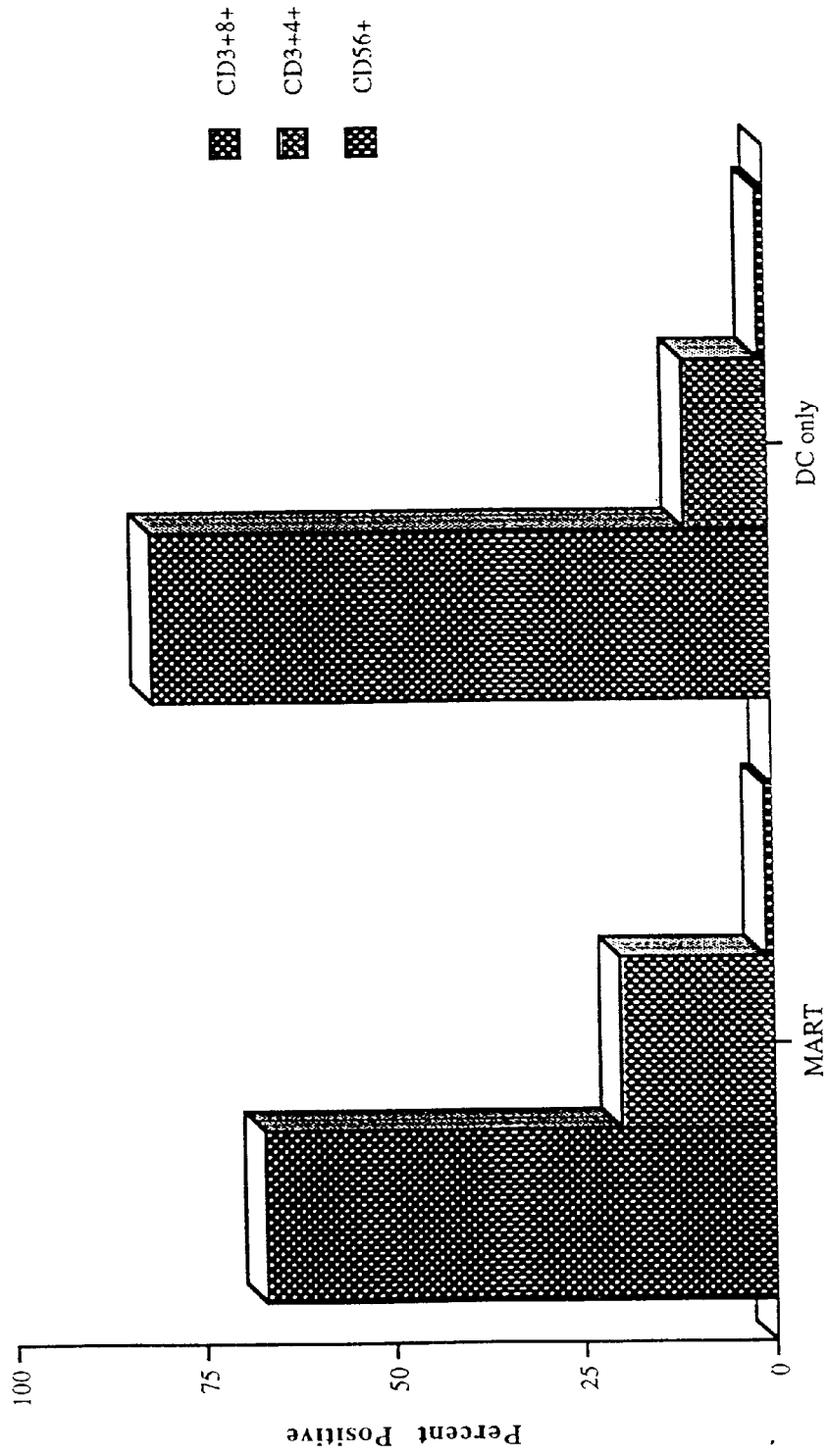

The phenotype of the above effector cells on the day of CTL assay is shown in FIG. 38. The DC-MART-stimulated and IL-7-stimulated normal T cells were stained with antibodies to CD3, CD4, CD8, and CD56. About 70% of the effector cells were CD3+CD8+.

USE OF A MART-1 GENE MODIFIED DENDRITIC CELL AS AN ANTIGEN PRESENTING CELL (APC)

This experiment demonstrated that transformed dendritic cells can express and present peptide antigens encoded by the tumor associated antigen (TAA) MART-1 gene and that these dendritic cells can stimulate CD8+ cells specific for MART-1 resulting in killing by the CD8+ cells of target cells which present the MART-1 antigen on their surface.

Dendritic Cell Isolation

Dendritic cells (DC) were isolated using a modification of Romani et al. (*J. Exp. Med.*, 180:83 (1994)). Briefly, $1.5-10^8$ PBMC from an HLA A2+ donor were allowed to adhere to a T150 flask for 2–4 hours at 37° C. in RPMI-10% FCS. After incubation, the nonadherent cells were removed and the adherent cells were cultured in 30 ml of RPMI-10% FCS medium containing 800 units/ml GM-CSF and 500 units/ml IL-4. The cells were harvested 6 to 7 days after isolation.

Cell preparation

The harvested cells were resuspended in room temperature serum-free RPMI 1640 and the total number of cells (all cell types) was determined. The volume of the cells was then adjusted to yield $1-5\times10^6$ cells/ml.

Preparation of DNA:Liposome Complexes

Plasmid pMP6AMART1 contains the gene for the tumor associated antigen (TAA) gene MART-1, a melanoma antigen recognized by T cells cloned into pMP6. The MART-1 coding sequence was produced by PCR using primers generated from published sequences. The PCR product was digested with NheI and BamHI and cloned into NheI and BamHI digested pMP6 and filled in with T4 DNA polymerase, CIP and Klenow. For each $1\times10^6$ cells to be transfected, 10 μg of plasmid DNA at a concentration of 1 mg/ml in sterile $H_2O$ were aliquoted into a sterile, round-bottom tube and combined with 10 nmoles of DDAB as DDAB:DOPE 1:1 liposomes at a concentration of 1 μmole DDAB/ml in sterile $H_2O$. The solution was mixed by gentle swirling and incubated at room temperature for 10 to 15 minutes. Serum-free RPMI 1640 was then added to the DNA:liposome complex. The volume of medium added equaled one-half of the volume of the cell suspension.

Liposome Transfection

The DNA:liposome complex was transferred to the cell suspension and the mixture was incubated at room temperature for 15 minutes. 2×dendritic cell medium (RPMI 1640+ 20% FCS+1600 U/ml GM CSF+1000 U/ml IL-4) was then added to the cells. The volume of medium added equaled the total volume of cells and complex. The cell suspension was then transferred to appropriate sized culture containers and placed in a 37° C., 5% $CO_2$ incubator.

Post-Transfection Assay

The day following transfection, the transfected dendritic cells (stimulators) were harvested, counted and mixed with autologous cytolytic T cells (responders) from a normal HLA-A2+ donor that had been captured on CD8 MicroCellector flasks. The stimulators were added to the responder cells at a ratio between 1:3 and 1:10 and 10 ng/ml IL7 was added to the culture. At 10 days post stimulation, another 10 ng/ml IL7 were added to the culture along with transfected dendritic cells. Two additional restimulations were performed weekly for a total of four stimulations. Additional IL7 is added between the weekly stimulations.

Five days after the final restimulation, the CTL were harvested and assayed for specific cytotoxicity against appropriate target cells by $^{51}Cr$ release.

Cytotoxicity Analysis

HLA-A2 restricted MART-1 recognition by CTL was assessed by a standard 4-hour $^{51}Cr$ release cytotoxicity assay. The MART-1 peptide (AAGIGILTV) is recognized by CTL in the context of Class I HLA-A2 molecules (*J. Exp. Med.*, 180:347 (1994)). Recognition of MART-1 peptide by CTL was assessed using T2 cells pulsed with MART-1 peptide (T2+MART-1) and "empty" T2 cells (empty T2). T2 cells are a processing defective cell line which expresses empty A2 molecules until stabilized by the addition of peptide. The T2 cells pulsed with MART-1 were preincubated for 2–4 hours with MART-1 peptide at 40 mg/ml. Target cells were labeled overnight with 100 mCi$^{51}$Cr; they were washed and mixed with effector cells at varying effector:target (E:T) ratios in U-bottom microtiter plates. After a 4 hour incubation, supernatants were harvested, and the amount of $^{51}Cr$ released was measured by a beta counter. Percent specific cytotoxicity was calculated as follows: [(cpm of test sample–cpm of spontaneous $^{51}Cr$ release)/ (cpm of maximal $^{51}Cr$ release–cpm of spontaneous $^{51}Cr$ release)]×100.

Results

Figure 44A:
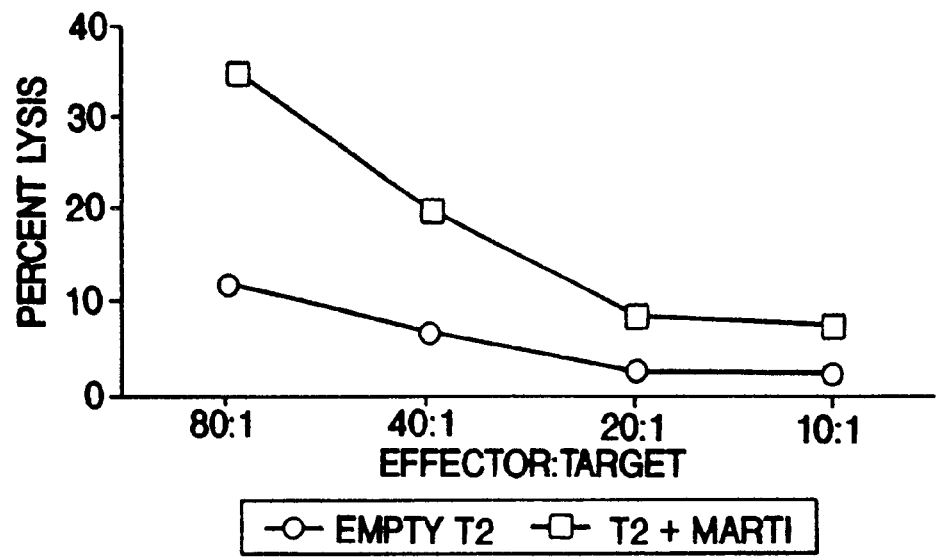
FIG. 44a shows the response of cytolytic T cells (CTL) to MART-1 peptide loaded and empty target cells following exposure of the CTL to dendritic cells expressing the MART-1 gene.
Figure 44B:
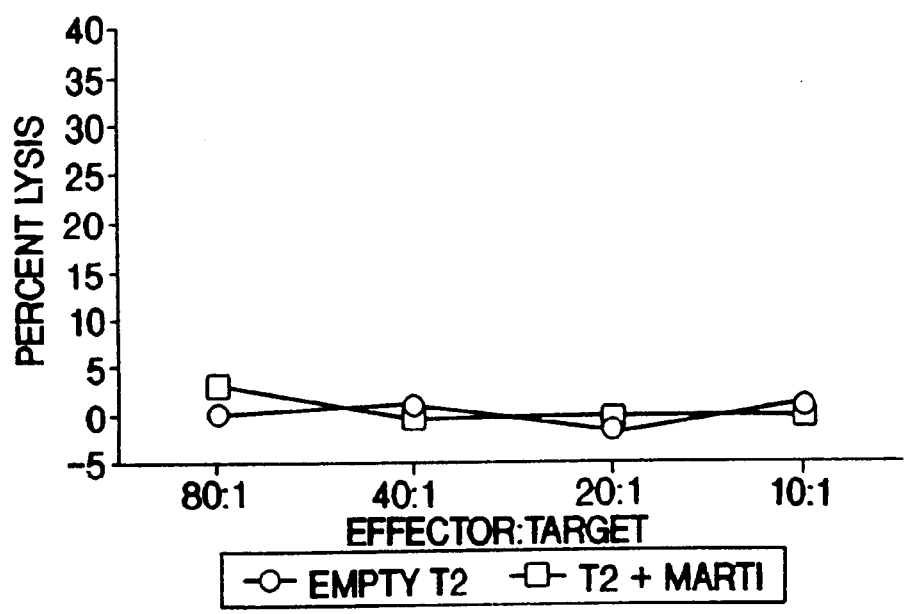
FIG. 44b shows the response of CTL to MART-1 peptide loaded and empty target cells following cytokine stimulation only.

The results presented in FIG. 44a show that T cells stimulated with gene modified dendritic cells expressing the tumor associated antigen gene MART-1 demonstrate significant cytotoxic response against MART-1 peptide loaded T2 cells (T2+MART-1). There was some background killing of empty T2 cells at the high effector:target ratio. T cells stimulated with cytokine only (FIG. 44b) were not cytotoxic against either empty or peptide loaded targets. The response observed was antigen specific. This data demonstrates that a single peptide response can be generated by stimulating with dendritic cells which express the whole gene product. It is believed that other HLA restricted responses can be generated using gene modified dendritic cells.

GENERATION OF HIV ANTIGEN-SPECIFIC CTL

Figure 39:
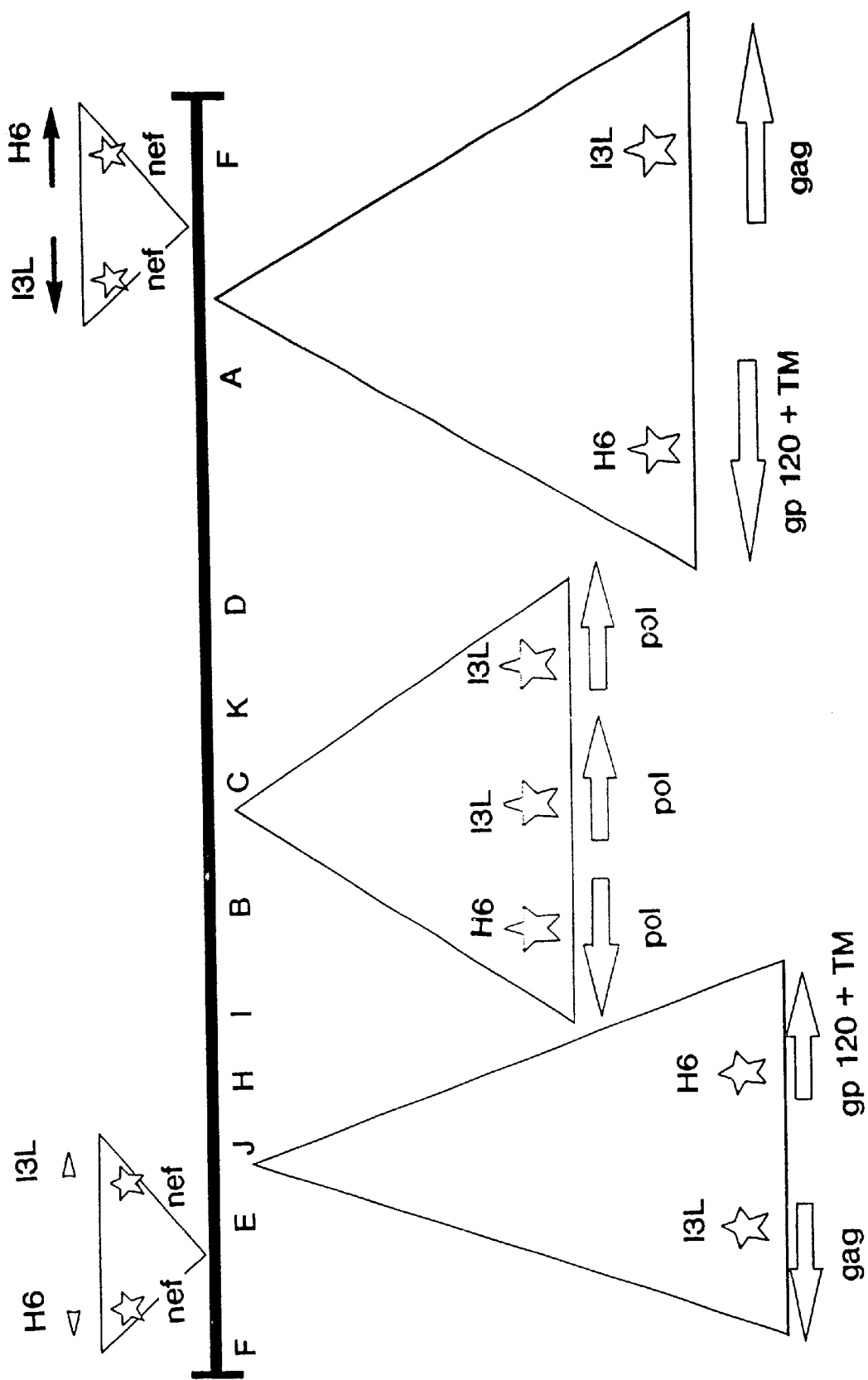
FIG. 39 is a schematic illustration of the genetic map of canarypox vector vCP300 which expresses nef, gag, gp120 and pol genes of HIV.

A canarypox virus construct vCP300 (Virogenetics Corp., Troy, N.Y.) which includes genes encoding HIV proteins (gag, pol, gp120, nef) is diagrammed in FIG. 39. This vector was used to infect either PBMC depleted of CD8+ and CD4+ cells or DC to test whether these cells would express HIV peptides in immunogenic form capable of stimulating HIV-specific CTL. The vCP300 vector was mixed in polypropylene tubes with the cells being transfected at a multiplicity of infection (MOI) of 5 or 10 and incubated at 37° C. in 5% $Co_2$ for one hour. For analysis of HIV gene expression, the infected cells were incubated for an additional 18 to 24 hours. Infected cells were used to stimulate cultures immediately. Any remaining cells were frozen for later use.

CD8+ responder cells obtained from HIV+ donors were cultured in AIM V media supplemented with 100 IU/ml rIL-2 (from Cetus). Stimulator cells were added on days 0 and 7 at a responder:stimulator ratio of 10:1.

Healthy PBMC obtained from buffy coats were cultured in AIM V medium supplemented with 5% human AB serum (Advanced Biotechnologies Inc., Columbia, Md.), 5.0 ng/ml rIL-7 (Genzyme Corp., Cambridge, Mass.). In addition, 100 IU/ml of rIL-2 was added 48 hours after the second stimulation on day 7. The cultures were stimulated as described above for CD8+ cultures.

Mature dendritic cells were cultured in RPMI-1640 medium supplemented with 10% FCS, 800 U/ml GM-CSF and 500 U/ml rIL-4 (both from Biosource International, Camarillo, Calif.).

Evaluation of Cytotoxicity

Autologous CD4+ cells expressing selected HIV antigens were used as target cells in a $^{51}Cr$ release assay performed generally as described above. The target cells were prepared by infection with vaccinia virus vectors (Virogenetics Corp., Troy, N.Y.) containing either (1) env, (2) gag/pol, or (3) nef proteins of HIV. Infection was accomplished by coincubating the CD4+ cells and the vaccinia virus vector (MOI=10) for 1 hour at 37° C. The infected cells were then labeled with $^{51}Cr$ at a concentration of 100 $\mu$Ci/ml per 10$^6$ cells overnight at 37° C. in an atmosphere of 5% $CO_2$ in individual wells of a 24-well tissue culture plate.

Effector cells and target cells were mixed at E:T ratios ranging from 5 to 40, depending on cell numbers, in 96-well microplates and incubated in a standard 4 hour cytotoxicity assay. % Cytotoxicity was calculated as above.

Analysis of vCp300 Expression

Three populations of cells were infected with canarypox construct vCP300 as detailed above: (a) PBMC. (b) PBMC depleted of CD8- and CD4-bearing cells and (c) DC. These cells were incubated with either buffer (PBS-CMF), pooled human AB serum, or pooled serum from HIV+donors (New York State Health Dept., Troy, N.Y.). As a second step, these cells were incubated with fluorescein isothiocyanate-conjugated goat anti-human IgG (Jackson ImmunoResearch Laboratories, Inc., West Grove, Pa.). Stained cells were analyzed by flow cytometry (Becton Dickinson Immunocytometry Systems, San Jose, Calif.).

RESULTS

Figure 40:
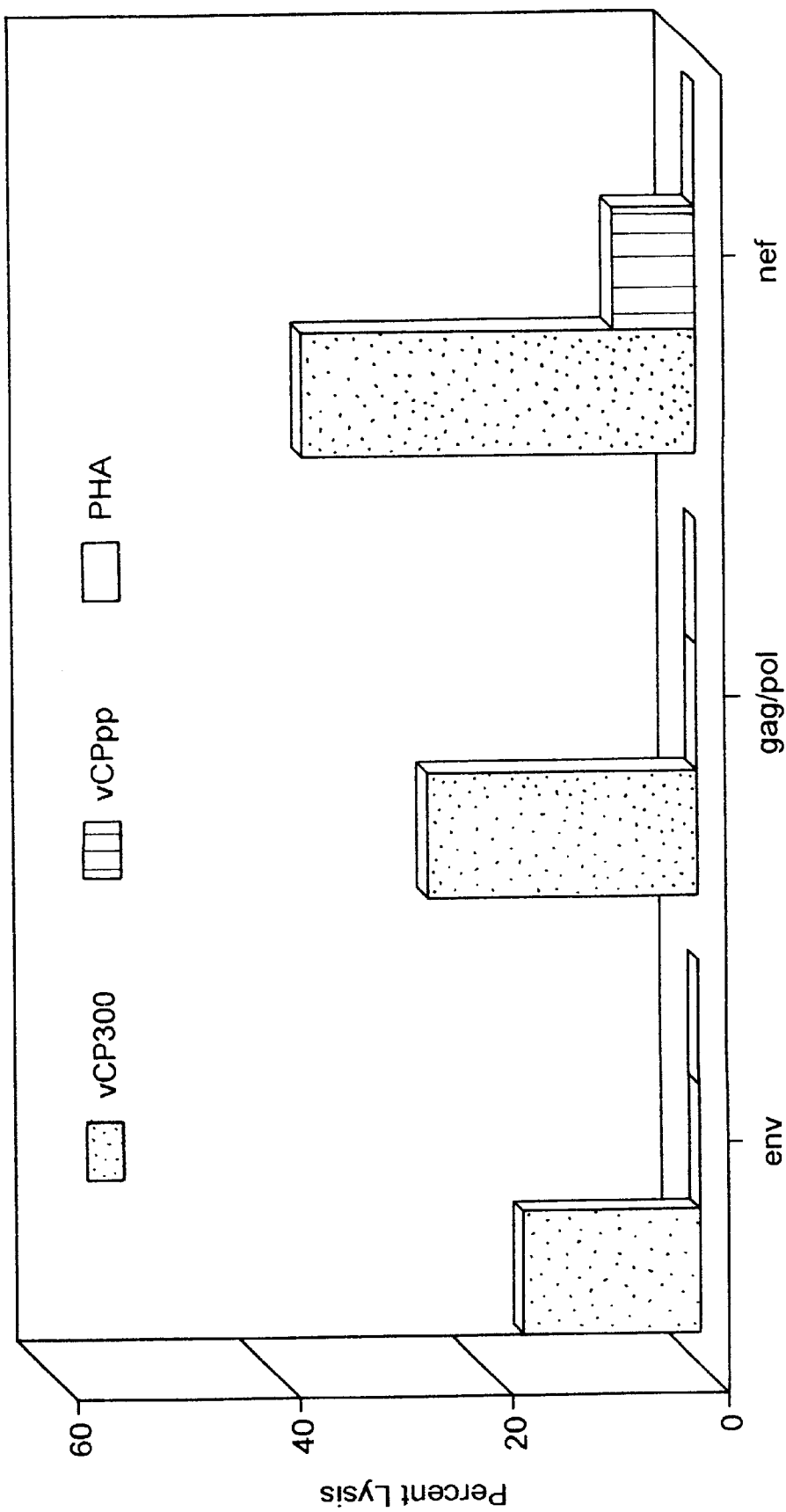
FIG. 40 shows the cytotoxic activity of effector cells stimulated in primary culture by autologous DC cells infected with canarypox construct vCP300 against target cells expressing env, gag/pol or nef antigens of HIV. The responder:stimulator ratio in culture was 10:1 and the effector:target ratio was 40:1. Control groups included cells stimulated by DC infected with a canarypox virus construct lacking HIV genes (vCPpp) or cells stimulated by the mitogen phytohemagglutinin (PHA).
Figure 41:
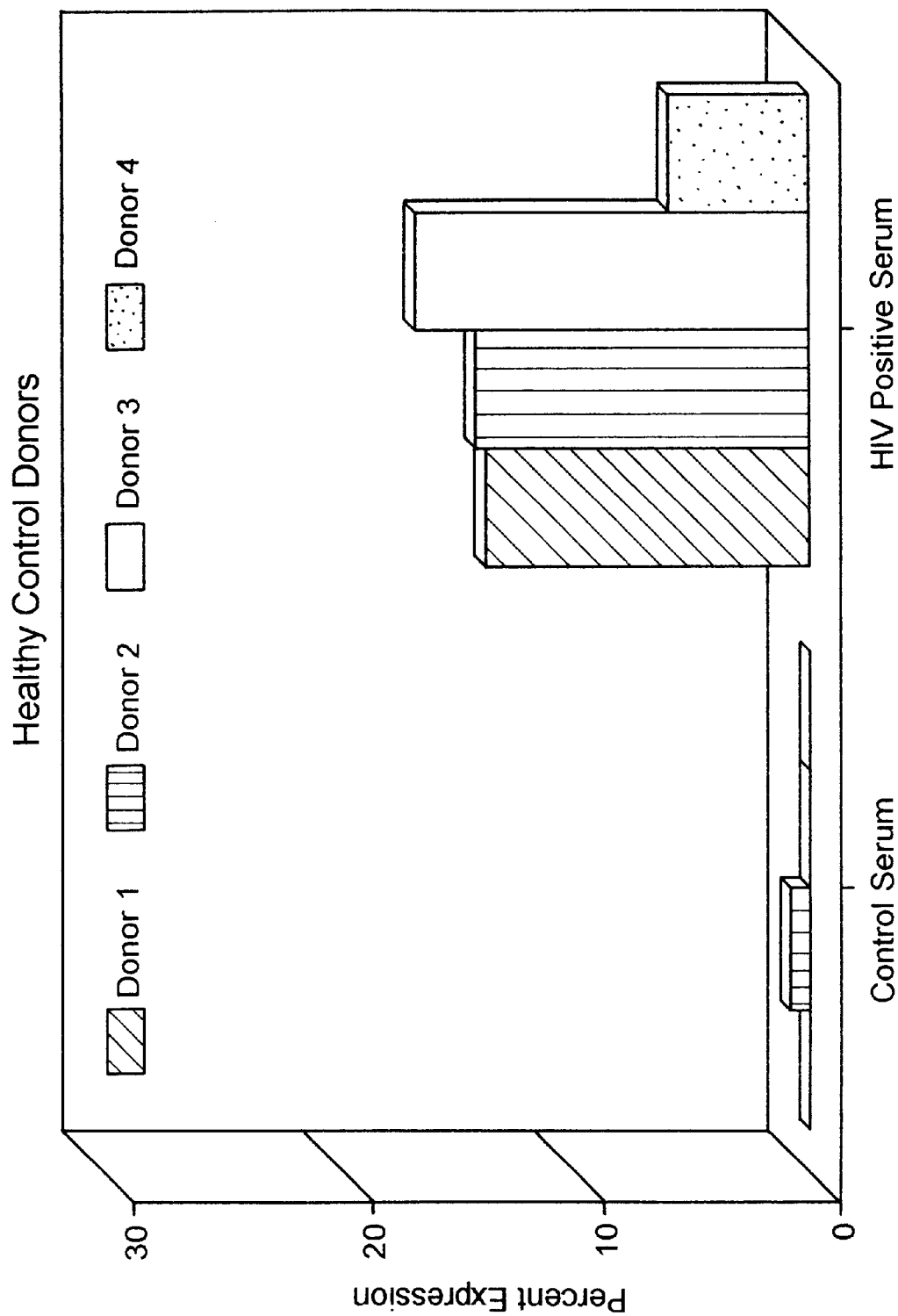
FIG. 41 summarizes a flow cytometry analysis of the HIV antigens expressed on DC of 4 healthy donors infected in culture by the vCP300 vector. Cells were stained with serum from HIV$^+$ donors or pooled control serum.

The results of these studies appear in FIGS. 40–41. PBMC stimulated with autologous DC infected with canarypox construct vCP300 had cytotoxic activity against autologous target cells expressing HIV env, gag/pol or nef (FIG. 40). Cytotoxicity activity ranged from 18% to 30% lysis. The activity was significantly higher than the background activity of PBMC stimulated in culture by DC infected with a control canarypox construct lacking any HIV genes (vCPpp). Similarly, PBMC stimulated by the mitogen PHA showed no lytic activity. Cytotoxicity was directed toward all of the HIV proteins present in the construct used to infect the antigen-presenting DC.

Flow cytometry was used to analyze expression of HIV proteins on DC isolated from 4 healthy donors and infected with vCP300. The results, shown in FIG. 41, indicate that HIV proteins were detected by binding of anti-HIV antibodies (in the form of serum from HIV+ donors) to infected DC. Control serum did not react with any of the infected DC preparations. The percent of cells expressing HIV antigens acquired through infection with the vCP300 vector ranged from 5% to 15%.

As used herein and in the appended claims, the singular forms "a," "an" and "the" include plural referents unless the context clearly dictates otherwise. Thus, for example, reference to "a formulation" includes mixtures of different formulations and reference to "the method of treatment" includes reference to equivalent steps and methods known to those skilled in the art, and so forth.

Unless defined otherwise, all technical and scientific terms used herein have the same meaning as commonly understood by one of ordinary skill in the art to which this invention belongs.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation. It is to be understood that the phraseology or terminology employed herein is for the purpose of description and not of limitation. Although any methods and materials similar or equivalent to those described herein can be used in the practice or testing of the invention, the preferred methods and materials are described.

What is claimed is:

1. A non-immortalized dendritic cell ex vivo transfected by a composition comprising a cationic liposome and a plasmid which includes an adeno-associated virus inverted terminal repeat and a DNA sequence of interest encoding a tumor-associated antigen not native to said dendritic cell.

2. A cell according to claim 1 wherein said plasmid further comprises a DNA sequence of interest encoding a cytokine.

3. A cell according to claim 2 wherein said plasmid is pMP6.

4. A method for introducing a DNA sequence of interest into a dendritic cell ex vivo comprising the steps of:
   a. providing a composition comprising a cationic liposome, adeno-associated virus material and a DNA sequence of interest encoding a tumor-associated antigen; and
   b. contacting the composition of step (a) ex vivo with a dendritic cell that comprises genetic material under conditions which introduce the DNA sequence of interest into said cell.

5. A method for introducing a DNA sequence of interest into a dendritic cell in vitro comprising contacting said cell with a composition which comprises a cationic liposome and a plasmid including at least one inverted terminal repeat from adeno-associated virus and a genetic sequence of interest operably linked to a non-adeno-associated virus promoter.

6. A method for producing a protein in a dendritic cell in vitro comprising contacting said cell with a composition which comprises a cationic liposome and a plasmid including at least one inverted terminal repeat from adeno-associated virus and a genetic sequence encoding said protein operably linked to a non-adeno-associated virus promoter.

7. A transfected dendritic cell in vitro comprising at least one inverted terminal repeat from adeno-associated virus and a genetic sequence of interest operably linked to a non-adeno-associated virus promoter.

8. A method for treating cancer in a subject in need of treatment comprising administering to said subject dendritic cells which have been transfected ex vivo with a composition comprising a cationic liposome and a plasmid comprising a DNA sequence which encodes a tumor-associated antigen and at least one inverted terminal repeat from adeno-associated virus, wherein the expression of said tumor-associated antigen by said dendritic cell in vivo results in an anti-tumor response which treats said cancer.

9. The method of claim 8 wherein said plasmid further includes a DNA sequence encoding a cytokine, a reporter molecule or a selectable marker.

10. The method of claim 8 wherein said plasmid is pMP6 in which is inserted said DNA sequence encoding said tumor-associated antigen.

11. The method of claim 8 wherein said tumor-associated antigen is selected from the group consisting of carcinoembryonic antigen, a breast tumor antigen, a colorectal tumor antigen, a gastric tumor antigen, a pancreatic tumor antigen, a lung tumor antigen, an ovarian tumor antigen, a bladder tumor antigen, a prostate tumor antigen, a melanoma antigen, a leukemia antigen or a lymphoma antigen.

12. The method of claim 8 wherein said DNA sequence encoding said tumor-associated antigen integrates into the genetic material of said dendritic cell.

13. The method of claim 8 wherein said tumor-associated antigen is selected from the group consisting of: MART-1 (Melan A), CEA, MUC-1, p53, ras, her2, Mage1, Mage3, tyrosinase, PSA, PSMA, Rage, Bage, Gage, E1A, E6, E7, EBNA2, EBNA-3A, EBNA-3C, EBNA-4, EBNA-6, neu and gp100.

14. A method for generating an anti-tumor response in vivo in a subject comprising administering dendritic cells which have been transfected ex vivo with a composition comprising a cationic liposome and a plasmid comprising a DNA sequence which encodes a tumor-associated antigen and at least one inverted terminal repeat from adeno-associated virus, wherein the expression of said tumor-associated antigen by said dendritic cell in vivo results in an anti-tumor response.

15. The method of claim 14 wherein said plasmid further includes a DNA sequence encoding a cytokine, a reporter molecule or a selectable marker.

16. The method of claim 14 wherein said plasmid is pMP6 in which is inserted said DNA sequence encoding said tumor-associated antigen.

17. The method of claim 14 wherein said tumor-associated antigen is selected from the group consisting of carcinoembryonic antigen, a breast tumor antigen, a colorectal tumor antigen, a gastric tumor antigen, a pancreatic tumor antigen, a lung tumor antigen, an ovarian tumor antigen, a bladder tumor antigen, a prostate tumor antigen, a melanoma antigen, a leukemia antigen or a lymphoma antigen.

18. The method of claim 14 wherein said DNA sequence encoding said tumor-associated antigen integrates into the genetic material of said dendritic cell.

19. The method of claim 14 wherein said tumor-associated antigen is selected from the group consisting of: MART-1 (Melan A), CEA, MUC-1, p53, ras, her2, Mage1, Mage3, tyrosinase, PSA, PSMA, Rage, Bage, Gage, E1A, E6, E7, EBNA2, EBNA-3A, EBNA-3C, EBNA-4, EBNA-6, neu and gp100.

20. The method of claim 5 wherein said genetic sequence of interest encodes for a cytokine.

21. The method of claim 6 wherein said genetic sequence of interest encodes for a cytokine.

22. The method of claim 20 wherein said cytokine is IL-2.
23. The method of claim 21 wherein said cytokine is IL-2.
24. The method of claim 9 wherein said cytokine is IL-2.
25. The method of claim 15 wherein said cytokine is IL-2.
26. The method of claim 7 wherein said genetic sequence of interest encodes for a cytokine.
27. The method of claim 26 wherein said cytokine is IL-2.

* * * * *